(12) United States Patent
Von Wronski et al.

(10) Patent No.: US 7,884,183 B2
(45) Date of Patent: *Feb. 8, 2011

(54) COMPOUNDS FOR TARGETING ENDOTHELIAL CELLS, COMPOSITIONS CONTAINING THE SAME AND METHODS FOR THEIR USE

(75) Inventors: Mathew A. Von Wronski, Moorestown, NJ (US); Edmund R. Marinelli, Lawrenceville, NJ (US); Adrian D. Nunn, Lambertville, NJ (US); Radhakrishna K. Pillai, Cranbury, NJ (US); Kondareddiar Ramalingam, Dayton, NJ (US); Michael F. Tweedle, Bexley, OH (US); Karen E. Linder, Kingston, NJ (US); Palaniappa Nanjappan, Princeton, NJ (US); Natarajan Raju, Kendall Park, NJ (US); Feng Yan, Grand-Lancy (CH); Michel Schneider, Troinex (CH)

(73) Assignee: Bracco Suisse SA, Manno (CH)

(*) Notice: Subject to any disclaimer, the term of this patent is extended or adjusted under 35 U.S.C. 154(b) by 924 days.

This patent is subject to a terminal disclaimer.

(21) Appl. No.: 11/381,908

(22) Filed: May 5, 2006

(65) Prior Publication Data
US 2006/0263303 A1    Nov. 23, 2006

Related U.S. Application Data

(60) Division of application No. 09/871,974, filed on Jun. 4, 2001, now Pat. No. 7,109,167, which is a continuation-in-part of application No. 09/585,364, filed on Jun. 2, 2000, now abandoned.

(51) Int. Cl.
A61K 38/00    (2006.01)
A61K 51/00    (2006.01)
(52) U.S. Cl. .............. 530/324; 512/12; 512/2; 424/1.69
(58) Field of Classification Search ............... None
See application file for complete search history.

(56) References Cited

U.S. PATENT DOCUMENTS

| | | | |
|---|---|---|---|
| 5,659,041 A | 8/1997 | Pollack | |
| 5,789,555 A | 8/1998 | Pollack | |
| 5,821,330 A | 10/1998 | Itaya | |
| 5,855,866 A | 1/1999 | Thorpe et al. | |
| 6,051,230 A | 4/2000 | Thorpe et al. | |
| 6,252,664 B1 | 6/2001 | Garbera-Guillem | |
| 6,261,535 B1 | 7/2001 | Thorpe et al. | |
| 6,261,537 B1 | 7/2001 | Klaveness et al. | |
| 6,264,917 B1 | 7/2001 | Klaveness et al. | |
| 6,333,110 B1 | 12/2001 | Garbera-Guillem | |
| 6,521,211 B1 | 2/2003 | Unger et al. | |
| 6,777,534 B1 | 8/2004 | Klagsbrun et al. | |
| 6,800,273 B2 | 10/2004 | Rajopadhye et al. | |
| 7,052,705 B2 | 5/2006 | Rosenbaum et al. | |
| 7,109,167 B2 * | 9/2006 | Von Wronski et al. | ........ 514/12 |
| 2002/0001566 A1 | 1/2002 | Rajopadhye et al. | |
| 2003/0082103 A1 | 5/2003 | Wartchow et al. | |
| 2003/0133972 A1 | 7/2003 | Danthi et al. | |

FOREIGN PATENT DOCUMENTS

| | | |
|---|---|---|
| EP | 0649857 | 4/1995 |
| WO | WO 94/10202 | 5/1994 |
| WO | 95/13832 | 5/1995 |
| WO | WO 96/40285 | 12/1996 |
| WO | WO 98/18498 | 5/1998 |
| WO | WO 98/18500 | 5/1998 |
| WO | WO 98/18501 | 5/1998 |
| WO | WO 98/47541 | 10/1998 |
| WO | WO 98/53857 | 12/1998 |
| WO | WO 99/13919 | 3/1999 |
| WO | WO 99/20312 | 4/1999 |
| WO | WO 99/29861 | 6/1999 |
| WO | WO 99/40947 | 8/1999 |
| WO | 99/51628 | 10/1999 |
| WO | WO 99/58612 | 11/1999 |
| WO | WO 01/42284 | 6/2001 |
| WO | WO 01/54723 | 8/2001 |
| WO | WO 01/62942 | 8/2001 |
| WO | WO 01/70945 | 9/2001 |
| WO | WO 01/83693 | 11/2001 |
| WO | 01/98294 | 12/2001 |
| WO | WO 01/97850 | 12/2001 |
| WO | WO 01/98094 | 12/2001 |
| WO | WO 02/07747 | 1/2002 |
| WO | WO 03/028643 | 4/2003 |

(Continued)

OTHER PUBLICATIONS

Dunn-Dufault, "5, Convenient Preparation of No-Carried-Added-Technetium-99m", Radiopharmaceuticals Using Solid-Phase Technology, 1999, pp. 832-837, vol. 10., XP002200847 Washington, US; abstract; figures 1,2.

(Continued)

*Primary Examiner*—Maury Audet
(74) *Attorney, Agent, or Firm*—Kramer Levin Naftalis & Frankel LLP

(57) ABSTRACT

The present invention provides compounds for targeting endothelial cells, tumor cells or other cells that express the NP-1 receptor, compositions containing the same and methods for their use. Additionally, the present invention includes diagnostic, therapeutic and radiotherapeutic compositions useful for visualization, therapy or radiotherapy.

14 Claims, 7 Drawing Sheets

FOREIGN PATENT DOCUMENTS

| WO | WO 03/029814 | 4/2003 |
| WO | WO 03/092737 | 11/2003 |
| WO | WO 03/094617 | 11/2003 |
| WO | WO 03/103581 | 12/2003 |

OTHER PUBLICATIONS

Online Medical Dictionary. "Amino acid". http://cancerweb.ncl.ac.uk/cgi-bin/omd?query=amino+acid. Nov. 19, 1997.

Online Medical Dictionary. "Analogue". http://cancerweb.ncl.ac.uk/cgi-bin/omd?query=analogue. Jan. 10, 1998.

Dunn-Default et al. "Convenient Preparation of No-Carrier-Added Technetium-99m Radiopharmaceuticals Using Solid-Phase Technology" Bioconjugate Chemistry, vol. 10, 1999, pp. 832-837.

Goodbody et al. "A new Tc-99m labelled peptide inflammation imaging agent" European Journal of Nuclear Medicine, vol. 21, No. 8, Aug. 1, 1994, p. 790.

Iles et al. "A pilot phase II clinical study on imaging inflammatory lesions in patients with Crohn's disease using Tc-99m RP128" Journal of Nuclear Medicine, vol. 39, No. 5, May 1998, p. 271P.

* cited by examiner

```
                        SEQUENCE LISTING

<160> NUMBER OF SEQ ID NOS: 13

<210> SEQ ID NO 1
<211> LENGTH: 4
<212> TYPE: PRT
<213> ORGANISM: Artificial
<220> FEATURE:
<223> OTHER INFORMATION: Description of Artificial Sequence:
      Synthetic Peptide

<400> SEQUENCE: 1

Thr Lys Pro Arg
1

<210> SEQ ID NO 2
<211> LENGTH: 5
<212> TYPE: PRT
<213> ORGANISM: Artificial
<220> FEATURE:
<223> OTHER INFORMATION: Description of Artificial Sequence:
      Synthetic Peptide

<400> SEQUENCE: 2

Thr Lys Pro Pro Arg
1               5

<210> SEQ ID NO 3
<211> LENGTH: 6
<212> TYPE: PRT
<213> ORGANISM: Artificial
<220> FEATURE:
<223> OTHER INFORMATION: Description of Artificial Sequence:
      Synthetic Peptide

<400> SEQUENCE: 3

Gly Arg Gly Asp Ser Pro
1               5

<210> SEQ ID NO 4
<211> LENGTH: 7
<212> TYPE: PRT
<213> ORGANISM: Artificial
<220> FEATURE:
<223> OTHER INFORMATION: Description of Artificial Sequence:
      Synthetic Peptide

<400> SEQUENCE: 4

Glu Gly Thr Lys Pro Pro Arg
1               5

<210> SEQ ID NO 5
<211> LENGTH: 6
<212> TYPE: PRT
<213> ORGANISM: Artificial
<220> FEATURE:
<223> OTHER INFORMATION: Description of Artificial Sequence:
      Synthetic Peptide

<400> SEQUENCE: 5

Gly Thr Lys Pro Pro Arg
1               5
```

```
<210> SEQ ID NO 6
<211> LENGTH: 7
<212> TYPE: PRT
<213> ORGANISM: Artificial
<220> FEATURE:
<223> OTHER INFORMATION: Description of Artificial Sequence:
      Synthetic Peptide

<400> SEQUENCE: 6

Cys Thr Lys Pro Pro Arg Cys
1               5

<210> SEQ ID NO 7
<211> LENGTH: 12
<212> TYPE: PRT
<213> ORGANISM: Artificial
<220> FEATURE:
<223> OTHER INFORMATION: Description of Artificial Sequence:
      Synthetic Peptide

<400> SEQUENCE: 7

Thr Lys Pro Pro Arg Lys Arg Pro Pro Lys Thr Gly
1               5                   10

<210> SEQ ID NO 8
<211> LENGTH: 24
<212> TYPE: PRT
<213> ORGANISM: Artificial
<220> FEATURE:
<223> OTHER INFORMATION: Description of Artificial Sequence:
      Synthetic Peptide

<400> SEQUENCE: 8

Thr Lys Pro Pro Arg Lys Arg Pro Pro Lys Thr Lys Lys Arg Pro Pro
1               5                   10                  15

Lys Thr Thr Lys Pro Pro Arg Gly
            20

<210> SEQ ID NO 9
<211> LENGTH: 20
<212> TYPE: PRT
<213> ORGANISM: Artificial
<220> FEATURE:
<223> OTHER INFORMATION: Description of Artificial Sequence:
      Synthetic Peptide

<400> SEQUENCE: 9

Thr Lys Pro Pro Arg Thr Lys Pro Pro Arg Thr Lys Pro Pro Arg Thr
1               5                   10                  15

Lys Pro Pro Arg
            20

<210> SEQ ID NO 10
<211> LENGTH: 10
<212> TYPE: PRT
<213> ORGANISM: Artificial
<220> FEATURE:
<223> OTHER INFORMATION: Description of Artificial Sequence:
      Synthetic Peptide

<400> SEQUENCE: 10

Thr Lys Pro Pro Arg Thr Lys Pro Pro Arg
1               5                   10

<210> SEQ ID NO 11
```

-continued

<211> LENGTH: 8
<212> TYPE: PRT
<213> ORGANISM: Artificial
<220> FEATURE:
<223> OTHER INFORMATION: Description of Artificial Sequence:
Synthetic Peptide

<400> SEQUENCE: 11

Thr Pro Ala Thr Ser Val Arg Gly
1 5

<210> SEQ ID NO 12
<211> LENGTH: 4
<212> TYPE: PRT
<213> ORGANISM: Artificial
<220> FEATURE:
<223> OTHER INFORMATION: Description of Artificial Sequence:
Synthetic Peptide

<400> SEQUENCE: 12

Lys Pro Pro Arg
1

<210> SEQ ID NO 13
<211> LENGTH: 12
<212> TYPE: PRT
<213> ORGANISM: Artificial
<220> FEATURE:
<223> OTHER INFORMATION: Description of Artificial Sequence:
Synthetic Peptide

<400> SEQUENCE: 13

Gly Thr Lys Pro Pro Arg Gly Thr Lys Pro Pro Arg
1 5 10

COMPOUNDS FOR TARGETING ENDOTHELIAL CELLS, COMPOSITIONS CONTAINING THE SAME AND METHODS FOR THEIR USE

This application is a divisional of U.S. application Ser. No. 09/871,974, filed Jun. 4, 2001, which is a continuation-in-part of U.S. application Ser. No. 09/585,364, filed Jun. 2, 2000, now abandoned, all of which are hereby incorporated by reference in their entirety.

FIELD OF THE INVENTION

The present invention relates to compounds useful for targeting endothelial cells or cells that express markers in common with endothelial cells, including certain tumor cells, compositions containing the same, uses thereof and methods for screening them. More particularly the present invention provides novel compounds, and compositions containing the same which may be selectively targeted to endothelial cells, or cells expressing markers in common with endothelial cells accessible to the compositions after parenteral or topical administration, of humans and animals, in vivo and in vitro, the compounds and compositions of the invention may also include a detectable moiety which can be detected by any of the imaging modalities. The compositions of the invention may also include a moiety which is capable of providing a therapeutic or radiotherapeutic effect such as, for example a metal chelating group complexed to a metal ion or a bioactive agent. The compounds of the invention may be used in drug delivery and gene therapy applications. Also provided are methods for using the compounds and compositions of the invention as well as kits containing the same.

BACKGROUND OF THE INVENTION

A naturally occurring tetrapeptide TKPR (tuftsin, (SEQ ID NO:1) CAS RN=9063-57-4), L-threonyl-L-lysyl-L-prolyl-L-Arginine (SEQ ID NO: 1)

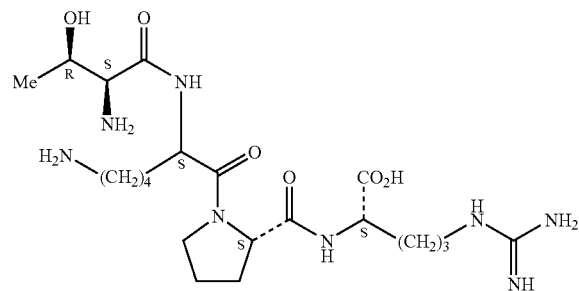

was discovered to stimulate phagocytosis by binding to receptors expressed on the outer surface of neutrophils and macrophages. Phagocytosis constitutes a major line of defense for a host against bacterial infections. Therefore, as a stimulator of phagocytosis, tuftsin would be expected to be a good peptide for imaging sites of infectious inflammation. However studies show that tuftsin labelled with a radionuclide metal undesirably accumulates in non-target tissues.

An alternative approach for imaging infection or inflammation based on the use of a radiolabeled tuftsin receptor antagonist has been disclosed by Pollak A., et al, U.S. Pat. Nos. 5,480,970, 5,659,041, 5,662,885, 5,569,745 and 5,679,642. These patents disclose the use of Tc-99m chelate conjugates of the tuftsin receptor antagonist (see for a review: Nishioka K. et al., Curr. Med. Chem., 1996, 153-66), TKPPR (SEQ ID NO:2), (CAS RN=41961-58-4; or, according to IUPAC nomenclature, L-Arginine, L-threonyl-L-lysyl-L-prolyl-L-prolyl, which has the following structure:

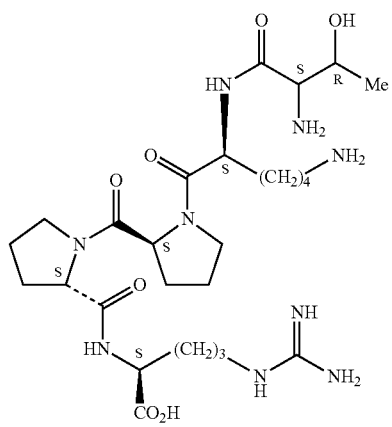

for imaging infection or inflammation. These patents disclose, as chelators, diamidethiols ($N_2S_2$) and triamidethiols ($N_3S$). The chelator may be attached to the tuftsin antagonist via a linking group.

Endothelial cells may be defined as an aggregate of cells and/or tissue which may be normal and/or diseased and which may comprise a single layer of flattened transparent endothelial cells that may be joined edge to edge or in an overlapping fashion to form a membrane. Endothelial cells may be found on the free surfaces of the serous membranes, as part of the lining membrane of the heart, blood vessels, and lymphatics, on the surface of the brain and spinal cord, and in the anterior chamber of the eye. Endothelium originates from the embryonic mesoblast and is found associated with heart tissue, including infarcted heart tissue, the cardiovasculature, the peripheral vasculature, such as arteries, veins, and capillaries (the location of which is noted as peripheral to the heart), and the region surrounding atherosclerotic plaques. Additionally, cells that express markers in common with endothelial cells, especially those in contact with the circulation, may also be considered as important targets of the present invention. For instance, melanoma cells that have been observed forming vascular channels and expressing endothelial cell markers as described in A. J. Maniotis et al. (Am. J. Path., 155, 3, 739-752, 1999 and in Science, 285, 5433, 1475, 1999) may be important targets of diagnosis and/or therapy provided by the present invention.

The use of echocardiography for the diagnosis of cardiovascular diseases has generally been limited to indirect methods that involve the detection and quantitation of abnormalities in the wall motion of the heart. Echocardiography has also been used in connection with methods for detecting pathologies of the heart to identify cardiac masses, emboli, thrombi, vegetative lesions (endocarditis), myxomas, and other lesions.

Accordingly, there is a need for improved imaging techniques, including improved contrast agents that are capable of providing medically useful images of the vasculature and vascular-related organs. The imaging techniques, as used herein, include X-ray Imaging, Magnetic Resonance Imaging, Light Imaging, Scintigraphy, and Ultrasound Echograpy.

In particular, as regards ultrasound echography (ultrasound), the quality of images produced from ultrasound has significantly improved in recent years. New imaging methods, especially dedicated or related to contrast agents have been developed, such as, Native Tissue Harmonic Imaging, $2^{nd}$ Harmonic Imaging, Pulse Inversion Imaging, Acoustically Stimulated Emission (ASE) etc. Nevertheless, further improvements are needed, particularly with respect to images involving tissues that are well perfused with a vascular blood supply.

Accordingly, there is a need for improved ultrasound techniques, including improved contrast agents that are capable of providing medically useful images of the vasculature and vascular-related organs.

The compounds of the present invention may also be useful in the field of angiogenesis. One of ordinary skill will appreciate that a supply of blood vessels is required for tumors to grow beyond a few millimeters in diameter and to metastasize, and that the process by which the blood is provided is generally referred to as angiogenesis. In this process, a vascular supply is developed from existing vasculature for the growth, maturation, and maintenance of tissue. Angiogenesis is a complex multistep process, which involves the endothelial cells of the lumen of blood vessels. Endothelial cells contain all the information necessary to proliferate and migrate to form tubes, branches, and capillary networks.

Targeting angiogenic endothelial cells may be achieved by attaching ligands which will selectively bind to molecules which are upregulated in, on, or near these cells. Such molecules include vascular endothelial growth factor (VEGF) receptors such as Flt-1 (also call VEGFR-1), KDR/Flk-1 (also called VEGFR-2) and NP-1 (also called NRP-1 or neuropilin-1), the $\alpha_v\beta_3$ and $\alpha_v\beta_5$ integrins, matrix metalloproteinases, and certain extracellular matrix proteins and fragments thereof VEGF receptors such as NP-1 or KDR are especially attractive targets. VEGF regulates embryonic vasculogenesis as well as physiological and tumor angiogenesis. Mature VEGF is a homodimer in which the monomers are linked "head to tail" by disulfide bridges. A number of VEGF isoforms are produced by alternative splicing from a single gene containing 8 exons. $VEGF_{121}$ and $VEGF_{165}$ (containing 121 and 165 amino acids respectively) are the most abundant isoforms. These two VEGF isoforms differ in biological activity. For example, $VEGF_{165}$ is the stronger endothelial mitogen and binds to heparin, while $VEGF_{121}$ does not.

The VEGF receptor KDR is one of two VEGF receptor tyrosine kinases (the other being Flt-1) associated primarily with endothelial cells. KDR is present in low amounts in normal mature vessels, but is strongly upregulated at sites of angiogenesis, including angiogenesis induced by hypoxia, inflammation, and cancer. The main site of KDR expression is endothelial cells, but hematopoietic stem cells, megakaryocytes, and retinal progenitor cells also reportedly express it. In addition, some tumor cell lines may express KDR as well NP-1 is a transmembrane glycoprotein expressed in developing nervous, cardiovascular and skeletal systems as well as in adult endothelial cells, tumor cells and a variety of tissues including placenta, heart, lung, liver, kidney, pancreas, bone marrow stromal cells, osteoblasts and keratinocytes. NP-1 was first identified as being involved in neuronal cell guidance and axonal growth. However, more recently NP-1 was identified as also being a receptor for $VEGF_{165}$ (and VEGF-B, VEGF-E). Like KDR, NP-1 is strongly upregulated at sites of angiogenesis. NP-1 is a mediator of angiogenesis, particularly in tumors such as breast and prostate carcinoma and melanoma. *Cell* Vol. 92; 735-74 (1998) Indeed, unlike KDR, NP-1 is abundantly expressed by tumor cells both in vitro and in vivo. Thus, $VEGF_{165}$ binding to tumor cells is mainly due to NP-1. It has been reported that NP-1 expression in tumors resulted in enlarged tumors associated with substantially increased tumor angiogenesis. Further, it has been suggested that NP-1 retains tumor VEGF and prevents its diffusion out of tumor cells. Miao et al "Neuropilin-1 expression by tumor cells promotes tumor angiogenesis and progression" FASEB J. Vol 14, December 2000.

Thus, molecules specific for VEGF receptors like KDR or, more preferably NP-1, should be valuable in diagnosing, imaging and treating angiogenesis.

Angiogenesis is not only involved in cancer development. Many diseases or conditions affecting different physiological systems include angiogenesis. These include: arthritis and atherosclerotic plaques, which may particularly affect bone and ligaments, diabetic retinopathy, neovascular glaucoma, trachoma and corneal graft neovascularization, which may affect the eye, psoriasis, scleroderma, hemangioma and hypertrophic scarring, which may particularly affect the skin, vascular adhesions and angiofibroma, which may particularly affect the blood system. Therefore, anti-angiogenic factors that work by binding to the afore-mentioned receptors could find a use in the treatment or diagnosis of these diseases and tissues or organs, as well as in cancer therapy and diagnosis.

There is therefore a need for an agent which permits visualization by any of the imaging modalities above cited of endothelial cells, and particularly proliferating and or migrating endothelial cells at sites of angiogenesis. There is a further need for a compound that destroys proliferating endothelial cells at sites of angiogenesis thereby starving the tumor by preventing blood from reaching the tumor or for the treatment of inappropriate angiogenesis in general.

SUMMARY OF THE INVENTION

It has now been surprisingly discovered that monomers, multimers or polymers of TKPPR (SEQ ID NO: 2), or analogous peptides, may be used to target endothelial cells, or cells that express markers in common with endothelial cells (including certain tumor cells). Specifically, monomers, multimers or polymers of TKPPR (SEQ ID NO: 2) or its analogues have been found to target endothelial and other cells by binding to the VEGF binding receptor NP-1. The present invention provides, therefore, new diagnostic and/or therapeutically active agents and methods of their use. Specifically, compounds of the present invention are diagnostic, therapeutic or radiotherapeutic compositions useful for visualization, therapy or radiotherapy of endothelial cells, tumor cells or other cells that express NP-1, such as certain types of tumor cells. In particular, the compound of the present invention may be used for visualization, therapy or radiotherapy of angiogenic tissues or organs.

These compositions comprise a monomer, multimer or polymer of TKPPR (SEQ ID NO: 2) (or an analogue of TKPPR (SEQ ID NO: 2) which specifically binds to NP-1, endothelial cells, tumor cells or cells that express NP-1) and a pharmaceutically acceptable carrier. The invention also includes diagnostic, therapeutic or radiotherapeutic compositions in which a monomer, multimer or polymer of TKPPR (SEQ ID NO: 2) (or a TKPPR (SEQ ID NO: 2) analogue) is conjugated, optionally through a linking group, to a substrate.

These compounds are of general formula (I)

A-L-B            (I)

in which

A is a TKPPR (SEQ ID NO: 2) monomer, multimer or polymer or a monomer, multimer or polymer of a TKPPR (SEQ ID NO: 2) analogue, coupled through one or more of the available positions;

L is a linker;

B is a substrate.

The substrate may include, for example, a lipid, a polymer, a detectable moiety or label (including a moiety detectable by ultrasound, MRI, X-ray, scintigraphy, etc); a bioactive agent (a compound that is capable of providing a biological effect, including a therapeutic or cytotoxic effect), a drug delivery vehicle or a gene delivery vehicle. Thus the substrate may include, for example a metal chelating group optionally complexed with a metal useful in scintigraphic imaging or radiotherapy, a lipid or polymer useful in preparing ultrasound contrast agents (such as, for example gas-filled microbubbles or gas-filled microballoons), a therapeutic or drug, or a delivery vehicle for a drug, therapeutic or genetic material.

Particularly preferred are:

the compounds of general formula (Ia) in which in the general formula (I) B corresponds to $B_1$ a lipid able to bind the linker in a covalent or non-covalent manner;

$B_2$ a non-lipid polymer able to bind the linker in a covalent manner;

$B_3$ a polymer useful in the preparation of microballoons; or

Bc a chelating group for a metal, which is optionally complexed to a metal.

Even more preferred are compounds of general formula (Ia) in which A is a multimer of TKPPR (SEQ ID NO: 2) or a TKPPR (SEQ ID NO: 2) analogue, and in especially preferred embodiment A is a tetramer of TKPPR (SEQ ID NO: 2); and B is $B_1$, $B_2$, $B_3$ or Bc as defined above.

The new compounds of the invention may be useful for preparing, in combination with or without a detectable moiety for any of the imaging modalities, novel compositions for imaging and for therapeutic and/or diagnostic applications, where the compounds or compositions of the invention incorporate, for example, a bioactive agent or a detectable moiety, which itself is bioactive (e.g. in Nuclear Medicine).

DETAILED DESCRIPTION OF THE INVENTION

Figure 1:
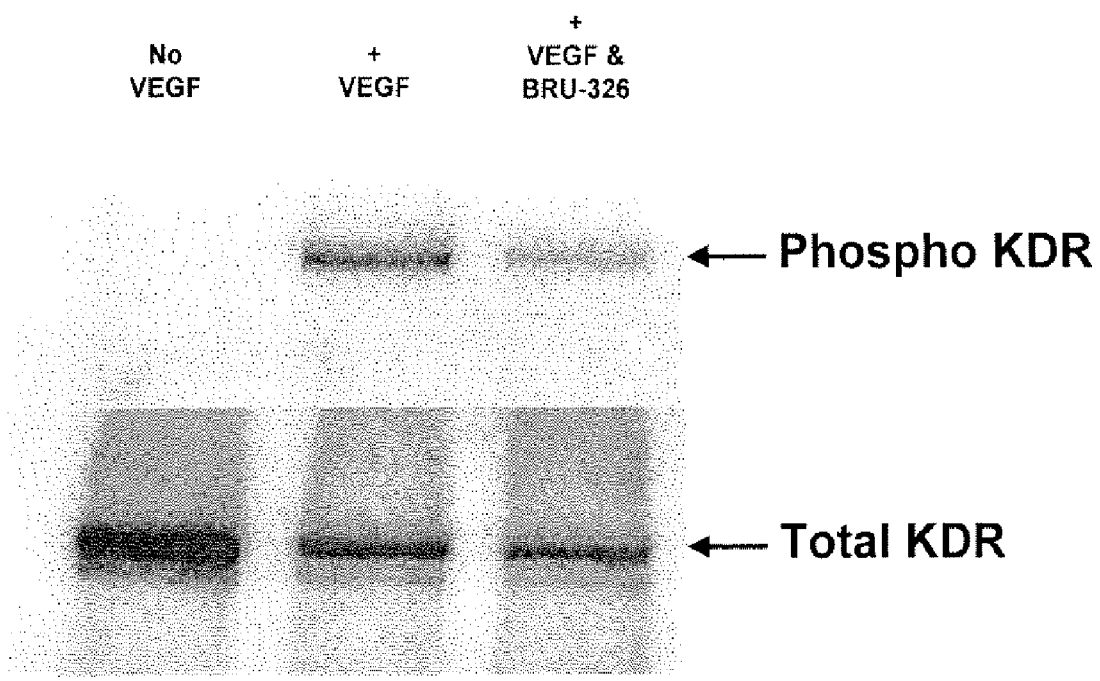
FIG. 1: Activation (phosphorylation) of KDR by VEGF in HUVECs is blocked by a TKPPR (SEQ ID NO: 2) tetramer (BRU-326). After the indicated treatments (no VEGF in lane 1, VEGF in lane 2 and VEGF and BRU-326 in lane 3), KDR was immunoprecipitated and immunoblotted first with anti-phosphotyrosine (top panel) then with anti-KDR (lower panel). Although addition of VEGF alone resulted in a heavily phosphorylated band of KDR on the blot, when the TKPPR (SEQ ID NO: 2) tetramer (BRU-326) was added simultaneously with KDR, only a light band of phosphorylated KDR was visible, consistent with about 60% inhibition of KDR activation by BRU-326.

It has now been surprisingly discovered that TKPPR (SEQ ID NO: 2) and its analogues (as well as monomers, multimers and polymers of TKPPR (SEQ ID NO: 2) and its analogues) bind to the VEGF binding receptor NP-1 on endothelial cells. Further, these monomers, multimers or polymers of TKPPR (SEQ ID NO: 2) and its analogues are able to compete with VEGF in binding to endothelial cells. As the binding of VEGF to endothelial cells is necessary for angiogenesis, compounds of the invention and, in particular, compounds comprising a TKPPR (SEQ ID NO: 2) tetramer, inhibit VEGF-induced angiogenesis. Thus, the compounds and compositions of the present invention can be useful for therapeutic applications without requiring the incorporation of other bioactive substances. Specifically, it has been discovered that peptides or pharmaceutically acceptable salts of peptides having the formula (TKPPR)n            (SEQ ID NO: 2)

where n is 1 to 30, preferably 1 to 10 or more preferably 4-10, and analogues thereof (e.g peptides which specifically bind to NP-1, endothelial cells or cells that express markers in common with endothelial cells with avidity that is equal to or greater than TKPPR) (SEQ ID NO: 2) bind to NP-1 and cells expressing NP-1 (such as endothelial cells and tumor cells). The peptides of the invention block the binding of VEGF to VEGF receptors on endothelial and tumor cells. By blocking the binding of VEGF to these cells, they prevent the angiogenic activity VEGF causes in these cells. Thus, these peptides may be used as therapeutics in the treatment of cancers and other diseases associated with inappropriate angiogenesis. In a preferred embodiment the peptide is multimer of TKPPR (SEQ ID NO: 2) or a TKPPR (SEQ ID NO: 2) analogue. In a particularly preferred embodiment, the peptide is a TKPPR (SEQ ID NO: 2) tetramer.

The peptides of the inventions may be used in a variety of therapeutic and pharmaceutical applications relating to cancers and other diseases associated with inappropriate angiogenesis (i.e. arthritis and atherosclerotic plaques, which may particularly affect bone and ligaments, diabetic retinopathy, neovascular glaucoma, trachoma and corneal graft neovascularization, which may affect the eye, psoriasis, scleroderma, hemangioma and hypertrophic scarring, which may particularly affect the skin, vascular adhesions and angiofibroma, which may particularly affect the blood system.) The peptides of the invention are generally administered as a pharmaceutical composition comprising compounds of the invention or a physiologically acceptable salt thereof, in association with a pharmaceutically acceptable diluent or carrier. Suitable pharmaceutically acceptable carriers include, but are not limited to sterile water, saline solution, buffered saline (including buffers like phosphate or acetate), alcohol, vegetable oils, polyethylene glycols, gelatin, lactose, amylose, magnesium stearate, talc, silicic acid, viscous paraffin, perfume oil, fatty acid monoglycerides and diglycerides, petroethral fatty acid esters, hydroxynethyl cellulose, polyvinylpyrrolidone etc.

The composition may further comprise conventional excipients: i.e., pharmaceutically acceptable organic or inorganic carrier substances suitable for parenteral, enteral or intranasal application which do not deleteriously react with the active compounds. The pharmaceutical preparations can be sterilized and if desired, mixed with auxiliary agents, e.g. lubricants, preservatives, stabilizers, wetting agents, emulsifiers, salts for influencing osmotic pressure, buffers, colorings, flavorings, and/or aromatic substances and the like which do not deleteriously react with active compounds. The pharmaceutical composition may be prepared by any of the known procedures as described in Remington's Pharmaceutical Sciences, Mack Publishing Co. Eaton, Pa. 16th Ed, 1980.

The pharmaceutical compositions may be in various forms like tablets or solutions and may be administered by various routes including parenterally (including intravenously, intramuscularly, subcutaneously and intraperitoneally) and in certain embodiments, orally or nasally.

For oral administration, particularly suitable are tablets, dragrees or capsules having talc and/or a carbohydrate carrier binder or the like, the carrier preferably being lactose and/or corn starch and/or potato starch. A syrup, elixir or the like can be used wherein a sweetened vehicle is employed. Sustained release compositions can be formulated including those wherein the active component is protected with differentially degradable coatings, e.g., by microencapsulation, multiple coatings, etc.

It will be appreciated that the actually preferred amount of active compounds used will vary according the specific compound being utilized, the particular composition formulated, the mode of application and the particular site of administration. Optimal administration rates for a given protocol of administration can be readily ascertained by those skilled in the art, using conventional dosage determination tests conducted with regard to the foregoing guidelines.

According to the present invention, a "therapeutically effective amount" of a pharmaceutical composition is an amount which is sufficient the desired pharmacological effect.

Generally the dosage required to provide an effective amount of the composition, and which can be adjusted by one of ordinary skill in the art, will vary, depending upon the age, health, physical conditional, sex, weight and extent of disease, of the recipient. Additionally, the dosage may be determined by the frequency of treatment and the nature and scope of the desired effect. Appropriate dosages will be determined by those of ordinary skill in the art, using routine methods. In treating cancer, particularly small cell lung carcinoma (SCLC), cultured cell lines may also be isolated from a patient and tested for dose responsiveness (Trepel et al., *Biochem, Biophys. Res. Commun.* 156:1383 (1988); Mahmoud et al., *Life Sci,* 44:367 (1989)) Typically, the dose range is from 0.001 to $^{125}$ 100 mg of active compound per kilogram body weight. Preferably, the range is from 0.01 to 50 mg. of active substance per kilogram body weight. A preferred composition of the invention is for example, one suitable for oral administration in unit dosage form, for example a tablet or capsule which contains from 1 microgram to 500 mg, more preferably from 10 to 100 mg, of peptide in each unit dose, such the a daily oral dose is from 1 nanogram to 50 milligram per kg of body weight, more preferably from 0.1 to 25 mg/kg, is thereby achieved. Another preferable composition is one suitable for parenteral administration which contains from 0.5 to 100 mg of peptide per ml, more preferably from 1 to 10 mg of peptide per ml of solution, such that a daily parenteral dose of from 1 nanogram to 10 mg per kg of body weight, more preferably from 0.1 to 10 mg/kg, is thereby achieved.

A composition of the invention may also contain, in addition to the peptide of the invention, one of more known bioactive (e.g. therapeutic, cytotoxic) agents, in which are discussed in more detail infra.

Analogues of TKPPR (SEQ ID NO: 2) include molecules that target the NP-1 VEGF binding receptor with avidity that is greater than or equal to TKPPR (SEQ ID NO: 2), as well as muteins, retropeptides and retro-inverso-peptides of TKPPR (SEQ ID NO: 2). One of ordinary skill will appreciate that these analogues may also contain modifications which include substitutions, and/or deletions and/or additions of one or several amino acids, insofar that these modifications do not negatively alter the biological activity of the peptides described herein.

The above-mentioned substitutions may be carried out by replacing one or more amino acids by their synonymous amino acids. Synonymous amino acids within a group are defined as amino acids that have sufficient physicochemical properties to allow substitution between members of a group in order to preserve the biological function of the molecule. Synonymous amino acids as used herein include synthetic derivatives of these amino acids (such as for example the D-forms of amino acids and other synthetic derivatives), and, the D-forms of amino acids and other synthetic derivatives), and may include those listed in the following Table. In the chart and throughout this application amino acids are abbreviated interchangeably either by their three letter or single letter abbreviations, which are well known to the skilled artisan. Thus, for example, T or Thr stands for threonine, K or Lys stands for lysine, P or Pro stands for proline and R or Arg stands for arginine.

| Amino acids | Synonymous groups |
|---|---|
| Arg | Arg, His, Lys, Glu, Gln |
| Pro | Pro, Ala, Thr, Gly, N-methyl Ala, pipecolic acid, azetidine carboxylic acid |
| Thr | Thr, Pro, 3-hydroxy proline, 4-hydroxy proline, Ser, Ala, Gly, His, Gln |
| Lys | Lys, ornithine, Arg, 2-amino ethyl-cysteine, Glu, Gln, His |

Deletions or insertions of amino acids may also be introduced into the defined sequences provided they do not alter the biological functions of said sequences. Preferentially such insertions or deletions should be limited to 1, 2, 3, 4 or 5 amino acids and should not remove or physically disturb or displace amino acids which are critical to the functional conformation.

Muteins of the peptides or polypeptides described herein may have a sequence homologous to the sequence disclosed in the present specification in which amino acid substitutions, deletions, or insertions are present at one or more amino acid positions. Muteins may have a biological activity that is at least 40%, preferably at least 50%, more preferably 60-70%, most preferably 80-90% of the peptides described herein. However, they may also have a biological activity greater than the peptides specifically exemplified, and thus do not necessarily have to be identical to the biological function of the exemplified peptides.

Analogues of TKPPR (SEQ ID NO: 2) also include peptidomimetics or pseudopeptides incorporating changes to the amide bonds of the peptide backbone, including thioamides, methylene amines, and E-olefins. Also peptides based on the structure of TKPPR (SEQ ID NO: 2) or its peptide analogues with amino acids replaced by N-substituted hydrazine carbonyl compounds (also known as aza amino acids) are included in the term analogues as used herein.

In a preferred embodiment of the invention, a TKPPR (SEQ ID NO: 2) targeting molecule, A is conjugated to a substrate and optionally a linker to form conjugated to a substrate and optionally a linker to form the compounds of general formula (Ia), where A is the TKPPR (SEQ ID NO: 2) targeting molecule, comprising the TKPPR (SEQ ID NO: 2) peptide, or its analogues, or a multimer or polymer of TKPPR (SEQ ID NO: 2) or its analogues which can be connected to the linker through one or more of the available functional groups. Preferably, the C- and/or N-terminus of the peptide or peptide analogue are selected for coupling to the linker; however coupling of the linker to an internal amino acid or analogue is an optional embodiment of the present invention.

The peptide A is prepared by techniques generally established in the art of peptide synthesis, such as the classical solution approach (Bodansky, M and Bodansky, A The Practice of Peptide Synthesis, Springer Verlag, Berlin, 1984) or the solid-phase approach (Barany, G., Kneib-Cordonier, N., and Mullen, D. G. Solid Phase Peptide Synthesis: A Silver Anniversary Report., Int. J. Pept. Protein Res. 1987 30, 705-739. Fields, G. B. and Noble, R. L. 1990. Solid phase peptide synthesis utilizing 9-fluorenylmethoxycarbonyl amino acids. Int. J. Pept. Protein Res. 1990 35, 161-214).

Solid-phase synthesis involves, for example, the stepwise addition of amino acid residues, to the growing peptide chain that is linked to an insoluble matrix or support, such as polystyrene. The C-terminal residue of the peptide, is first anchored (Principles and Practice of Solid Phase Peptide Synthesis; Fields, G. B., Tian, Z., and Barany, G. "Principles and Practice of Peptide Synthesis" in Grant, G. A. ed. Synthetic Peptides—A Users Guide Oxford University Press, New York, N.Y. 1992, Chapter 3 pp 104-119) to a commercially available support with its amino group protected with an N-protecting agent such as the t-butyloxycarbonyl group (t-Boc) or a fluorenylmethoxycarbonyl (Fmoc) group and its side-chain, where necessary, protected with a protecting group that is stable to the conditions of the peptide chain extension method (Principles and Practice of Solid Phase Peptide Synthesis Fields, G. B., Tian, Z., and Barany, G. "Principles and Practice of Peptide Synthesis" in Grant, G. A. ed. Synthetic Peptides—A Users Guide Oxford University Press, New York, N.Y. 1992, Chapter 3 pp 81-103). The amino protecting group is removed with suitable deprotecting agents such as TFA in the case of t-Boc or piperidine for Fmoc and the next amino acid residue (with the required N protecting group and its side-chain protecting group, where appropriate) is added with a carbodiimide based coupling agent such as dicyclohexylcarbodiimide (DCC) or diisopropylcarbodiimide (DIC) optionally in the presence of an additive such as HOBt (1-hydroxybenzotriazole) or HOAt (1-hydroxy-7-azabenzotriazole), a uronium salt-based coupling agent such as HBTU (2-(1H-benzotriazol-1-yl)-1,1,3,3-tetramethyluronium hexafluorophosphate or a related derivative such as HATU [(O-7-azabenzotriazol-1-yl)-1,1,3,3-tetramethyluronium hexafluorophosphate] (Carpino, L. A., El-Faham, A., Minor, C. A. and Albericio, F. J. Chem. Soc. Chem. Commun. 1994 201-203) or a phosphonium salt-based coupling agent such as BOP benzotriazol-1-yloxy-tris(dimethylamino)phosphonium hexafluorophosphate or related derivatives such as PyBOP usually in the presence of 1 to 10 equivalents of a tertiary amine base such as N-methylmorpholine, diisopropylethylamine, triethylamine, 2,4,6-trimethylpyridine (collidine) (Principles and Practice of Solid Phase Peptide Synthesis; Fields, G. B., Tian, Z., and Barany, G. "Principles and Practice of Peptide Synthesis" in Grant, G. A. ed. Synthetic Peptides—A Users Guide Oxford University Press, New York, N.Y. 1992, Chapter 3 pp 119-125). Upon formation of the peptide bond, the reagents are washed from the support. After addition of the final residue and any other operations, such as removal of the N-terminal Fmoc group (in the case of Fmoc methodology) or addition of any other required moieties to the resin bound peptide by whatever chemical techniques are employed, the peptide is cleaved from the support with a suitable reagent, such as trifluoroacetic acid (TFA) or hydrogen fluoride (HF).

The classical solution approach is illustrated by Scheme 1, which was used in the present invention as an example of the preparation, of the peptide TKPPR (SEQ ID NO: 2) or more generally for peptide A.

Scheme 1

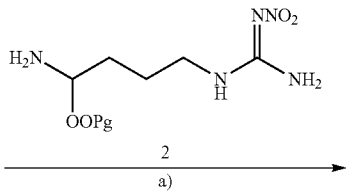

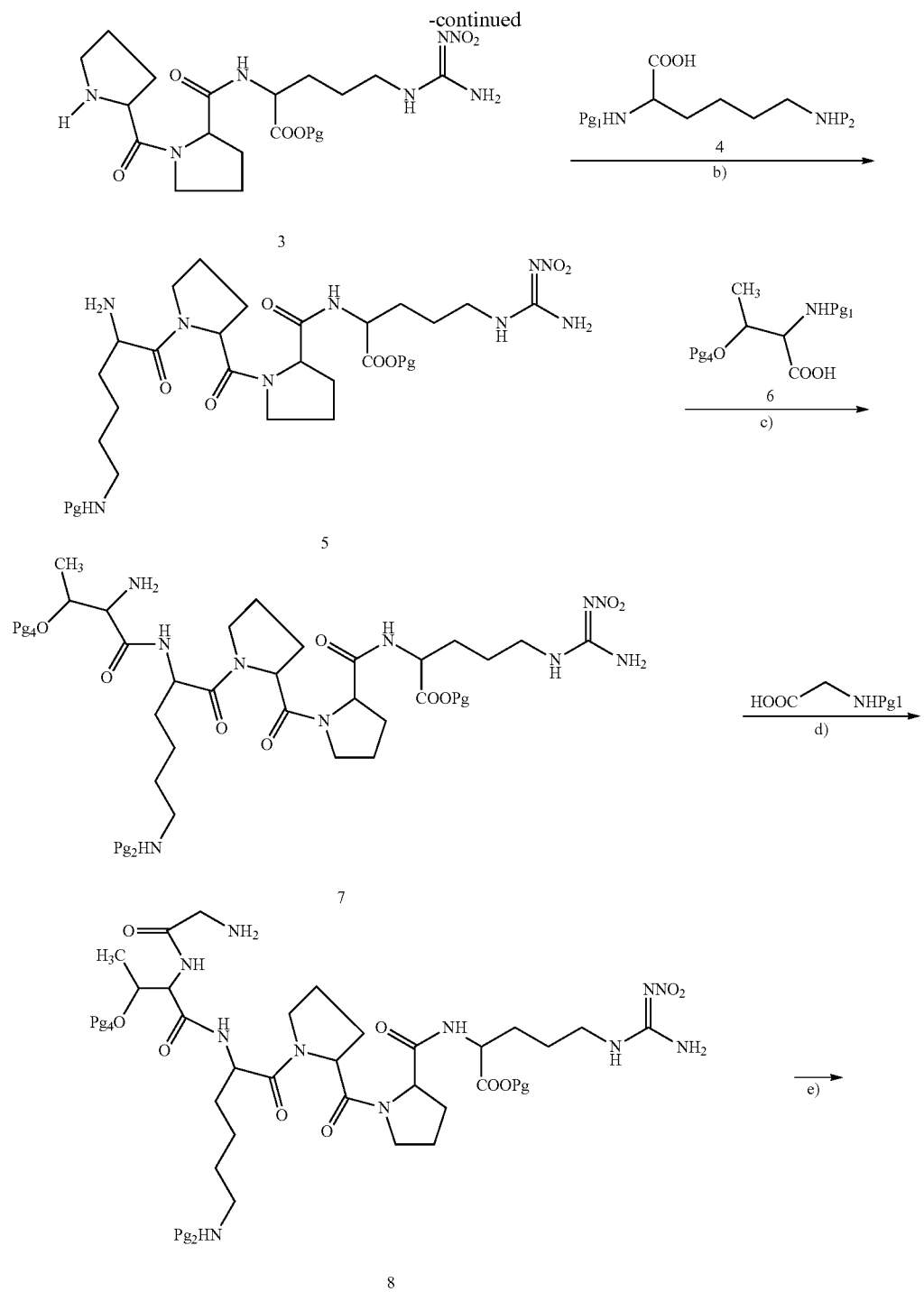

(Pg = protecting group)

The steps a), b), c), and d) are all condensation reactions according to the usual procedures in basic conditions, obtained by adding the appropriate base such as diisopropylethylamine and using a condensing agent, such as DCC, DIC or HATU.

Particularly preferred is HATU ([O-(7-azabenzotriazol-1-yl)1,1,3,3,-tetramethyluronium hexafluorophosphate], which is particularly effective due to the high reaction rates obtained, the low incidence of side reactions and low racemization at the carbon atom of the incoming amino acid.

The last step e) is the condensation in basic conditions with the suitable linker.

The stereochemistry of the peptide will not be affected by the reactions of the process of Scheme 1, so the absolute configuration of the chiral centers is maintained.

Peptide components are coupled to form a conjugate by reacting the available functional groups present in the molecule with an appropriate functional group of the precursor of the linker L.

L can be a bond, an alkyl chain $C_1$-$C_{6000}$, linear or branched, saturated or unsaturated, optionally interrupted or substituted by one or more groups such as: O, S, NR, OR, SR, COR, COOH, COOR, CONHR, CSNHR, C=O, S=O, S(=O)$_2$, P=O(O)$_2$OR, P=O(O)$_2$R, P(O)$_2$(OR)$_2$, halogens, or phenyl groups, optionally substituted by one or more —NHR, —OR, —SR, —COR, —CONHR, —N=C=S, —N=C=O, halogens, in which R is H or an alkyl group $C_1$-$C_4$, linear or branched, optionally substituted by one or more —OH;

such a chain can be interrupted or substituted by one or more cyclic groups $C_3$-$C_9$, saturated or unsaturated, optionally interrupted by one or more O, S or NR; by one or more groups such as: —NHR, —OR, —SR, —COR, —CONHR, or a phenyl group optionally substituted by one or more —NHR, —OR, —SR, —COR, —CONHR, —N=C=S, —N=C=O, halogens.

The most preferred, saturated or unsaturated, cyclic groups, according to the previous definition of L, have the following general formula (III)

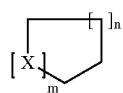
(III)

in which
n can range from 0 to 4;
m can range from 0 to 2;
X can be NH, NR, O, S, SR, S=O and SO$_2$;
where R has the same meanings already defined.

In another preferred embodiment the linker L may be an oligopeptide moiety or retropeptide moiety constituted from 1 to 100 natural or synthetic aminoacids. Particularly preferred are glycyl, glutamyl, aspartyl acid, γ-aminobutyryl, trans-4-aminomethyl-cyclohexane carboxyl.

In a preferred embodiment, L precursors are difunctional PEG (polyethyleneglycol) derivatives.

In a preferred embodiment, L precursors may have the following meaning:

$L_1$ a linker precursor having on at least two locations of the linker the same electrophile E1 or the same nucleophile Nu1;

$L_2$ a linker precursor having an electrophile E1 and on another location of the linker a different electrophile E2;

$L_3$ a linker precursor having a nucleophile Nu1 and on another location of the linker a different nucleophile Nu2;

$L_4$ a linker precursor having one end functionalized with an electrophile E1 and the other with a nucleophile Nu1.

The preferred nucleophiles Nu1/Nu2 of the present invention include —OH, —NH, —NR, —SH, —HN—NH$_2$, —RN—NH$_2$, and —RN—NHR', in which R' and R are independently selected from the definitions for R given above, but for R' is not H.

The preferred electrophiles E1/E2 of the present invention include —COOH, —CH=O (aldehyde), —CR=OR' (ketone), —RN=C=S, —RN=C=O, —S—S-2-pyridyl, —SO$_2$—Y, —CH$_2$C(=O)Y,

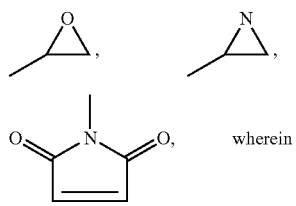 wherein

Y can be selected from the following group:

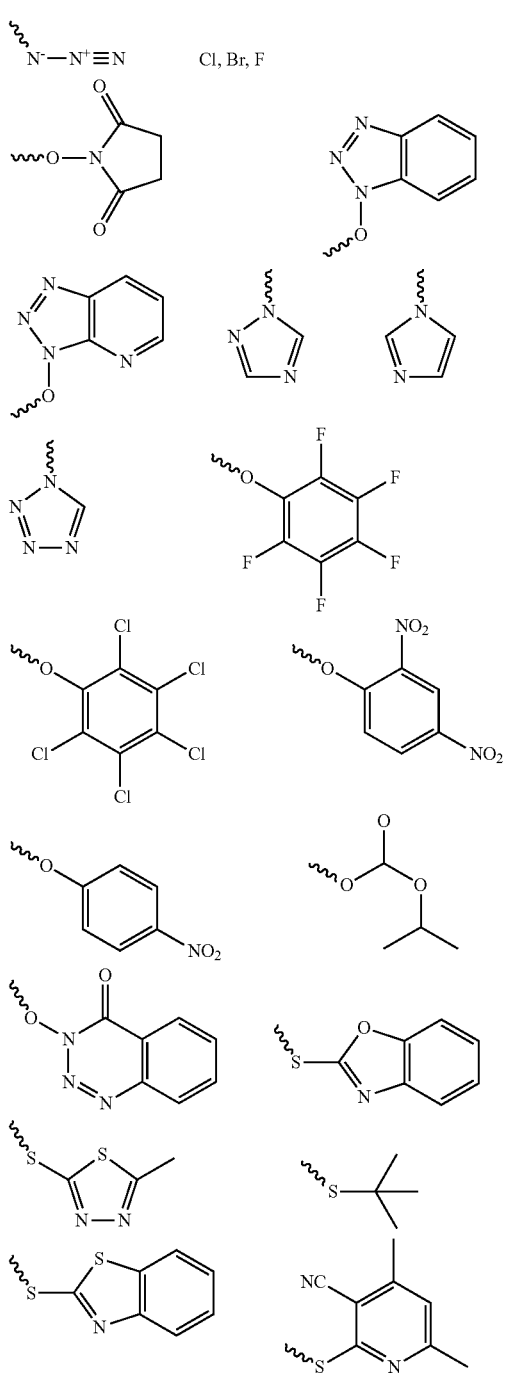

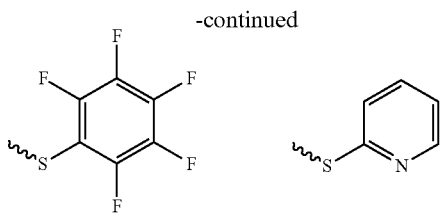

The preferred meanings for $L_1$ are: suitable derivatives of glutaric acid, succinic acid, malonic acid, oxalic acid, PEG derivatized with two $CH_2COOH$, wherein the carboxyl functions, prior to the reactions that are performed to form the bonds between the linker L and A or B respectively, have been converted into C(=O)X moieties, either simultaneously or sequentially, employing, if necessary, any intermediate protection or deprotection steps for the carboxyl group that will be used for the second linker bond forming reaction, Y being selected from the set of moieties described in the chart of Y groups shown above. Such procedures and techniques, for sequential deprotection and utilization of similar or identical functional groups, are well known to those of ordinary skill in the art.

The linker L can alternatively be coupled first to the substrate B and then to the peptide.

Particularly preferred are the compounds of general formula (IIb), able to bind the substrate B A-L (IIb)

prepared according to the general methods above described and where A and L have the meanings discussed herein.

The new compounds of general formula (Ia) may be incorporated in a pharmaceutical composition with different detectable moieties depending on the imaging modality selected.

The incorporation of the targeting moiety may be through a non-covalent association, i.e. a function of a variety of factors, including, for example, the polarity of the involved molecules, the charge (positive or negative), if any, of the involved molecules, the extent of the hydrogen bonding through the molecular network, and the like. Non-covalent bonds are preferably selected from the group consisting of ionic interaction, dipole-dipole interaction, hydrogen bonds, hydrophilic interactions, van der Waal's forces, and any combination thereof. Non-covalent interactions may be employed to bind the compounds of formula (Ia) directly to the surface of various detectable moieties as defined below.

In particular for X-ray Imaging, the new compounds of general formula (I) may be incorporated into X-ray contrast agents, for example, in liposomes encapsulating X-ray iodinated contrast media. Particularly preferred are the liposomes prepared according to the following patents or patent applications: U.S. Pat. No. 5,312,615, U.S. Pat. No. 5,445,810 (WO-A-88/09165) and U.S. Pat. No. 5,393,530 (EP 514523, WO-A-92/10166), U.S. Pat. No. 5,702,722 (WO-A-96/10393), WO-A-96/25955, the entire contents of each of which are hereby incorporated by reference.

For Magnetic Resonance Imaging or for Scintigraphy, the new compounds of general formula (I) may be the targeting moiety for producing new targeted contrast agents, together with the appropriate metal complex, such as those which are known in the fields of radiopharmaceuticals or MRI.

In particular for MRI, the compounds of general formula (I) may be incorporated in lipophilic superparamagnetic contrast agents as those, for example, described in U.S. Pat. No. 5,464,696, U.S. Pat. No. 5,587,199, U.S. Pat. No. 5,910,300, and U.S. Pat. No. 5,545,395 (WO-A-94/04197), the entire contents of each of which are hereby incorporated by reference. Or the new compounds of general formula (I) may be incorporated on the surface of MRI contrast agents based on liposomes or mixed micelles as those described, respectively, in the documents above cited for the X-ray contrast media or in U.S. Pat. No. 5,833,948 (WO97/00087) or in the Ser. application Ser. No. 09/448,289, incorporated herein by reference.

In an analogous way for Scintigraphy, the compounds of general formula (I) may be incorporated in liposomes or mixed micelles comprising suitable complexing agents for radionuclide metals.

Furthermore, in another aspect, the present invention relates to new contrast agents for Scintigraphy or new therapeutic agents for Nuclear Medicine comprising the new compounds of general formula (I), where these compounds include a suitable complexing agent for a radionuclide and may optionally be incorporated in ultrasound contrast agents, as those defined later, in particular microbubbles or microballoons.

In a preferred embodiment where the compounds of the invention are new agents for scintigraphy or new radiotherapeutic compounds, the substrate comprises a metal chelating group, which is optionally complexed to a metal. These compositions comprise compounds of the formula A-L-Bc in which A is a monomer, multimer or polymer of TKPPR (SEQ ID NO: 2) or an analogue of TKPPR (SEQ ID NO: 2), L is an optional linker and Bc is a chelating group for a metal. The metal chelating group, Bc, is a molecule that forms a complex with a metal ion that remains stable (i.e. complexed to the metal chelating group) in vivo. Additionally, the metal chelating group is conjugated either directly to the TKPPR (SEQ ID NO: 2) targeting moiety or to the targeting moiety via a linker. In a preferred embodiment A is a multimer of TKPPR (SEQ ID NO: 2), such as a TKPPR (SEQ ID NO: 2) tetramer.

Metal chelating groups can include monodentate and polydentate chelators [Parker, 1990; Frizberg et al., 1995; Lister-James et al., 1997; Li et al., 1996b; Albert et al., 1991; Pollak et al., 1996; de Jong et al., 1997; Smith et al., 1997]. For example, chelating groups may include tetradentate metal chelators which can be macrocyclic or non macrocyclic, have a combination of four nitrogen and/or sulphur metal-coordinating atoms [Parker et al., 1990; Li et al., 1996b] and are designated as $N_4$, $S_4$, $N_3S$, $N_2S_2$, $NS_3$ chelators. A number of suitable multidentate chelators that have been used to conjugate proteins and receptor-avid molecules. [Frizberg et al., 1995; Lister-James et al., 1997; Li et al., 1996b; Albert et al., 1991; Pollak et al., 1996; de Jong et al., 1997]. These multidentate chelators can also incorporate other metal-coordinating atoms such as oxygen and phosphorous in various combinations. The metal binding complexing moiety can also include "3+1" chelators [Seifert et al., 1998]. For radio diagnostic applications, Oxa-Pn AO ligands, are preferably used. These ligands are discussed in U.S. Pat. Nos. 6,093,382 and 5,608,110, which are incorporated by reference herein in their entirety.

The metal which is optionally complexed with the chelating group can be any suitable metal chosen for a specific therapeutic or diagnostic use, including paramagnetic metals, lanthanides, auger electron-emitting isotopes, positron-emitting isotopes, transition metals, and α, β or γ emitting isotopes. The type of medically useful metal ion depends on the specific medical application. The compounds of this invention that contain a chelating group may be employed as ligands for the formation of radioactive or non-radioactive metal complexes. Metal complexes may be formed by complexing a ligand with a metal having an atomic number 22-31, 39-49, 57-71 or 73-82, especially a radioactive metal, preferably under basic conditions. Preferred metal complexes are those containing a radioactive metal such as $^{99m}$Tc, $^{67}$Ga, $^{68}$Ga, $^{111}$In, $^{88}$Y, $^{90}$Y, $^{105}$Rh, $^{153}$Sm, $^{166}$Ho, $^{165}$Dy, $^{177}$Lu, $^{64}$Cu, $^{97}$Ru, $^{103}$Ru, $^{186}$Re, and $^{188}$Re.

Radionuclides of the elements Tc and Re are particularly applicable for use in diagnostic imaging and radiotherapy. Other radionuclides with diagnostic or therapeutic applications include, but are not limited to $^{62}$Cu, $^{64}$Cu, $^{67}$Cu, $^{97}$Ru, $^{109}$Pd, $^{166}$Ho, $^{198}$Au, $^{149}$Pm, $^{166}$Dy, $^{175}$Yb, $^{117}$Sn, $^{199}$Au, $^{203}$Pb, $^{211}$Pb and $^{212}$Bi.

Technetium complexes are particularly useful for radiodiagnostic applications. The technetium employed is preferably one or more of the radionuclides $^{99m}$Tc, $^{94m}$Tc or $^{96}$Tc-. The preferred radioisotope for medical imaging is $^{99m}$Tc. Its 140 keV γ-photon is ideal for use with widely available gamma cameras. It has a short (6 hour) half-life, which is desirable when considering patient dosimetry. $^{99m}$Tc is readily available at relatively low cost through commercially produced $^{99}$Mo/$^{99m}$Tc generator systems. Preparation of the complexes of this invention where the metal is technetium may be accomplished using technetium in the form of the pertechnetate ion. For $^{99m}$Tc, the pertechnetate ion is preferably obtained from commercially available technetium-99m parent-daughter generators; such technetium is in the +7 oxidation state. The generation of the pertechnetate ion using this type of generator is well known in the art, and is described in more detail in U.S. Pat. Nos. 3,369,121 and 3,920,995. These generators may generally be eluted with saline solution, and the pertechnetate ion obtained as the sodium salt. Pertechnetate may also be prepared from cyclotron-produced radioactive technetium using procedures well known in the art.

These metal complexes find utility as diagnostic and/or therapeutic agents. The choice of metal ion will be determined based on the desired therapeutic or diagnostic application. The metal complexes of the present invention may be administered by any appropriate route such as orally, parenterally (for example, intravenously, intraperitoneally, intramuscularly, or subcutaneously), or by any other suitable method. For example, the complexes of this invention may be administered to a subject by bolus or slow infusion intravenous injection. The amount administered may be selected based on the desired use, such as to produce a diagnostic image of an organ or other site of a subject or a desired radiotherapeutic effect, by methods known in the art. Exemplary dosages are those employing about 30-200 mCi rhenium (for radiotherapy) or about 10-60 mCi technetium (for imaging).

An exemplary method for the formation of a metal complex with ligands disclosed herein is where a complex or salt of the desired metal in the desired oxidation state and containing one or more easily displaceable (i.e. labile) ligands (for example, $H_2O$, halogen (e.g. Cl), $NO_3^-$, or sugars) is mixed with ligand(s) at a pH value suitable for forming the desired complex. The labile ligand(s) are displaced from the metal by the ligand(s) of the present invention to form a metal complex.

Illustrative methods are shown as follows:

$$(Met)(Lig_{lab})4+(Lig_{inv}) \rightarrow (Met)(Lig_{inv})+4(Lig_{lab}) \quad (1)$$

where
Met is a metal in a desired oxidation state;
$Lig_{lab}$ is a labile ligand such as $H_2O$, $Cl^-$, $Br^-$, $F^-$ or $NO_3^-$; and
$Lig_{inv}$ is a ligand comprising a chelating group, an optional linker and a targeting peptide of the invention (e.g. a monomer, multimer or polyner of TKPPR (SEQ ID NO: 2) or a TKPPR (SEQ ID NO: 2) analog).

$$(Met)OCl_4^- +(Lig_{inv}) \rightarrow (Met)O(Lig_{inv})+4Cl^- \quad (2)$$

$$(Met)O_2(Lig_{mono})_4+(Lig_{inv}) \rightarrow (Met)O_2(Lig_{inv})+4(Lig_{mono}) \quad (3)$$

where $Lig_{mono}$ is a monodentate ligand such as pyridine, halide, phosphine or amine.

$$(Met)(Lig_{bi})_2+(Lig_{inv}) \rightarrow (Met)(Lig_{inv})+2(Lig_{bi}) \quad (4)$$

or $$(Met)O(Lig_{bi})_2+(Lig_{inv}) \rightarrow (Met)O(Lig_{inv})+2(Lig_{bi}) \quad (5)$$

where $Lig_{bi}$ is a bidentate ligand such as a sugar, a diol, a bisamine, bipyridine or phosphine, and where, for each equation (1) to (5) above, the appropriate charge balance is employed.

Alternatively, metal complexes may be prepared from a metal in an oxidation state different from that of the desired complex. An exemplary such method is that where either a reducing agent or an oxidizing agent (depending on the oxidation state of the metal used, and the oxidation state of the desired final product) is added to the reaction mixture containing metal to bring the metal to the desired oxidation state. The oxidant or reductant may be used to form an intermediate complex in the desired oxidation state but with labile ligands which are then displaced by a desired chelating ligand of the present invention; or the oxidant or reductant may be added to the reaction mixture containing metal along with the desired ligand to achieve the change to the desired oxidation state and chelation to the desired metal in a single step.

The formation of the $^{99m}$Tc complexes of the invention is achieved by mixing pertechnetate ion in normal saline with the appropriate chelating ligand. An appropriate buffer or physiologically acceptable acid or base may be used to adjust the pH to a range of about 3 to about 9.5, depending on the chelating ligand that is chosen. A source of reducing agent is then added to bring the pertechnetate down to the desired oxidation state for chelation with the ligand. Stannous ion is the preferred reducing agent, and may be introduced in the form of a stannous salt such as stannous chloride, stannous fluoride, stannous tartrate, or stannous citrate. The reaction is preferably run in an aqueous or aqueous/alcohol mixture, at a temperature that may range from room temperature to about 100° C., using a reaction time of about 5 minutes to about 1 hour. The reducing agent should be present at a concentration of 5-50 ug/mL. The ligand should optimally be present in a concentration of 0.1-2 mg/mL. Alternatively, the technetium complexes of this invention can be prepared by ligand exchange. A labile Tc(V) complex can be prepared the reaction of $TcO_4^-$ with a readily exchangeable ligand such as the hydroxycarboxylate ligands glucoheptonate, gluconate, citrate, malate, mannitol, tartrate, or aminecarboxylates such as EDTA or DTPA at a pH value that is appropriate for the exchange ligand in question (usually 5-8). A reducing agent such as the stannous salts described above is added, which causes the formation of a labile reduced complex of Tc with the exchange ligand. This reduced Tc complex is then mixed with the desired chelating ligand at an appropriate pH value, and the labile exchange ligand is replaced by the chelating ligand bearing TKPPR (SEQ ID NO: 2), thus forming the desired technetium complexes of this invention.

Rhenium complexes are particularly useful in radiotherapy applications. The rhenium employed is preferably one of the radionuclides Re-186 or Re-188, or a mixture thereof. Preparation of the complexes of the present invention where the metal is rhenium may be accomplished using rhenium starting materials in the +5 or +7 oxidation state. Examples of compounds in which rhenium is in the Re(VII) state are $NH_4ReO_4$ or $KReO_4$. Re(V) is available as, for example, $[ReOCl_4](NBu_4)$, $[ReOCl_4](AsPh_4)$, $ReOCl_3(PPh_3)_2$ and as $ReO_2(pyridine)_4^+$. (Ph is phenyl; Bu is n-butyl). Other rhenium reagents capable of forming a rhenium complex may also be used.

It is convenient to prepare the complexes of this invention at, or near, the site where they are to be used. A single, or multi-vial kit that contains all of the components needed to prepare the complexes of this invention, other than the Technetium ion, is an integral part of this invention.

A single-vial kit would contain ligand, a source of stannous salt, or other pharmaceutically acceptable reducing agent, and be appropriately buffered with pharmaceutically acceptable acid or base to adjust the pH to a value of about 3 to about 9. It is preferred that the kit contents be in the lyophilized form. Such a single vial kit may optionally contain labile or exchange ligands such as glucoheptonate, gluconate, mannitol, malate, citric or tartaric acid and can also contain reaction modifiers such as diethylenetriamine-pentaacetic acid (DPTA), ethylenediamine tetraacetic acid (EDTA), or $\alpha$, $\beta$, or $\gamma$ cyclodextrin that serve to improve the radiochemical purity and stability of the final product.

A multi-vial kit could contain, in one vial, the ingredients except pertechnetate that are required to form a labile Tc(V) complex as described above. The quantity and type of ligand, buffer pH and amount and type of reducing agent used would depend highly on the nature of the exchange complex to be formed. The proper conditions are well known to those that are skilled in the art. Pertechnetate is added to this vial, and after waiting an appropriate period of time, the contents of this vial are added to a second vial that contains the ligand, as well as buffers appropriate to adjust the pH to its optimal value. After a reaction time of about 5 to 60 minutes, the complexes of the present invention are formed. It is advantageous that the contents of both vials of this multi-vial kit be lyophilized. As above, reaction modifiers, exchange ligands and stabilizers may be present in either or both vials. In addition, bulking agents such as mannitol, that are designed to aid in the freeze-drying process, may be present.

The amount of radiopharmaceutical administered may be selected based on the desired use, such as to produce a diagnostic image of an organ, by methods known in the art. Doses may range from about 2 to 200 mCi, or as limited by the in vivo dosimetry provided by the radiopharmaceuticals.

Furthermore, in another embodiment of the invention, the compounds of general formula (I) may be incorporated in commercially available microparticles, such as fluorescent microspheres to provide compounds and methods for in vitro and in vivo (only for animals) screening of microbubble or microballoon agents of the present invention. This is because derivatized microspheres display the targeting vector on their surface in a manner similar to that expected for microbubbles and microballoons, hence they can act as a model for the latter two types of entities. One example of such microspheres is Fluospheres® (Molecular Probes Corporation, Eugene, Oreg. USA) which possess a carboxylate or amine-modified modified functionality which allows attachment of a peptide via its N-terminus or C-terminus to the bead, using kits provided by the company. The microspheres may be from 0.02 microns to at least 4 microns in diameter and possess fluorescent dye moieties in a variety of colors (blue, yellow-green, Nile Red, orange, red-orange, Crimson Infra-red, or Far red, for example). The microparticles are stable to physical stress as may be encountered in vivo, particularly in the vasculature, whether they are stationary or in transit throughout the entirety of the circulatory system including the periphery, the cardiovascular system and the entirety of the pulmonary vasculature.

In this case the greater stability of the microparticles over that of the microbubbles allows more rigorous assays and assay conditions to be used. This is useful because the bubbles are much more fragile than the beads and are much less able to survive the assay procedures whether automated or not. In addition the bubbles float which makes exposure to the substrate on the bottom or sides of the well/assay system difficult. The beads do not float and are robust so are well-suited to the assays. The microparticles or beads may have a detection system. The detection system may use light or radioactivity.

In a preferred embodiment of the present invention, the new compounds of general formula (I) may be useful for preparing new targeted diagnostic and/or therapeutically active agents useful, for ultrasonic echography, by incorporating them in different ways into ultrasound contrast agents. In a further embodiment, the present invention provides ultrasound contrast agents containing a compound and/or composition of the present invention.

An ultrasound contrast agent of the present invention may be in any convenient form, for example, a contrast agent of the present invention may be in the form of a gas-containing or gas-generating formulation and it comprises a plurality of targeting moieties of formula (I) incorporated in the chemical structure.

Gas microbubbles and other gas-containing materials preferably have an initial average size not exceeding 10 □m (e.g. of 7 □m or less) in order to permit their free passage through the pulmonary system following administration, e.g. by intravenous injection.

In particular, the gas containing contrast agents of the present invention may include suspensions of gas filled microbubbles or suspensions of gas filled microballoons, according to the definition given, for example, in EP 554213, and U.S. Pat. No. 5,413,774.

The term "microbubble" specifically designates gas bubbles, in suspension in a liquid, preferably also containing surfactants or tensides to control the surface properties and the stability of the bubbles. Preferably the microbubble suspension comprises a surfactant or a tenside, such as, for example, a polyoxyethylene-polyoxypropylene block copolymer surfactant such as Pluronic® or a polymer surfactant such as those disclosed in U.S. Pat. No. 5,919,314. More preferably, amphipapathic compounds capable of forming stable films in the presence of water (or an aqueus camer) and gas are used as surfactants in the stabilized microbubbles. Such compounds may include, for example, a film forming lipid or preferably a phospholipid.

The term "microcapsule" or "microballoon" designates preferably air or gas-filled bodies with a material boundary or envelope, i.e. a polymer membrane wall. Both microbubbles and microballoons are useful as ultrasonic contrast agents.

Furthermore, it may be possible to encapsulate a drug in the interior or attach it or incorporate it in the encapsulating walls of the agents of the present invention. Thus the therapeutic compound may be linked to a part of the wall, for example through covalent or ionic bonds, or may be physically mixed into the encapsulating material, particularly if the drug has similar polarity or solubility to the membrane material, so as to prevent it from leaking out of the product before its intended action in the body. The destruction of gas-filled microballoons using external ultrasound is a well-known phenomenon, e.g. as described in WO-A-9325241 or U.S. Pat. No. 5,425,366; the rate of release may be varied depending on the type of therapeutic application by using a specific amount of ultrasound energy from the transducer.

The therapeutic agent may be covalently linked to the encapsulating membrane surface using a suitable linking agent. Thus, for example, one may initially prepare a hydrophobic derivative to which the drug is bonded through a biodegradable or selectively cleavable linker, followed by incorporation of the material in the microballoons. Alternatively, hydrophobic derivatives that do not require processing to liberate an active group may be incorporated directly into the membrane. The active drug may be released by increasing the strength of the ultrasound beam.

In a preferred embodiment, the substrate comprises a lipid, $B_1$, and the compounds of the invention are incorporated into gas-containing microbubbles. The lipids $B_1$, are synthetic or naturally-occurring compounds, and are generally amphipathic and biocompatible, comprising a hydrophilic component and a hydrophobic component. The lipids $B_1$ usable for preparing the gas-containing agents of the present invention include, for example: fatty acids; lysolipids; phospholipids such as: phosphatidylcholine (PC) with both saturated and unsaturated lipids, including phosphatidylcholines such as dioleylphosphatidylcholine; dimyristoylphosphatidylcholine (DMPC), dipentadecanoylphosphatidylcholine, dilauroylphosphatidylcholine (DLPC); dipalmitoylphosphatidylcholine (DPPC); disteraoylphosphatidylcholine (DSPC); and diarachidonylphosphatidylcholine (DAPC); phosphatidylethanolamines (PE), such as dioleylphosphatidylethanolamine, dipalmitoylphosphatidylethanolamine (DPPE) and distearoylphosphatidylethanolamine (DSPE); phosphatidylserines (PS) such as dipalmitoyl phosphatidylserine (DPPS), distearoylphosphatidylserine (DSPS); phosphatidylglycerols (PG), such as dipalmitoylphosphatidylglycerol (DPPG), distearoylphosphatidylglycerol (DSPG); phosphatidylinositol; sphingolipids such as sphingomyelin; glycolipids such as gangliosides GM1 and GM2; glucolipids; sulfatides; glycosphingolipids; phosphatidic acids as dipalmitoylphosphatidic acid (DPPA) and distearoylphosphatidic acid (DSPA); fatty acids such as: palmitic acid; stearic acid; arachidonic acid; oleic acid; lipids bearing polymers, such as chitin, hyaluronic acid, polyvinylpirrolidone or polyethylene glycol (PEG), also referred as "pegylated lipids", with preferred lipids bearing polymers including DPPE-PEG (DPPE-PEG), which refers to the lipid DPPE having a PEG polymer attached thereto, including, for example, DPPE-PEG2000, which refers to DPPE having attached thereto a PEG polymer having a mean average molecular weight of about 2000; lipids bearing sulfonated mono- di-, oligo- or polysaccharides; cholesterol, cholesterol sulfate and cholesterol hemisuccinate; tocopherol hemisuccinate; lipids with ether and ester-linked fatty acids; polymerized lipids (a wide variety of which are well known in the art); diacetyl phosphate; dicetyl phosphate; stearylamine; cardiolipin; phosholipids with short chain fatty acids of about 6 to about 8 carbons in length; synthetic phospholipids with asymmetric acyl chains, such as, for example, one acyl chain of about 6 carbons and another acyl chain of about 12 carbons; ceramides; non-ionic liposomes including niosomes such as polyoxyethylene fatty acid esters, polyoxyethylene fatty alcohols, polyoxyethylene fatty alcohol ethers, polyoxyethylated sorbitan fatty acid esters, glycerol polyethylene glycol ricinoleate, ethoxylated soybean sterols, ethoxylated castor oil, polyoxyethylene-polyoxypropilene polymers, and polyoxyethylene fatty acid stearates; sterol aliphatic acid esters including cholesterol sulfate, cholesterol butyrate, cholesterol iso-butyrate, cholesterol palmitate, cholesterol stearate, lanosterol acetate, ergosterol palmitate, and phytosterol n-butyrate; sterol esters of sugar acids including cholesterol glucoronides, lanosterol glucoronides, 7-dehydrocholesterol glucoronide, ergosterol glucoronide, cholesterol gluconate, lanosterol gluconate, and ergosterol gluconate; esters of sugar acids and alcohols including lauryl glucoronide, stearoyl glucoronide, myristoyl glucoronide, lauryl gluconate, myristoyl gluconate, and stearoyl gluconate; esters of sugars and aliphatic acids including sucrose laurate, fructose laurate, sucrose palmitate, sucrose stearate, glucuronic acid, gluconic acid and polyuronic acid; saponins including sarsasapogenin, smilagenin, hederagenin, oleanolic acid, and digitoxigenin; glycerol dilaurate, glycerol trilaurate, glycerol dipalmitate, glycerol and glycerol esters including glycerol tripalmitate, glycerol distearate, glycerol tristearate, glycerol dimyristate, glycerol trimyristate; long chain alcohols including n-decyl alcohol, lauryl alcohol, myristyl alcohol, cetyl alcohol, and n-octadecyl alcohol; 6-(5-cholesten-3□-yloxy)-1-thio-□-D-galactopyranoside; digalactosyldiglyceride; 6-(5-cholesten-3□-yloxy)hexyl-6-amino-6-deoxy-1-thio-□-D-galactopyranoside; 6-(5-cholesten-3□-yloxy)hexyl-6-amino-6-deoxyl-1-thio-□-D-mannopyranoside; 12-(((7'-diethylaminocoumarin-3-yl)carbonyl)methylamino)octadecanoic acid; N-[12-(((7'-diethylaminocoumarin-3-yl)carbonyl)methylamino)-octadecanoyl]-2-aminopalmitic acid; N-succinyldioleylphosphatidylethanolamine; 1,2-dioleyl-sn-glycerol; 1,2-dipalmitoyl-sn-3-succinylglycerol; 1,3-dipalmitoyl-2-succinylglycerol; 1-hexadecyl-2-palmitoylglycerophosphoethanolamine and palmitoylhomocysteine, and/or combinations thereof.

In a more preferred embodiment, the present invention refers to new compounds of general formula (IIa), $$A\text{-}L\text{-}B_{1a} \qquad (\text{IIa})$$

in which $B_{1a}$ corresponds to a phospholipid moiety of general formula (II),

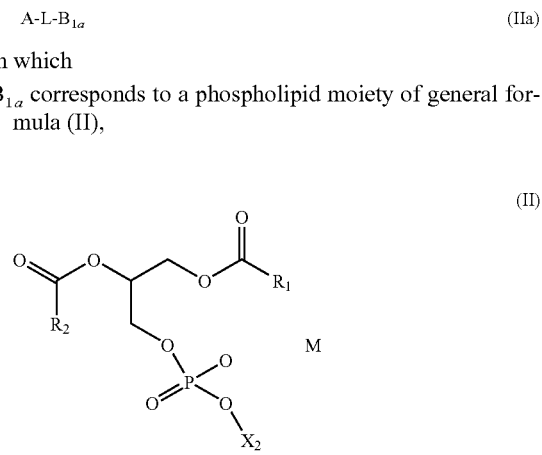

and

M is an alkaline or alkaline-earth metal cation $R_1$ and $R_2$ independently, correspond to linear long chain $C_{12}$-$C_{20}$, saturated or unsaturated, optionally interrupted by C=O, or O $X_2$ can be selected from a group consisting of the following meanings

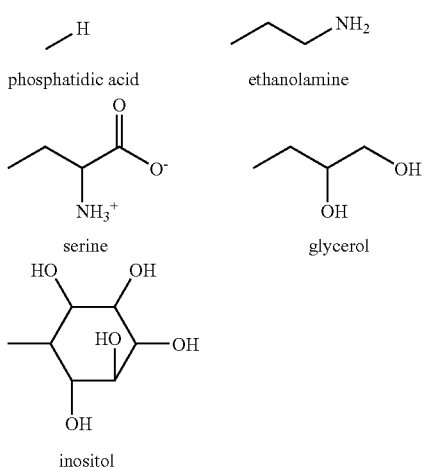

In a preferred embodiment, A is a multimer of TKPPR (SEQ ID NO: 2) such as a TKPPR (SEQ ID NO: 2) tetramer.

Particularly preferred are the phospholipids of formula (II) selected from the following group: dimyristoylphosphatidylethanolamine, dipalmitoylphosphatidylethanolamine, distearoylphosphatidylethanolamine or diarachidoylphosphatidylethanolamine; or dioleylphosphatidylethanolamine or dilinoleylphosphatidylethanolamine, fluorinated analogues of any of the foregoing, mixtures of any of the foregoing, with saturated being preferred.

The phospholipids of general formula (II) can be easily coupled, for example, to the compounds of general formula (IIb), as illustrated in the following Scheme 2, for the preparation of a derivative in which in the general formula (IIa), $B_1$ is dipalmitoylphosphatidylethanolamine and L is constituted by glutaric acid and glycine (see Example 3 of the Experimental section).

Scheme 2

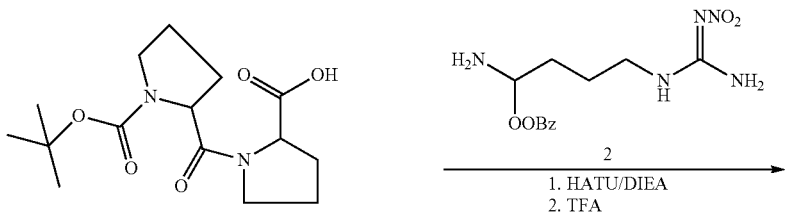

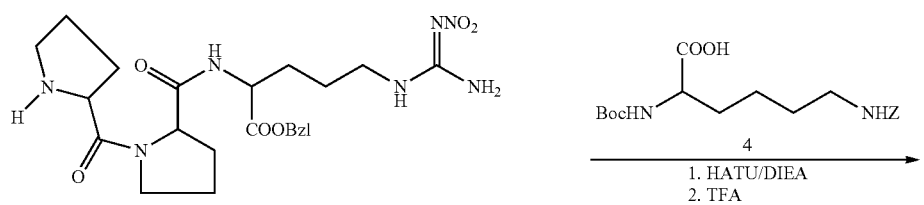

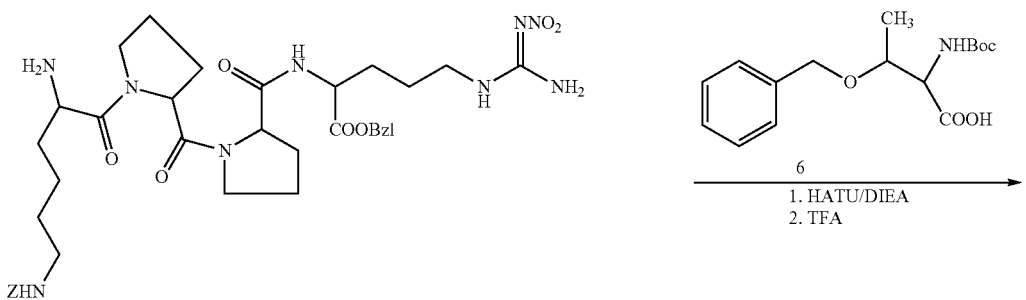

-continued
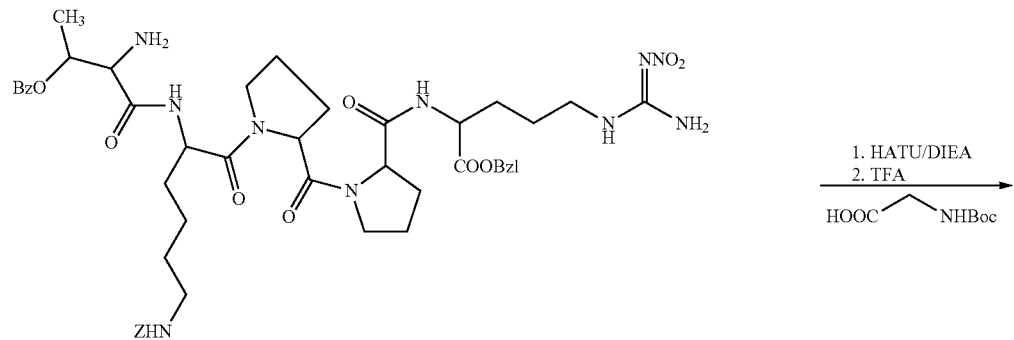
7
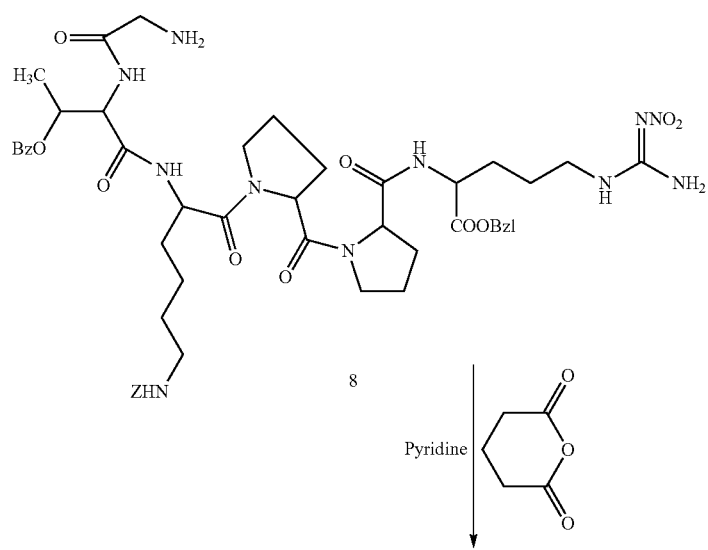
8

-continued
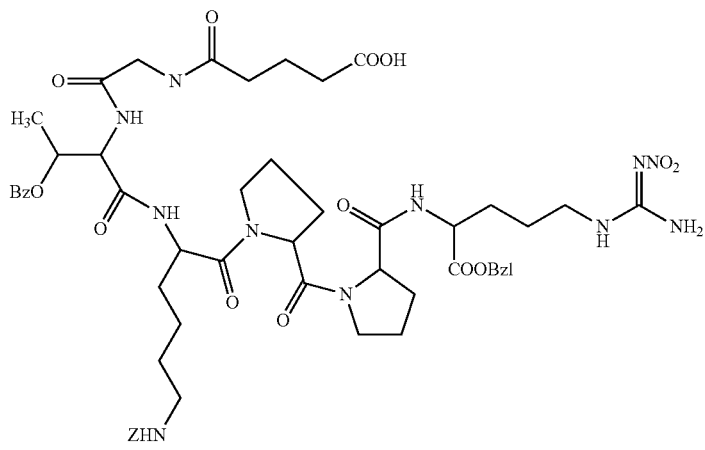
9
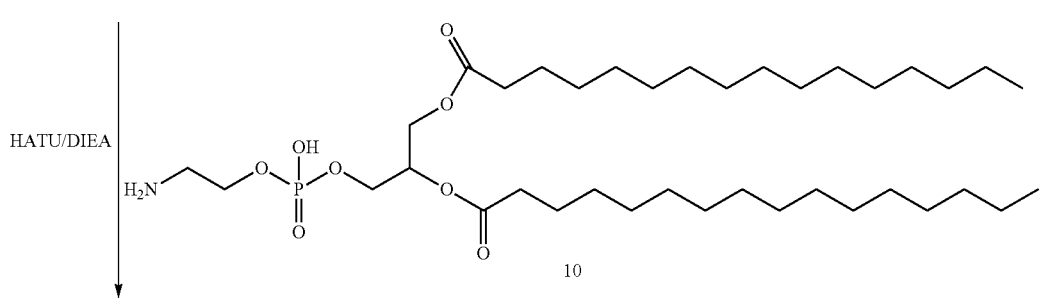
HATU/DIEA
10
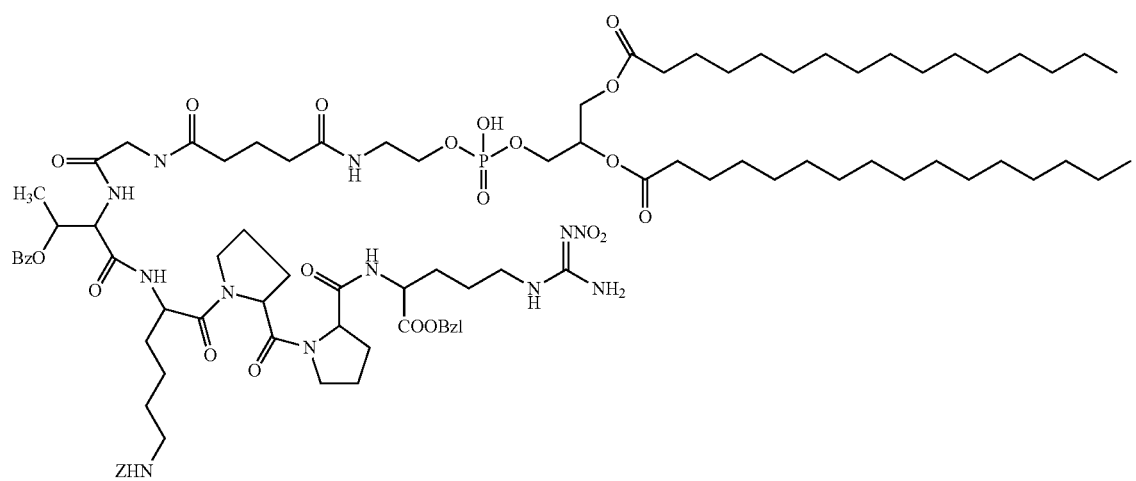
11
H$_2$/Pd
EtOAc, MeOH, AcOH -continued

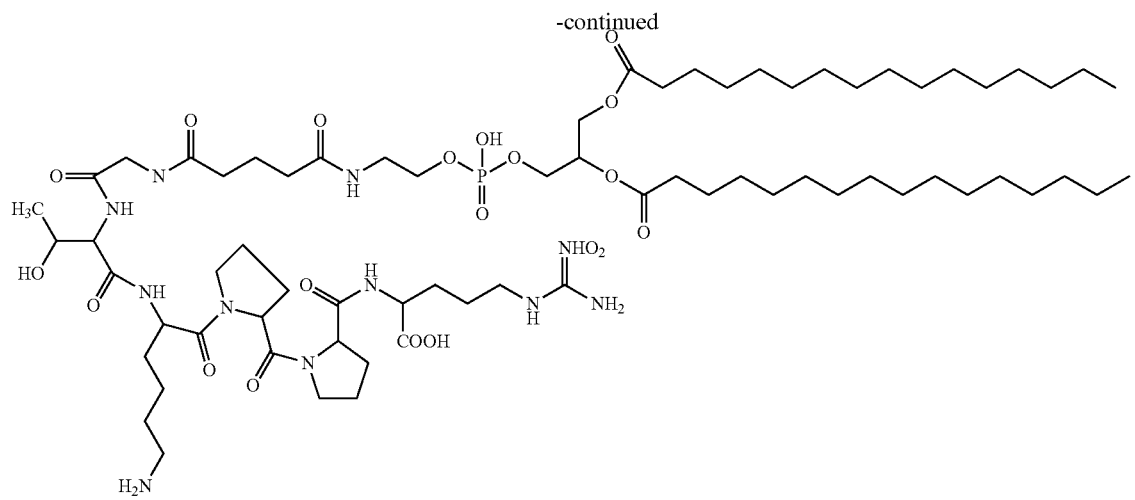

12

Once the new compounds of general formula (IIa) are synthesized, they can be used as film-forming surfactants for producing the preferred gas-filled microbubble contrast agents of the present invention, together with conventional phospolipids.

The conventional phospholipids correspond to those included in the definition previously given for $B_1$ and, for example, include any one of lecithins (i.e. phosphatidylcholines), cardiolipin (CL), sphingomyelins, plasmogens, cerebrosides, etc.

The preferred gas-filled microbubbles of the invention can be prepared by means known in the art, such as, for example, by a method described in any one of the following patents: EP 554213, U.S. Pat. No. 5,413,774, U.S. Pat. No. 5,578,292, EP 744962, EP 682530, U.S. Pat. No. 5,556,610, U.S. Pat. No. 5,846,518, U.S. Pat. No. 6,183,725, EP 474833, U.S. Pat. No. 5,271,928, U.S. Pat. No. 5,380,519, U.S. Pat. No. 5,531,980, U.S. Pat. No. 5,567,414, U.S. Pat. No. 5,658,551, U.S. Pat. No. 5,643,553, U.S. Pat. No. 5,911,972, U.S. Pat. No. 6,110,443, U.S. Pat. No. 6,136,293, EP 619743, U.S. Pat. No. 5,445,813, U.S. Pat. No. 5,597,549, U.S. Pat. No. 5,686,060, U.S. Pat. No. 6,187,288, and U.S. Pat. No. 5,908,610.

The disclosure of all of the above-described documents relating to gas-containing contrast agent formulation are incorporated herein by reference.

As disclosed for the first time in EP 474833 (U.S. Pat. No. 5,271,928, U.S. Pat. No. 5,380,519, U.S. Pat. No. 5,531,980, U.S. Pat. No. 5,567,414, U.S. Pat. No. 5,643,553, U.S. Pat. No. 5,658,551, U.S. Pat. No. 5,911,972, U.S. Pat. No. 6,110,443 and U.S. Pat. No. 6,136,293) an aqueous suspension of microbubbles, which may be used in the present invention, is produced with phospholipid film forming surfactants and, optionally, hydrophilic stabilizers. The total concentration of phospholipids in the preferred embodiment of the invention is between 0.01% and 20% and the concentration of microbubbles is preferably between $10^7$ and $10^{10}$ bubbles/mL. The microbubble suspensions of the present invention preferably remain stable for months.

Preferably the concentration of the bubbles of the present invention is between $10^8$ and $10^9$ bubbles/mL and the concentration of phospholipids used in the microbubbles of the present invention is dependent, in part, on the method of microbubble preparation, the type of phospholipids used for microbubble preparation and the quantity of the peptide or peptide analogue, A, used to achieve stable microbubbles for the ultrasonic contrast agents of the present invention.

The concentration of total phospholipids in a composition of the present invention is preferably in the range of 0.01-10% (w/w) of the total lipid concentration. Most preferred is a range of 0.1-1% (w/w).

In particular the percentage of phospholipids of general formula (IIa) is preferably between 0.1-20% of total lipids (calculated in mol. %). Most preferred is a range of 0.5-5% (w/w).

Other additives known to those of ordinary skill in the art can be added to the foregoing lipids in admixture with the film forming surfactants in the present invention. For instance, polyoxypropylene glycol and polyoxyethylene glycol and similar compounds, as well as various copolymers thereof, fatty acids such as myristic acid, palmitic acid, stearic acid, arachidic acid or their derivatives, ergosterol, phytosterol, sitosterol, lanosterol, tocopherol, propyl gallate, ascorbyl palmitate and butylated hydroxytoluene may be added. The amount of these non-film forming surfactants is usually up to 50% by weight of the total amount of surfactants but preferably between 0 and 30%.

The microbubble suspensions of the present invention may be prepared from the phospholipids of general formula (IIa) in combination with the conventional phospholipids above defined using already known processes such as a freeze-drying or spray-drying solutions of the crude phospholipids in a suitable solvent. Prior to formation of the suspension by dispersion in an aqueous carrier, the freezedried or spray dried phospholipid powders are contacted with air or another gas. When contacted with the aqueous carrier the powdered phospholipids whose structure has been disrupted will form lamellarized or laminarized segments that will stabilise the microbubbles of the gas dispersed therein. Conveniently, the suspensions of the present invention may also be prepared with phospholipids that were lamellarized or laminarized prior to their contacting with air or another gas. Hence, contacting the phospholipids with air or another gas may be carried out when the phospholipids are in a dry powder form or in the form of a dispersion of laminarized phospholipids in the aqueous carrier.

The introduction of air or gas into a dispersion of laminarized phospholipids in an aqueous carrier (such as, for example, a liposome solution) can be effected by the usual means, injection i.e. forcing air or gas through tiny orifices into the liposome solution, or simply dissolving the gas in the solution by applying pressure and then suddenly releasing the pressure. Another way to introduce air or gas into a dispersion of laminarized phospholipids in aqueous carrier is to agitate (high shearing homogenisation) or sonicate the liposome solution in the presence of air or another physiologically acceptable gas. Moreover, one can generate the formation of a gas within the solution of liposomes itself, for instance by a gas releasing chemical reaction, e.g. decomposing a dissolved carbonate or bicarbonate by acid.

When laminarized surfactants are suspended in an aqueous liquid carrier and air or another gas is introduced to provide microbubbles, it is thought that the microbubbles become spontaneously or progressively surrounded and stabilised by a monomolecular layer of surfactant molecules and not a bilayer, as in the case of liposome vesicles. This structural rearrangement of the surfactant molecules can be activated mechanically (agitation) or thermally. The required energy is lower in the presence of non-phospholipid surfactant agents, such as polyoxyethylenepolyoxypropylene block copolymers (e.g. Pluronic® or Synperonic®).

Most preferably, in another approach, non-lamellarized or non-laminarized phospholipids may be obtained by dissolving the phospholipid in an organic solvent and drying the solution without going through the liposome formation stage. In other words, this can be done by dissolving the phospholipids in a suitable organic solvent together with a hydrophilic stabiliser substance e.g. a polymer, like polyvinyl pyrrolidone (PVP), polyvinyl alcohol (PVA), polyethylene glycol (PEG), etc., or a compound soluble both in the organic solvent and water and freeze-drying or spray-drying the solution. Further examples of the hydrophilic stabiliser compounds soluble in water and the organic solvent are malic acid, glycolic acid, maltol and the like. Any suitable organic solvent may be used as long as its boiling point is sufficiently low and its melting point is sufficiently high to facilitate subsequent drying. Typical organic solvents include, for example, dioxane, cyclohexanol, tertiary butanol, tetrachlorodifluoro ethylene ($C_2Cl_4F_2$) or 2-methyl-2-butanol however, 2-methyl-2-butanol and $C_2Cl_4F_2$ are preferred. In this embodiment the criteria used for selection of the hydrophilic stabiliser is its solubility in the organic solvent of choice. The suspensions of microbubbles are produced from such powders using the same steps as with powders of the laminarized phospholipids. Such hydrophilic compounds also aid in homogenising the microbubbles size distribution and enhance stability under storage. Actually making very dilute aqueous solutions (0.0001-0.01% by weight) of freeze-dried phospholipids stabilised with, for instance, a 10:1 to 1000:1 weight ratio of polyethyleneglycol to lipid enables the production of aqueous microbubbles suspensions which are stable, without significant observable change, even when stored for prolonged periods. These are obtained by simple dissolution of the air-stored dried laminarized phospholipids without shaking or any violent agitation.

The freeze-drying technique under reduced pressure is very useful because it permits, restoration of the pressure above the dried powders with any physiologically acceptable gas, whereby after redispersion of the phospholipids processed under such conditions suspensions of microbubbles containing the above gases are obtained.

Other gas containing suspensions useful in the invention include those disclosed in, for example, U.S. Pat. No. 5,798,091 (Trevino et al) and WO 97/29783 (designating the US, also EP 881 915), incorporated herein by reference in their entirety. For example, U.S. Pat. No. 5,798,091 discloses what is stated to be a gas emulsion comprising a plurality of bubbles surrounded by a layer of at least a first and a second surfactant. The first surfactant is a hydrophobic phospholipid or mixture of phospholipids having at least one acyl chain, which comprises at least 10 carbon atoms, and which is at least about 5% w/w of the total surfactant. The second surfactant may or may not also be a phospholipid or mixture of phospholipids, but is more hydrophilic than the phospholipid or combination of phospholipid provided as the first surfactant. Preferred second surfactants may be selected from the group consisting of phospholipids, phosphocholines, lysophospholipids, nonionic surfactants, neutral or anionic surfactants, fluorinated surfactants, which can be neutral or anionic, and combinations of such emulsifying or foaming agents. Some specific examples of surfactants which are useful as the second surfactant include block copolymers of polyoxypropylene and polyoxyethylene (an example of such class of compounds is Pluronic, such as Pluronic F-68), sugar esters, fatty alcohols, aliphatic amine oxides, hyaluronic acid aliphatic esters, hyaluronic acid aliphatic ester salts, dodecyl poly(ethyleneoxy)ethanol, nonylphenoxy poly(ethyleneoxy) ethanol, derivatized starches, hydroxy ethyl starch fatty acid esters, salts of fatty acids, commercial food vegetable starches, dextran fatty acid esters, sorbitol fatty acid esters, gelatin, serum albumins, and combinations thereof. Also contemplated as a second surfactant are polyoxyethylene fatty acids esters, such as polyoxyethylene stearates, polyoxyethylene fatty alcohol ethers, polyoxyethylated sorbitan fatty acid esters, glycerol polyethylene glycol oxystearate, glycerol polyethylene glycol ricinoleate, ethoxylated soybean sterols, ethoxylated castor oils, and the hydrogenated derivatives thereof. In addition, nonionic alkylglucosides such as Tweens®, Spans® and Brijs® may also be used as the second surfactant.

WO 9729783 states that it discloses a contrast agent for use in diagnostic studies comprising a suspension in an injectable aqueous carrier liquid of gas microbubbles stabilised by phospholipid-containing amphiphilic material characterised in that said amphiphilic material consists essentially of phospholipid predominantly comprising molecules with net charges.

WO 9729783 teaches that desirably at least 75%, and preferably substantially all of the phospholipid material in the contrast agents consists of molecules bearing a net overall charge under conditions of preparation and/or use, which charge may be positive or, more preferably, negative. Representative positively charged phospholipids include esters of phosphatidic acids such as dipalmitoylphosphatidic acid or distearoylphosphatidic acid with aminoalcohols such as hydroxyethylenediamine. Examples of negatively charged phospholipids include naturally occurring (e.g. soya bean or egg yolk derived), semisynthetic (e.g. partially or fully hydrogenated) and synthetic phosphatidylserines, phosphatidylglycerols, phosphatidylinositols, phosphatidic acids and cardiolipins. The fatty acyl groups of such phospholipids will typically each contain about 14-22 carbon atoms, for example as in palmitoyl and stearoyl groups. Lyso forms of such charged phospholipids are also useful, the term "lyso" denoting phospholipids containing only one fatty acyl group, this preferably being ester-linked to the 1 position carbon atom of the glyceryl moiety. Such lyso forms of charged phospholipids may advantageously be used in admixture with charged phospholipids containing two fatty acyl groups.

These agents may be prepared as described in U.S. Pat. No. 5,798,091 or WO97/29783. For example, U.S. Pat. No. 5,798,091 teaches that contrast agents may be prepared by first dispersing, in an aqueous solution, a hydrophilic monomer or polymer or combination thereof, a first and a second surfactant, and an inflating agent. As discussed supra, the first surfactant is stated to be a phospholipid or mixture of phospholipids having at least one acyl chain comprising at least 10 carbon atoms and comprising at least about 5% w/w of total surfactant, and the second surfactant is more water-soluble than said first surfactant. The dispersion is then spray dried to evaporate the inflating agent and to create what is described as a dry, hollow, particulate, approximately microspherical material. This dry particulate material is exposed to at least a first gas, and then may be dissolved in an aqueous liquid, thereby forming what is described as an aqueous gas emulsion composition. The patent states that the composition comprises bubbles of the gas surrounded by a layer of the first and second surfactants, and that the stability is independent of liposomes.

These contrast agents may also be prepared according to WO 9729783. WO 9729783 states that these agents may be prepared by a process, comprising the steps of:

i) generating a dispersion of gas microbubbles in an aqueous medium containing what is described as a membrane-forming lipid;

ii) lyophilising the thus-obtained lipid stabilised gas dispersion to yield a dried lipid containing product; and iii) reconstituting the dried product in an injectable aqueous carrier liquid.

It is stated that step (i) may, for example, be effected by subjecting the lipid-containing aqueous medium to any appropriate emulsion-generating technique, for example sonication, shaking, high pressure homogenisation, high speed stirring or high shear mixing, e.g. using a rotorstator homogeniser, in the presence of the selected gas. The aqueous medium may, if desired, contain additives, which serve as viscosity enhancers and/or as solubility aids for the lipid, such as alcohols or polyols, e.g. glycerol and/or propylene glycol.

Any biocompatible gas may be present in the agents of the present invention, the term "gas" as used herein including any substances (including mixtures) substantially in gaseous form at the normal human body temperature. The gas may thus include, for example, air; nitrogen; oxygen; $CO_2$; argon; xenon or krypton, fluorinated gases (including for example, perfluorocarbons, $SF_6$, $SeF_6$) a low molecular weight hydrocarbon (e.g. containing from 1 to 7 carbon atoms) for example an alkane such as methane, ethane, a propane, a butane or a pentane, a cycloalkane such as cyclopropane, cyclobutane or cyclopentene, an alkene such as ethylene, propene, propadiene or a butene, or an alkyne such as acetylene or propyne and/or mixtures thereof.

Fluorinated gases are preferred. Fluorinated gases include materials which contain at least one fluorine atom such as $SF_6$, freons (organic compounds containing one or more carbon atoms and fluorine, i.e. $CF_4$, $C_2F_6$, $C_3F_8$, $C_4F_8$, $C_4F_{10}$, $CBrF_3$, $CCl_2F_2$, $C_2ClF_5$, and $CBrClF_2$) and perfluorocarbons. The term perfluorocarbon refers to compounds containing only carbon and fluorine atoms and includes, in particular, saturated, unsaturated, and cyclic perfluorocarbons. The saturated perfluorocarbons, which are usually preferred, have the formula $C_nF_{n+2}$, where n is from 1 to 12, preferably from 2 to 10, most preferably from 3 to 8 and even more preferably from 3 to 6. Suitable perfluorocarbons include, for example, $CF_4$, $C_2F_6$, $C_3F_8$, $C_4F_8$, $C_4F_{10}$, $C_5F_{12}$, $C_6F_{12}$, $C_7F_{14}$, $C_8F_{18}$, and $C_9F_{20}$. Preferably the gas or gas mixture comprises $SF_6$ or a perfluorocarbon selected from the group consisting of $C_3F_8$ $C_4F_8$, $C_4F_{10}$, $C_5F_{12}$, $C_6F_{12}$, $C_7F_{14}$, $C_8F_{18}$, with $C_4F_{10}$ being particularly preferred.

As cited above the gas can be a mixture of the gases, as defined above. In particular the following combinations are particularly preferred: a mixture of gases (A) and (B) in which, at least one of the gases (B), present in an amount of between 0.5-41% by vol., has a molecular weight greater than 80 daltons and (B) is selected from the group consisting of $SF_6$, $CF_4$, $C_2F_6$, $C_2F_8$, $C_3F_6$, $C_3F_8$, $C_4F_6$, $C_4F_8$, $C_4F_{10}$, $C_5F_{10}$, $C_5F_{12}$ and mixtures thereof and (A) is selected from the group consisting of air, oxygen, nitrogen, carbon dioxide and mixtures thereof the balance of the mixture being gas A.

In certain circumstances it may be desirable to include a precursor to a gaseous substance (e.g. a material that is capable of being converted to a gas in vivo). Preferably the gaseous precursor and the gas it produces are physiologically acceptable. The gaseous precursor may be pH-activated, photo-activated, temperature activated, etc. For example, certain perfluorocarbons may be used as temperature activated gaseous precursors. These perfluorocarbons, such as perfluoropentane, have a liquid/gas phase transition temperature above room temperature (or the temperature at which the agents are produced and/or stored) but below body temperature; thus they undergo a phase shift and reconverted to a gas within the human body.

In practice, all injectable compositions should also be, as far as possible, isotonic with blood. Hence, before injection, small amounts of isotonic agents may also be added to the suspensions of the invention. The isotonic agents are physiological solutions commonly used in medicine and they comprise aqueous saline solution (0.9% NaCl), 2.6% glycerol solution, 5% dextrose solution, etc.

A preferred embodiment of the method of the present invention includes selecting a film forming surfactant and optionally converting it into lamellar form using one of the methods known in the art or disclosed hereinbefore. The surfactant is then contacted with air or another gas and admixed with an aqueous liquid carrier in a closed container whereby a suspension of microbubbles will form. The suspension is allowed to stand for a while and a layer of gas filled microbubbles formed is left to rise to the top of the container. The lower part of the mother liquor is then removed and the supernatant layer of microbubbles washed with an aqueous solution saturated with the gas used in preparation of the microbubbles. This washing can be repeated several times until substantially all unused or free surfactant molecules are removed. Unused or free molecules means all surfactant molecules that do not participate in formation of the stabilising monomolecular layer around the gas microbubbles.

The gas-containing microbubbles formulations containing the targeting moiety of the present invention may be prepared by reconstitution from the dry powder by a suitable physiologically acceptable aqueous carrier, such as buffered or unbuffered physiological saline solution (0.9% aqueous NaCl; buffer 10 mM tris-HCl) or a 5% aqueous dextrose or mannitol solution or a 2.6% aqueous glycerol solution. When the manufacture of injectable therapeutically effective compositions comprising the microbubbles of the invention are contemplated, the microbubbles carrying active ingredients are suspended in the commonly used physiologically acceptable carriers containing known additives and stabilizers.

The microbubbles of the invention may also be used for the delivery of therapeutically active substances, in which case the active substance may be included in the membrane. The compounds of general formula (Ia) or (IIa) are particularly suitable for incorporation into lipidic or lipidic/polymeric membrane material. The amount of lipophilic active material incorporated into the membrane will depend on the nature and the molecular weight; however, very high active substance to lipid ratios are obtained when lipophilic substances are used. Virtually any biologically active substance useful for the therapeutic applications of the present invention can be used with the microbubbles according to the invention. Such substances include but are not limited to, antineoplastic, antiangiogenic, angiogenic compounds, anti-inflammatory compounds, genes, antisense compounds etc.

In another aspect, the present invention relates to agents based on microcapsules/microballoons (microballoons) in which the new compounds of general formula (I) and more particularly (Ia) may be incorporated. As discussed, the term "microballoon" refers to gas filled bodies with a material boundary or envelope. Gas-filled liposomes according to, for example, U.S. Pat. No. 5,123,414 (Unger) also belong to this category and are incorporated herein by reference. More on these different formulation my be found in EP-A-0 324 938 (U.S. Pat. No. 4,844,882, Widder et al.), U.S. Pat. No. 5,711,933 (Bichon et al.), U.S. Pat. No. 4,900,540 (Ryan), U.S. Pat. No. 5,230,882 (Unger),U.S. Pat. No. 5,469,854 (Unger), U.S. Pat. No. 5,585,112 (Unger), U.S. Pat. No. 4,718,433 (Feinstein), U.S. Pat. No. 4,774,958 (Feinstein), WO 9501187 (MBI designating the US), U.S. Pat. No. 5,529,766 (Nycomed), U.S. Pat. No. 5,536,490 (Nycomed), U.S. Pat. No. 5,990,263 (Nycomed), the content of which are incorporated herein by reference.

The preferred microballoons of the present invention have the envelope constituted by $B_3$, a biodegradable physiologically compatible polymer or $B_{3a}$, a biodegradable solid lipid.

The polymers $B_3$ useful for the preparation of the microballoons of the present invention can be selected from the biodegradable physiologically compatible polymers, such as any of those described in any of the following patents: EP 458745, U.S. Pat. No. 5,711,933, U.S. Pat. No. 5,840,275, EP 554213, U.S. Pat. No. 5,413,774 and U.S. Pat. No. 5,578,292, the entire contents of each of which are incorporated herein by reference. In particular, the polymer which constitutes the envelope or bounding membrane can be selected from biodegradable physiologically compatible polymers, such as polysaccharides of low water solubility, polylactides and polyglycolides and their copolymers, copolymers of lactides and lactones such as e-caprolactone, □-valerolactone and polypeptides. The great versatility in the selection of synthetic polymers is another advantage of the present invention since, as with sensitive patients, one may wish to avoid using microballoons made of natural proteins (albumin, gelatin) as in U.S. Pat. No. 4,276,885 or EP-A-324.938. Other suitable polymers include poly(ortho)esters (see for instance U.S. Pat. No. 4,093,709; U.S. Pat. No. 4,131,648; U.S. Pat. No. 4,138,344; U.S. Pat. No. 4,180,646); polylactic and polyglycolic acid and their copolymers, for instance DEXON (see J. Heller, Biomaterials 1 (1980), 51; poly(DL-lactide-co-e-caprolactone), poly(DL-lactide-co-□-valerolactone), poly (DL-lactide-co-□-butyrolactone), polyalkylcyanoacrylates; polyamides, polyhydroxybutyrate; poly-dioxanone; poly-β-aminoketones (Polymer 23 (1982), 1693); polyphosphazenes (Science 193 (1976), 1214); and polyanhydrides. References on biodegradable polymers can be found in R. Langer et al., Macromol. Chem. Phys. C23 (1983), 61-126. Polyaminoacids such as polyglutamic and polyaspartic acids can also be used as well as their derivatives, i.e. partial esters with lower alcohols or glycols. One useful example of such polymers is poly(t.butyl-glutamate). Copolymers with other aminoacids such as methionine, leucine, valine, proline, glycine, alamine, etc. are also possible. Recently, novel derivatives of polyglutamic and polyaspartic acid with controlled biodegradability have been reported (see WO 87/03891; U.S. Pat. No. 4,888,398 and EP-130.935, incorporated here by reference). The lipids $B_{3a}$ useful in the present including are discussed infra.

The microballoons which may be particularly useful in certain applications of the present invention are pressure sustaining microballoons bounded by a soft and elastic membrane which can temporarily deform under variations of pressure and are endowed with enhanced echogenicity and are biodegradable.

The amount of the compounds of general formula (I) that may be incorporated in the microballoon of the present invention may vary depending, for example, on the particular polymer $B_3$ or lipid $B_{3a}$ involved. In certain preferred embodiments, the microballoons composition comprising the targeting moiety may comprise as low as 0.5% mol. of a compound of general formula (I) up to 50% of the total polymer $B_3$ or the lipid $B_{3a}$. The more preferred range is between 5% and 15% of the total.

The microballoons of the present invention are preferably prepared by emulsifying with an emulsifier a hydrophobic phase in an aqueous phase (usually containing viscosity increasing agents as emulsion stabilizers) thus obtaining an oil-in-water type emulsion of droplets of the hydrophobic phase and thereafter adding thereto a membrane forming polymer dissolved in a volatile organic solvent not miscible with the aqueous phase.

Known techniques can be adapted to the preparation of air or gas filled microballoons suited for ultrasonic imaging, according to the present invention, provided that appropriate conditions are found to control sphere size in the desired ranges, balloon-wall permeability or imperviousness and replacement of the encapsulated liquid phase by air or a selected gas. Control of overall sphere size is important to adapt the microballoons for their intended use, i.e. parenteral administration (about 0.5-10 µm average size). Control of balloon-wall permeability is important to ensure that injectable aqueous carrier phase does not infiltrate or infiltrates at a slow enough rate so as not to impair the echographic measurements but is still sufficient to ensure relatively fast after-test biodegradability, i.e. ready metabolization of the suspension by the organism. Also the microporous structure of the microballoons envelope (pores of a few nm to a few hundreds of nm or more for microballoons envelopes of thickness ranging from 50-500 nm) influences their resiliency, i.e. the microspheres can readily accept pressure variations without breaking. The preferred range of pore sizes is about 50-2000 nm.

A preferred method for forming the microballoons with a biodegradable envelope constituted by polymers $B_3$ in mixture with the compounds (Ia) of the present invention, is as follows:

emulsifying a hydrophobic organic phase into a water phase so as to obtain droplets of said hydrophobic phase as an oil-in-water emulsion in the water phase;

adding to the emulsion a solution of a polymer together with the compounds of general formula (I) in a volatile solvent insoluble in the water phase, so that a layer of the polymer will form around the droplets;

evaporating the volatile solvent so that the polymer will deposit by interfacial precipitation around the droplets which then form beads with a core of the hydrophobic phase encapsulated by a membrane of the polymer, the beads being in suspension in the water phase; and subjecting the suspension to reduced pressure under conditions such that the encapsulated hydrophobic phase is removed by evaporation.

Preferably, the hydrophobic phase is selected so that the hydrophobic phase evaporates under reduced pressure substantially simultaneously with the water phase and is replaced by air or gas, whereby dry, free flowing, readily dispersible microballoons are obtained. More preferably, the addition of the polymer and evaporation of the volatile solvent steps can be omitted and the polymer membrane will be formed by interfacial precipitation during the application of a reduced pressure.

One factor which enables control of the permeability of the microballoon membrane is the rate of evaporation of the hydrophobic phase relative to that of water during the application of reduced pressure in the above method, e.g. under conditions of freeze drying which is the case of the embodiment recited below. For instance, if the evaporation is carried out between about −40° C. and 0° C., and hexane is used as the hydrophobic phase, 50:50 DL-lactide/glycolide copolymer being the interfacially deposited polymer, beads with relatively large pores are obtained due to the vapour pressure of the hydrocarbon in the chosen temperature range which is significantly greater than that of water. This creates a condition whereby the pressure difference between the inside and outside of the spheres will tend to increase the size of the pores in the membrane through which the inside material will be evaporated. In contrast, using cyclooctane as the hydrophobic phase (which has a vapor pressure of −17° C., which is the same as that of water) will provide beads with very tiny pores because the difference of pressures between the inside and outside of the spheres during evaporation is minimised.

Depending on the degree of porosity desired, the microballoons of this invention can be made stable in an aqueous carrier from several hours to several months and give reproducible echographic signals for a long period of time. Actually, depending on the polymer selected, the membrane of the microballoons can be made substantially impervious when suspended in carrier liquids of appropriate osmotic properties, i.e. containing solutes in appropriate concentrations. It should be noted that the existence of micropores in the envelope of the microballoons of the present invention appears to be also related with the echographic response, i.e., all other factors being constant, microporous vesicles provide more efficient echographic signal than corresponding non-porous vesicles. Other water-insoluble soluble organic solvents which have a vapour pressure of the same order of magnitude between about −40° C. and 0° C. are convenient as hydrophobic solvents in this invention. These include hydrocarbons such as, for instance, n-octane, cyclooctane, the dimethylcyclohexanes, ethyl-cyclohexane, 2-, 3- and 4-methyl-heptane, 3-ethyl-hexane, toluene, xylene, 2-methyl-2-heptane, 2,2,3,3-tetramethylbutane and the like. Esters, such as propyl and isopropyl butyrate and isobutyrate, butyl-formate and the like, are also convenient in this range. Another advantage of freeze drying is to operate under reduced pressure of a gas instead of air, whereby gas filled microballoons will result. Physiologically acceptable gases are those cited above for the gas-filled microbubbles. Gases with radioactive tracer activity can be contemplated.

As the volatile, water-insoluble solvent to be used for dissolving the polymer to be precipitated interfacially, one may also use halo-compounds such as $CCl_4$, $CH_3Br$, $CH_2Cl_2$, chloroform, perfluorocarbons as defined above, low boiling esters such as methyl, ethyl and propyl acetate as well as lower ethers and ketones of low water solubility. When solvents which are not totally insoluble in water are used, e.g. diethyl-ether, it is advantageous to use, as the aqueous phase, a water solution saturated with said solvent beforehand.

The aqueous phase in which the hydrophobic phase is emulsified as an oil-in-water emulsion preferably contains 1-20% by weight of water-soluble hydrophilic compound(s), such as sugars and polymers as stabilizers, e.g. polyvinyl alcohol (PVA), polyvinyl pyrrolidone (PVP), polyethylene glycol (PEG), gelatin, polyglutamic acid, albumin, and polysaccharides such as starch, dextran, agar, xanthan and the like. Similar aqueous phases can be used as the carrier liquid in which the microballoons are suspended before use.

Part of this water-soluble polymer can remain in the envelope of the microballoons or it can be removed by washing them before subjecting to final evaporation of the encapsulated hydrophobic core phase.

The emulsifiers to be used (0.1-5% by weight) to provide the oil-in-water emulsion of the hydrophobic phase in the aqueous phase include most physiologically acceptable emulsifiers, for instance the phosholipids defined above. Emulsifiers also include surfactants such as free fatty acids, esters of fatty acids with polyoxyalkylene compounds like polyoxypropylene glycol and polyoxyethylene glycol; ethers of fatty alcohols with polyoxyalkylene glycols; esters of fatty acids with polyoxyalkylated sorbitan; soaps; glycerol-polyalkylene stearate; glycerol-polyoxyethylene ricinoleate; homo- and copolymers of polyalkylene glycols; polyethoxylated soya-oil and castor oil as well as hydrogenated derivatives; ethers and esters of sucrose or other carbohydrates with fatty acids, fatty alcohols, these being optionally polyoxyalkylated; mono-, di- and triglycerides of saturated or unsaturated fatty acids; glycerides or soya-oil and sucrose.

Additives can be incorporated into the polymer membrane of the microballoons to modify the physical properties such as dispersibility, elasticity and water permeability. For incorporation in the polymer, the additives can be dissolved in the polymer carrying phase, e.g. the hydrophobic phase to be emulsified in the water phase, whereby they will co-precipitate with the polymer during inter-facial membrane formation.

Useful additives may include compounds which can "hydrophobize" the microballoon membrane in order to decrease water permeability, such as fats, waxes and high molecular-weight hydrocarbons. Additives which improve dispersibility of the microballoons in the injectable liquid-carrier, and may be included in the compositions of the present invention, include amphipathic compounds like the phospholipids. The amphipathic compounds may also increase water permeability and/or the rate of biodegradability.

Additives which increase membrane elasticity, and may be included in the compositions of the present invention, include plasticizers, like isopropyl myristate and the like. Also, very useful additives are constituted by polymers akin to that of the membrane itself but with relatively low molecular weight. For instance when using copolymers of polylactic/polyglycolic type as the membrane forming material, the properties of the membrane can be modified advantageously (enhanced softness and biodegradability) by incorporating, as additives, low molecular weight (1000 to 15,000 Dalton) polyglycolides or polylactides. Also polyethylene glycol of moderate to low $M_w$ (e.g. PEG 2000) is a useful softening additive.

Sterols are preferably used in admixture with the other glycerides and or fatty acids and are selected from cholesterol, phytosterol, lanosterol, ergosterol, etc. and esters of the sterols with the above mentioned fatty acids; however, cholesterol is preferred.

The microballoons of the present invention can also be prepared according to the methods of WO-A-96/15815, and, i.e. on the unexpected finding that a particularly useful solid microcapsule with a mean size from a fraction of micrometer to 1000 micrometers may be obtained when one or more biodegradable solid lipids, at room temperature, are used to encapsulate a core which comprises air or a gas. Useful biodegradable lipids $B_{3a}$ are solid water insoluble mono-, di- or tri-glycerides, fatty acids, fatty acid esters, sterols such as cholesterol, waxes and mixtures thereof. Mono-, di- and tri-glycerides include mainly the mono-, di- and tri-laurin compounds as well as the corresponding-myristin, -palmitin, -stearin, -arachidin and -behenin derivatives. Mono-, di- and tri-myristin, -palmitin -stearin and mixed triglycerides such as dipalmitoylmonooleyl glyceride are particularly useful; however, tripalmitin and tristearin are preferred. When made from fatty acids or mixtures of fatty acids with glycerides and/or sterols, the fatty acids include all, at room temperature solid, fatty acids (preferably saturated) having 12 carbon atoms or more. These fatty acids include, for instance, lauric, arachidic, behenic, palmitic, stearic, sebacic, myristic, cerotinic, melissic and erucic acids, the fatty acid esters. Preferably, the fatty acids and their esters are used in admixture with other glycerides.

A preferred microballoon composition was obtained with triglycerides such as tripalmitin, tristearin or mixtures of the above mentioned triglycerides. Lower yields and microballoons with a slight tendency to agglomeration were obtained when diglycerides were used. The lowest yields of microballoons were obtained with monoglycerides. The degree of hydrophobicity appears to explain the fact that the best microballoons are obtained from the fairly hydrophobic materials and as the hydrophobicity decreases or surface activity increases the quality and the quantity of the microballoons obtained decreases. The greater participation of the more hydrophobic triglyceride (lipid) the better the microballoon yield and the smoother the process of the manufacture.

Optionally, biodegradable water insoluble lipids may be admixed with up to 75% by weight of biodegradable polymers. The amount of biodegradable polymers is limited to 75% by weight, because the biodegradability of the glyceride/polymer mixtures is not a linear function of the composition i.e. the biodegradability does not increase or decrease in direct proportion to the amount of the polymer present in the mixture, but that it is more determined or influenced by the biodegradability of the glycerides than by that of the polymers. This is so only as long as the amount of glycerides is equal to or greater than 25% by wt. as the mixtures containing 25% by wt. or more of the glyceride have biodegradability closer to that of lipids than to that of polymers. However, the mixtures with 75% by wt. or more of the polymer have biodegradability closer to that of pure polymers. This means that the mixtures with less than 25% of glycerides in terms of biodegradability will behave almost like the pure polymers. When, however, the amount of lipids approaches 25% the character of the mixture changes and further increase of the amount of lipids has a greater impact on the biodegradability of the mixture by imposing the lipid biodegradability rate on the polymers, i.e. rendering the mixture more biodegradable than what would or could be expected considering the amount of polymer present. This clearly demonstrates that biodegradability of the mixture is not a simple sum of the individual biodegradabilities but is conditioned by the component present in excess, however in such a way that the influence of the glycerides is predominant. For compositions with more than 75% by weight of the polymer, biodegradability rapidly approaches that of the pure polymer.

The glyceride containing hollow microballoons of the present invention preferably are prepared with an average size between 0.1 µm and 1000 µm by dispersing, in an aqueous carrier phase, a mixture of one or more of the solid constituents of the microcapsule envelope dissolved in an organic solvent, so as to produce an oil-in-water emulsion. The emulsion water phase may contain an effective amount of surfactants which are used to stabilise the emulsion. Surfactants such as (PVA), polyoxyethylene-polyoxypropylene block copolymers, phospholipids such as phosphatidic acid, phosphatidyl choline, phosphatidylethanol amine, phosphatidyl serine, phosphatidyl glycerol, phosphatidyl inositol and mixtures thereof, sorbitan ethers, sorbitan esters, polyoxyethylenesorbitan esters, ethoxylated saturated glycerides and partial fatty acid glycerides or polyglycerides, etc., may be used, but polyoxyethylene-polyoxypropylene block copolymers (e.g. Pluronic®, or Synperonic®) and phospholipids are preferred. The presence of the surfactants is compulsory only if the size of the final product or particle size distribution is important. If the preparation is intended for the parental administration, presence of the surfactant in the water phase is important. Prior to freezing at a temperature below –30° C., a certain amount of redispersing agent is added to the emulsion of tiny droplets of the organic solution in the water phase. The frozen emulsion is then subjected to reduced pressure to effect lyophilisation, i.e. the removal by sublimation of the organic solvent from the droplets and of the water of the carrier phase. Without wishing to be bound by any particular theory, it is postulated that during this relatively slow solvent removal, the membrane constituents migrate outwardly to the periphery of droplets until they arrive to the frozen water boundary where their further motion is impeded causing the formation of a molecularly organized dense deposit at the solvent/ice interface which may acquire a semi-crystalline structure in the area at the junction between the solvent and the ice, i.e. at the solvent to ice interface.

Any convenient redispersing agent may be used; however redispersing agents selected from albumin, gelatine, PVP, PVA, PEG and polyoxyethylene-polyoxypropylene block copolymer are preferred. The redispersing agents which are added to prevent particle agglomeration are particularly useful when the microballoons are in the form of non-coalescent, dry and instantly dispersible powders. Produced for a long storage or from hydrophobic triglyceride materials such as tripalmitin or tristearin, the microballoons preparations of the invention further comprise one or more redispersing agents. Where the microballoons comprise gas filled liposomes, they may be prepared as described in, for example, U.S. Pat. No. 5,123,414, U.S. Pat. No. 5,469,854, U.S. Pat. No. 5,585,112, and WO 9222247 (Unger) (designating the US), incorporated herein by reference in their entirety, and adapted to include the targeting moiety of the invention as discussed herein.

The porosity of the hollow microballoons made according to the invention is usually very low and sometimes the microballoons have no pores at all. It appears that the porosity is a function of the lipid concentration or wall thickness of the microcapsule. When porous, the microballoons of the invention have a pore size in the range of 20 to 2,000 nm.

As already mentioned when the microballoons of the invention are prepared from mixtures of one or more biodegradable water insoluble lipids $B_{3a}$ with biodegradable polymers $B_3$, up to 75% by weight of the polymer may be used. Microballoons of controlled half-life after administration can be customized by adjusting the respective proportions of the lipids $B_{3a}$ and biodegradable polymers $B_3$ during fabrication. The exact amount of the polymer will depend on the application and will be directly related to the degree of biodegradability required. For example, for certain sustained release applications the amount of biodegradable polymer may be anywhere between 30% and 60% by wt. and in some cases up to 75% by weight. However, if the microballoons of the invention are used for echographic imaging, depending on the desired rate of clearance from the body, the amount of biodegradable polymer may be between 1-50% by wt. preferably between 0.5-10% by wt. or as low as 0.1% by wt.

The microballoons used for echography typically having relatively thin walls (e.g. 50-500 nm thick) are particularly advantageous as their biodegradability is very rapid (i.e. the clearance of the lipidic envelopes from the body, occurs within a relatively short period of time).

When microballoons are made from mixtures of one or more water insoluble lipids $B_{3a}$ with a biodegradable polymer $B_3$ as defined previously, however, polylactides and polyglycolides and their copolymers are preferred.

The microballoons of the invention may be used for the delivery of therapeutically active substances, in which case the active substance may be included in the membrane or may be loaded in the core. The compounds of general formula (Ia) or (IIa) are particularly suitable for incorporation into lipidic or lipidic/polymeric membrane material. The amount of lipophilic active material incorporated into the membrane will depend on the nature and the molecular weight; however, very high active substance to lipid ratios are obtained when lipophilic active substances are used. Virtually any biologically active substance useful for the therapeutic applications of the present invention can be used with the microballoons according to the invention. Such substances include but are not limited to, antineoplastic, antiangiogenic, angiogenic compounds, anti-inflammatory compounds, genes, antisense compounds etc.

Experiments have shown that when the microballoons of the invention are used as delivery vehicles for active substances, different effects may be achieved by varying the concentration of the lipid or lipid/polymer mixture in the starting material. It has been established that microballoons with relatively thin walls and a high active substance to lipid or lipid/polymer ratio, i.e. high concentration of the active ingredient, will produce a shock treatment in the surrounding tissue. A particular advantage of the microballoons of the invention comes from the fact that the shock treatment may be customized by varying the ratio or the wall thickness while maintaining the concentration of the active substance at a constant level thus producing a form of sustained release system. The system in turn may be fully adapted to the substance carried, the treatment envisaged and even the physiological condition of the patient.

The present invention provides injectable compositions including a suspension of an effective amount of microballoons in a pharmaceutically acceptable liquid carrier with optional additives known to those of ordinary skill in the art and stabilisers.

Echographic contrast agents are readily produced by suspending the microballoons of the invention in a suitable physiologically acceptable aqueous carrier, such as buffered or unbuffered physiological saline solution (0.9% aqueous NaCl; buffer 10 mM tris-HCl) or a 5% aqueous dextrose or mannitol solution or a 2.6% aqueous glycerol solution. When the manufacture of injectable therapeutically effective compositions comprising the microballoons of the invention are contemplated, the microballoons carrying active ingredients are suspended in the commonly used physiologically acceptable carriers containing known additives and stabilizers.

Other useful gas-containing contrast agent formulations include gas-containing solid systems, for example microparticles (especially aggregates of microparticles) having gas contained therein or otherwise associated therewith (for particles (especially aggregates of microparticles) having gas contained therein or otherwise associated therewith (for example being adsorbed on the surface thereof and/or contained within voids, cavities or pores therein). These contrast agents may be adapted to contain the targeting moiety of the invention as described herein. Methods for the preparation of these agents are as described in EP 0122624 EP 0123235, EP 0365467, U.S. Pat. No. 5,558,857, U.S. Pat. No. 5,607,661, U.S. Pat. No. 5,637,289, U.S. Pat. No. 5,558,856, U.S. Pat. No. 5,137,928, WO 9521631 or WO 9313809, incorporated herein by reference in their entirety. It will be appreciated that the echogenicity of these contrast agents may derive directly from the contained/associated gas and/or from gas (e.g. described herein. Methods for the preparation of these agents are as described in EP 0122624 EP 0123235, EP 0365467, U.S. Pat. No. 5,558,857, U.S. Pat. No. 5,607,661, U.S. Pat. No. 5,637,289, U.S. Pat. No. 5,558,856, U.S. Pat. No. 5,137,928, WO 9521631 or WO 9313809, incorporated herein by reference in their entirety. It will be appreciated that the echogenicity of these contrast agents may derive directly from the contained/associated gas and/or from gas (e.g. microbubbles) liberated from the solid material (e.g. upon dissolution of the microparticulate structure).

In another aspect of the present invention, we have found a new model in vitro and in vivo (only for animals) for the screening of the agents of the present invention: the compounds are attached to polymer beads or other non-lipid polymer materials which are labeled with a detectable label (e.g. a fluorescent dye). Typically, in vitro screening of compounds for binding to a desired site is accomplished by incubating a labeled (radioactive, fluorescent, etc.) form of the compound with an appropriate in vitro model. Such assays developed to measure compound binding have some limitations. First, the sensitivity of the assay is often so low that binding cannot be easily detected or quantitated. Because of this, many screening assays utilize whole cells or membrane fractions from cell lines engineered to overexpress the binding target. If the exact binding target is unknown, or is not easily expressed through genetic methods, this approach is not feasible. Secondly, the assay will usually only detect relatively high-affinity binding events. This means that the opportunity to identify moderately tight-binding compounds, which can then be optimized to improve binding, is lost.

However attaching compounds to beads or other particles can largely overcome the limitations of screening with labeled compounds. A single fluorescently labeled bead, with a diameter attaching compounds to beads or other particles can largely overcome the limitations of screening with labeled compounds. A single fluorescently labeled bead, with a diameter of about 1 micron or greater, can easily be seen using an ordinary fluorescent microscope. For higher throughput screening, fluorescent beads can easily be detected and quantitated on fluorescence microplate readers. Alternatively, easily detectable amounts of radioactivity can be incorporated into the agents of the invention. Assays using such radioactive entities would be more sensitive than those utilizing individually labeled compound molecules.

Another advantage of attaching compounds to beads for screening purposes is that numerous molecules of the compound become attached per bead. The resulting multivalent presentation of the molecule increases the binding avidity of the bead for its target, and allows the detection of compounds that might not be identified by more traditional screening assays, due to a relatively low binding strength of the compound as a single molecule.

Furthermore, access to the targeting moiety on the agents of the invention may be modified because they are presented on the surface of a large entity. Thus the targeting moiety may interact with different targets, when bound to microvesicles or beads, then when as small molecules or individual molecules. Thus another aspect of the invention is the use of easily prepared beads to predict the behavior of similarly derivatized microspheres of about 1 micron or greater, can easily be seen using an ordinary fluorescent microscope. For higher throughput screening, fluorescent beads can easily be detected and quantitated on fluorescence microplate readers. Alternatively, easily detectable amounts of radioactivity can be incorporated into the agents of the invention. Assays using such radioactive entities would be more sensitive than those utilizing individually labeled compound molecules.

Another advantage of attaching compounds to beads for screening purposes is that numerous molecules of the compound become attached per bead. The resulting multivalent presentation of the molecule increases the binding avidity of the bead for its target, and allows the detection of compounds that might not be identified by more traditional screening assays, due to a relatively low binding strength of the compound as a single molecule.

Furthermore, access to the targeting moiety on the agents of the invention may be modified because they are presented on the surface of a large entity. Thus the targeting moiety may interact with different targets, when bound to microvesicles or beads, than when as small molecules or individual molecules. Thus another aspect of the invention is the use of easily prepared beads to predict the behavior of similarly derivatized microspheres.

Thus, the instant invention includes attaching monomers, multimers or polymers of TKPPR (SEQ ID NO: 2), (or a TKPPR (SEQ ID NO: 2) analogue) to beads for use in screening and other assays. In this embodiment, the present invention provides compounds of general formula (Ib)

A-L-B$_2$ (Ib)

in which

B$_2$ is a non-lipid polymer able to bind the linker in a covalent manner, and A and L have the same meanings above defined.

In preferred embodiment of the present invention, B$_2$ corresponds to B$_{2a}$, a polymer which can be used for producing microparticles or beads containing functional groups, such as acid or amino groups, able to bind chemical entities or B$_2$ is the bead itself. Microparticles are generally considered to be spherical or irregular in shape, and to be less than about 50 micrometers in diameter. They may be prepared by several practical methods from a variety of polymerizable monomers, including styrenes, acrylates and unsaturated chlorides, esters, acetates, amides and alcohols. Microparticles can be further modified by coating with one or more secondary polymers to alter the surface properties of the particles.

In a more preferred embodiment of the present invention the bead is a commercially available bead which is derivatizable and may, optionally include a detectable label. The detectable label may preferably be one which generates light or a radioactive signal, such as are known in the art.

Beads labeled with fluorescent dyes, for example, have found use in a wide variety of applications. Fluorescent beads are most commonly used in applications that can benefit from use of monodisperse, chemically inert, biocompatible particles that emit detectable fluorescence and that can bind to a particular substance in the environment. For example, fluorescent particles to which biological molecules have been attached have been used for immunoassays (U.S. Pat. No. 4,808,524 (1989)), for nucleic acid detection and sequencing (Vener, et al. ANALYT. BIOCHEM. 198, 308 (1991); Kremsky, et al., NUCLEIC ACIDS RES. 15, 2891 (1987); Wolf, et al., NUCLEIC ACIDS RES. 15, 2911 (1987)), as labels for cell surface antigens, FLOW CYTOMETRY AND SORTING, ch. 20 (2@nd ed. (1990)), and as tracer to study cellular metabolic processes (J. LEUCOCYTE BIOL. 45, 277 (1989)). The high surface area of beads provides an excellent matrix for attaching chemical entities, such as the compounds of general formula (IIb), or A, by using a classical condensing agent, while the fluorescent properties of these particles enable them to be detected with high sensitivity. They can be quantitated by their fluorescence either in aqueous suspension or when captured on membranes.

Fluorescent beads can be visualized with a variety of imaging techniques, including ordinary light or fluorescence microscopy and laser scanning confocal microscopy as well as fluorescent/flow activated cell sorters (FACS) which may optionally containing cell sorting capabilities.

The most preferred beads of the present invention are fluorescent, 2□ diameter beads having carboxy or amino groups that can be derivatized as known by those skilled in the art, such as those from Molecular Probes Inc.

In the present invention peptide A or its analogues provide sufficient binding strength to attach ultrasound agents, such as microbubbles or microballoons or beads to cultured HAEC (Human aortic endothelial cells) under flow. Where desirable, the binding strength and stability of lead compounds can be optimized using methods known to those of ordinary skill in the art. In a preferred embodiment of the invention, to facilitate the attachment of compound libraries to beads, the compounds can be synthesized with a tag, such as biotin, which will tightly associate with an acceptor molecule on the beads, such as avidin or vice versa.

The beads do not necessarily have to be labeled with fluorescence or radioactivity. They can be prepared such that they can be detected and quantified by visible light methods (colorimetry), or contain an enzyme or other signal generating system known to those skilled in the art that can be activated after specific binding to a target has occurred.

Beads can be reacted with the compounds of general formula (IIb) to give the agents of general formula (Ib). The beads conjugated to the targeting peptide of the invention may then be used in assays, such as, for example, to assess binding to endothelial cells. Specifically, human or rabbit aortic endothelial cells in culture were used as a model for vascular endothelium. These cells were routinely proved to be endothelial cells by demonstration of the expression of the known endothelial cell specific markers von Willebrand factor and VE-cadherin (as detailed for example in H. M. Piper, et al. From H. M. Piper, ed., "Cell Culture Techniques in Heart and Vessel Research", Springer-Verlag, Berlin (1990); p. 158-177. VE-cadherin was detected by a modification of the method used by Dejana et. al. (E. Dejana, et al., J. Cell Biol. (1987); 104:1403-1411)). The beads conjugated to the targeting peptide A of the invention were incubated under various conditions with HAEC (human aortic endothelial cell) monolayers in culture and the specifically bound beads quantitated and compared to the underivatized beads or beads derivatized with compounds not known to target endothelial cells. Such as, for example, BSA (bovine serum albumin), the peptide GRGDSP (SEQ ID NO:3), glycine. The results demonstrated that compounds of general formula (IIb) effectively target (bind) derivatized beads to HAEC, while underivatized beads or beads derivatized with BSA, GRGDSP (SEQ ID NO: 3), or glycine do not.

The ultrasound agents of the present invention containing the targeting moiety A were treated in a similar manner. The incubations were also performed under flow conditions to simulate the in vivo environment. These studies demonstrate that the ultrasound agents are also targeted to HAEC by the targeting moiety A, whereas ultrasound agents lacking the targeting moiety do not bind. Further, the binding was shown to extend to aortic endothelial cells from another species, such as rabbits, but not to a non-endothelial human cell line, KB.

In another preferred embodiment of the present invention, the invention includes compounds of the formula A-L-B$_2$, where B$_2$ corresponds to B$_{2b}$ a non-ionic surfactant such as (PVA), polyoxyethylene-polyoxypropylene block copolymers, e.g. Pluronic®, Synperonic®, Poloxamer®, Poloxamine®, or BRIJ®.

These compounds are particularly useful for preparing targeted MRI contrast agents based on lipophilic iron particles The novel compositions of the present invention, and especially the microbubbles and microballoons, are useful as contrast media in diagnostic imaging, and are also suitable as therapeutic agents, in the presence or not of a bioactive agent, as cited above. This may be achieved by administering the compounds of general formula I such that the receptors involved with angiogenesis, such as the NP-1 VEGF receptor are occupied and unreceptive to endogenous receptor binders such as VEGF.

Another method of therapy is to use the compounds of general formula I as vehicles with which to target bioactive compounds to a desired site.

In one embodiment, the compostions of the invention may be used to deliver one or more bioactive agents. A bioactive agent is a compound that is capable of providing a biological effect, including a therapeutic or cytotoxic effect. In this embodiment the substrate B may be, for example, a known drug delivery vehicle such as, for example, a liposome, a microparticle etc. In a preferred embodiment, the targeting moiety A is a TKPPR (SEQ ID NO: 2) multimer such as a TKPPR (SEQ ID NO: 2) tetramer.

As bioactive agent is used herein to encompass genetic material, the substrate B may also include a known gene or nucleic acid delivery vehicle (such as, for example, a virus particle, a gene therapy vector, a liposome, a complex of lipids (e.g. cationic lipids) and genetic material, a complex of dextran derivatives and genetic material etc,.)

Additionally, as discussed in more detail herein, A, the targeting peptide of the invention may be conjugated (optionally through a linker) to a bioactive agent-containing gas filled microbubble or microballoon. In this embodiment, the gas filled contrast agent includes the targeting peptide of the invention; thus it is able to target the agent to tumor cells or endothelial cells (and particularly angiogenic endothelial cells). Ultrasound may then be used to rupture the targeted, bioactive agent-containing ultrasound contrast agent of the invention, thus releasing the bioactive agent.

Interaction of the bioactive agent with the desired target may be whilst still part of the vehicle or upon release from the vehicle which may be by passive or active means. Passive means are those such as diffusion away from the vehicle whilst the vehicle is bound to its target and active means may be those such as insonation of the vehicle to achieve rupture and release of the carried bioactive material.

Any of a variety of bioactive agents may be used in and delivered by the compostions of the invention. By bioactive agent, as used therein, is meant an agent having a beneficial, therapeutic or cytotoxic effect in vivo. As used herein, the term bioactive agent encompasses genetic material and is synonymous with the terms therapeutic, chemotherapeutic, drug, etc. Suitable bioactive agents include, but are not limmied to: antineoplastic agents, such as platinum compounds (e.g., spiroplatin, cisplatin, and carboplatin), methotrexate, adriamycin, mitomycin, ansamitocin, bleomycin, cytosine, arabinoside, arabinosyl adenine, mercaptopolylysine, vincristine, busulfan, chlorambucil, melphalan (e.g., PAM, a, L-PAM or phennylalanine mustard), mercaptopurine, mitotane. procarbazine hydrochloride, dactinomycin (actinomycin D), daunorubcin hydrochloride, doxorubicin hydrochloride, taxol, mitomycin, plicamycin (mithramycin), aminoglutethimide, estramustine phosphate sodium, flutamide, leuprolide acetate, megestrol acetate, tamoxifen citrate, testolactone, trilostane, amsacrine (m-AMSA), asparaginase (L-asparaginase) Erwina aparaginase, etoposide (VP-16), interferon α-2a, interferon α-2b, teniposide (VM-26), vinblastine sulfate (VLB), vincristine sulfate, bleomycin sulfate, adriamycin, and arabinosyl; blood products such as parenteral iron, hemin, hematoporphyrins and their derivatives, biological response modifiers such as muramyldipeptide, muramyltripeptide, microbial cell wall components, lymphokines (e.g., bacterial endotoxin such as lipopolysaccharide, macrophage activation factor), sub-units of bacteria (such as Mycobacteria, Corynebacteria), the synthetic dipeptide N-acetyl-muramyl-1-alanyl-I)-isoglutamine; anti-fungal agents such as ketoconazole, nystatin, griseofulvin, flucytosine (5-fc), miconazole, amphotericin B, ricin, and β-Iactam antibiotics (e.g., sulfazecin); hormones such as growth hormone, melanocyte stimulating hormone, estradiol, beclomethasone, dipropionate, betamethasone, betamethasone acetate and betamethasone sodium phosphate, vetamethsone disodium phosphate, vetemthsone sodium phosphate, cortisoneacetate, dexamethasone, dexamethasone acetate, dexamethasone sodium phosphate, flunisolide, hydrocortisone, hydrocortisone acetate, hydrocortisone cvpionate, hydrocortisone sodium phosphate, hydrocortisone sodium succinate, methylprednisolone, methylprednisolone acetate, methylprednisolone sodium succinate, paramethasone acetate, prednisolone, prednisotone acetate, prednisolone sodium phosphate, prednisolone tebutate, prednisone, triamcinolone, triamcinolone acetonide, triamcinolone diacetate, triamcinolone hexacetonide and fludrocortisone acetate; vitamins such as cyanocobalamin neinoic acid, retinoids and derivatives such as retinol palmitate, and α-tocpherol; enzymes such as manganese super oxide dimsutase or alkaline phosphatase; anti-allergice agents such as amelexanox; anti-coagulation agents] such as phenprocoumon and heparin; circulatory drugs such as propranolol; metabolic potentiators such as glutathione; antituberculars such as para-aminosalicylic acid, isoniazid, capreomycin sulfate cycloscrine, ethambutol hydrochloride ethionamide, pyrazinamide, rifampin, and streptomycin sulfate; antivirals such as acyclovir, amantadine azidothymidine (AZT or Zidovudine), ribavirin and vidarabine monohydrate (adenine arahinoside, ara-A); antianginals such as diltiazem, nifedipine, verapamil, erythritol tetranitrate, isosorbide dinitrate, nitroglycerin (glyceryl trinitrate) and pentaerythritol tetranitrate; antibiotics, anti-inflammatories such as diflunisal, ibuprofen, indomethacin, meclofenamate, mefenamic acid, naproxen, oxyphenbutazone, phenylbutazone, piroxicam, sulindac, tolmetin, aspirin and salicylates; antiprotozoans such as chloroquine, hydroxychloroquine, metroidazole, quinine and meglumine antimonate; antirheumatics such as penicillamine; narcotics such as paregoric; opiates such as codeine, heroin, methadone, morphine and opium; cardiac glycosides such as deslanoside, digitoxin, digoxin, digitalin and digitalis, neuromuscular blockers such as atracutrium mesylate, gallamice triethiodide, hexafluorenium bromide, metocurine iodide, pancuronium bromide, succinylcholine chloride (suxamethonium chloride), tubocurarine chloride and vecuronium bromide; sedatives (hypnotics) such as amobarbital, amobarbital sodium, aprobarbital, butabarbital sodium, chloral hydrate, ethchlorvynol, ethinamate, flurazepam hydrochloride, glutethimide, methotrimeprazine hydrochloride, methyprylon, midazolam hydrochloride, paraldehyde, pentobarbital, pentobarbital sodium, phenobarbital sodium, secobarbital sodium, talbutal, temazepam and triazolam; local anesthetics such as bupivacaine hydrochloride, chloroprocaine hydrochloride, etidocaine hydrochloride, lidocaine hydrochloride, mepivacaine hydrochloride, procaine hydrochloride and tetracaine hydrochloride; and general anesthetics such as droperidol, etomidate, fentanyl citrate with droperidol, ketamine hydrochloride, methohexital sodium and thiopental sodium. In certain embodiments, the therapeutic is a monoclonal antibody, such as a monoclonal antibody capable of binding to melanoma antigen.

Other preferred therapeutics include genetic material such as nucleic acids, RNA, and DNA, of either natural or synthetic origin, including recombinant RNA and DNA and antisense RNA and DNA. Types of genetic material that may be used include, for example, genes carried on expression vectors such as plasmids, phagemids, cosmids, yeast artificial chromosomes (YAC's) and defective or "helper" viruses, antigene nucleic acids, both single and double stranded RNA and DNA and analogs thereof, such as phosphorothioate and phosphorodithioate oligodeoxynucleotides. Additionally, the genetic material may combined, for example, with lipids, proteins or other polymers.

DNA encoding certain proteins may be used in the treatment of many different types of diseases. For example, adenosine deaminase may be provided to treat ADA deficiency; tumor necrosis factor and/or interleukin-2 may be provided to treat advanced cancers, HDL receptor may be provided to treat liver disease; thymidine kinase may be provided to treat ovarian cancer, brain tumors, or HIV infection; HLA-B7 may be provided to treat malignant melanoma interleukin-2 may be provided to treat neuroblastoma, malignant melanoma, or kidney cancer; interleukin-4 may be provided to treat cancer; HIV env may be provided to HIV infection; antisense ras/p53 may be provided to treat lung cancer; and Factor VIII may be provided to treat Hemophilia B. See, for example, *Science* 258, 744-746, incorporated herein by reference.

In accordance with the present invention, there are provided methods of imaging a patient generally, and/or in specifically diagnosing the presence of diseased tissues in a patient. The imaging process of the present invention may be carried out by administering a contrast medium of the invention to a patient, and then scanning the patient using, for example, ultrasound, computed tomography, and/or magnetic resonance imaging or scintigraphy, to obtain visible images of an internal region of a patient and/or of any diseased tissue in that region. By region of a patient, it is meant the whole patient or a particular area or portion of the patient.

Nevertheless, as discussed above, the present invention also provides the possibility to use compositions comprising a monomer, multimer or polymer of timer or polymer of TKPPR (SEQ ID NO: 2) or a TKPPR (SEQ ID NO: 2) analogue, without the presence of a bioactive agent, as a therapeutic agent useful as an inhibitor of the angiogenesis process.

The administration of the compositions of the present invention is generally parenteral and the amount and the period of time are depending upon a variety of factors including, for example, the volume of the composition to be administered, the weight of the patient, the region of interest etc. Another possible route of administration is the topical application, particularly useful for the skin diseases associated with angiogenesis, as cited above.

The following are embodiments of the invention:

1. A compound of the formula (I)

A-L-B    (I)

in which
    A is TKPPR (SEQ ID NO: 2) or an analogue of TKPPR (SEQ ID NO: 2) which specifically binds to an endothelial cell or cells that express markers in common with endothelial cells, with equal or greater avidity as TKPPR (SEQ ID NO: 2);
    L is a linker;
    B is a substrate.

2. A compound according to embodiment 1, wherein B corresponds to $B_1$, which is a lipid able to bind the linker in a covalent or not covalent manner.

3. A compound according to embodiment 1, wherein B corresponds to $B_2$, which is a non lipid polymer able to bind the linker in a covalent manner.

4. A compound according to embodiment 2, in which $B_1$ is a synthetic or naturally-occurring generally amphipathic and biocompatible compound, selected from the group consisting of fatty acids; lysolipids; phospholipids; phosphatidylinositol; sphingolipids; glycolipids; glucolipids; sulfatides; glycosphingolipids; phosphatidic acids; lipids bearing polymers; lipids bearing sulfonated mono- di-, oligo- or polysaccharides; cholesterol, cholesterol sulfate; cholesterol hemisuccinate; tocopherol hemisuccinate; lipids with ether and ester-linked fatty acids; polymerized lipids; diacetyl phosphate; dicetyl phosphate; stearylamine; cardiolipin; phospholipids with short chain fatty acids of about 6 to about 8 carbons in length; synthetic phospholipids with asymmetric acyl chains; ceramides; non-ionic liposomes; sterol esters of sugar acids; esters of sugars and aliphatic acids; saponins; glycerol dilaurate; glycerol trilaurate; glycerol dipalmitate; glycerol; glycerol esters; long chain alcohols; 6-(5-cholesten-3β-yloxy)-1-thio-β-D-galactopyranoside; digalactosyldiglyceride; 6-(5-cholesten-3β-yloxy)hexyl-6-amino-6-deoxy-1-thio-β-D-galactopyranoside; 6-(5-cholesten-3β-yloxy)hexyl-6-amino-6-deoxyl-1-thio-β-D-mannopyranoside; 12-(((7'-diethylaminocoumarin-3-yl)carbonyl)methylamino) octadecanoic acid; N-[12-(((7'-diethylaminocoumarin-3-yl)carbonyl)methylamino)octadecanoyl]-2-aminopalmitic acid; N-succinyldioleylphosphatidylethanolamine; 1,2-dioleyl-sn-glycerol; 1,2-dipalmitoyl-sn-3-succinylglycerol; 1,3-dipalmitoyl-2-succinylglycerol; 1-hexadecyl-2-palmitoylglycerophosphoethanolamine; palmitoylhomocysteine, and combinations thereof.

5. A compound according to embodiment 3, in which $B_2$ is $B_{2a}$ which is a polymer useful for producing microparticles, or $B_{2b}$, a non-ionic surfactant.

6. A compound according to embodiment 3 selected from the group consisting of PVA, and a polyoxyethylene-polyoxypropylene block copolymer.

7. A compound according to embodiment 4, in which $B_{2a}$ is a bead which is derivatizable and is attached to a detectable label.

8. A compound according to embodiment 7, in which the detectable label is a fluorescent or radioactive marker.

9. A compound according to embodiments 1 to 8, in which L is a bond or is derived from:
    an alkyl chain $C_1$-$C_{6000}$, linear or branched, saturated or unsaturated, optionally interrupted or substituted by one or more groups such as: O, S, NR, OR, SR, COR, COOH, COOR, CONHR, CSNHR, C=O, S=O, S(=O)$_2$, P=O(O)$_2$OR, P(O)$_2$(OR)$_2$, halogens, or phenyl groups, optionally substituted by one or more —NHR, —OR, —SR, —COR, —CONHR, —N=C=S, —N—C=O, halogens, in which
        R is H or an alkyl group $C_1$-$C_4$, linear or branched, optionally substituted by one or more —OH;
    such a chain can be interrupted or substituted by one or more cyclic groups $C_3$-$C_9$, saturated or unsaturated, optionally interrupted by one or more O, S or NR; by one or more groups such as: —NHR, —OR, —SR, —COR, —CONHR, or a phenyl group optionally substituted by one or more —NHR, —OR, —SR, —COR, —CONHR, —N=C=S, —N—C=O, halogens.

10. A compound according to embodiment 9, in which the cyclic groups present in L are saturated or unsaturated, and correspond to the following general formula (III)

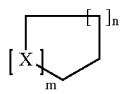

(III)

in which
n can range from 0 to 4;
m can range from 0 to 2;
X can be NH, NR, O, S or SR.
11. A compound according to embodiment 10, in which the linker L is an oligopeptide constituted from 1 to 100 of natural or synthetic amino acids.
12. A compound according to embodiment 11, in which the aminoacids are selected in the group from glycine, glutamic acid, aspartic acid, γ-amino-butyric acid, trans-4-aminomethyl-cyclohexane carboxylic acid.
13. A compound according to embodiment 10, in which the L precursor corresponds to difunctional PEG(polyethyleneglycol) derivatives.
14. A compound according to embodiment 10, in which L is selected in a group consisting of: glutaric acid, succinic acid, malonic acid, oxalic acid, PEG derivatized with two CH$_2$CO groups.
15. A compound of the formula (IIa), according to embodiment 2

A-L-B$_{1a}$  (IIa)

in which
B$_{1a}$ is a phospholipid moiety of the formula (II),

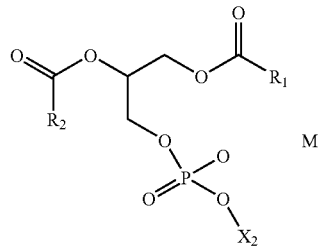

(II)

and
M is an alkaline or alkaline-earth metal cation;
R$_1$ and R$_2$ independently, correspond to a linear long chain C$_{12}$-C$_{20}$; saturated or unsaturated, optionally interrupted by C=O, or O;
X$_2$ is selected in a group consisting of

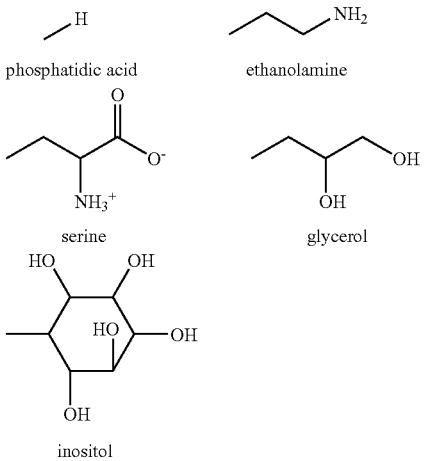

16. A compound according to embodiment 15, in which R$_1$ and R$_2$ are independently a saturated linear long chain C$_{12}$-C$_{20}$.
17. A compound according to embodiment 16, in which the phospholipids of formula (II) are selected in the group from: dimyristoylphosphatidylethanolamine, dipalmitoylphosphatidylethanolamine, distearoylphosphatidylethanolamine, diarachidoylphosphatidylethanolamine, dioleylphosphatidylethanolamine, dilinoleylphosphatidylethanolamine, fluorinated analogues of any of the foregoing, and mixtures of any of the foregoing.
18. A compound according to embodiment 17, in which the phospholipid of formula (II) is dipalmitoylphosphatidylethanolamine.
19. A compound selected in the group consisting from:

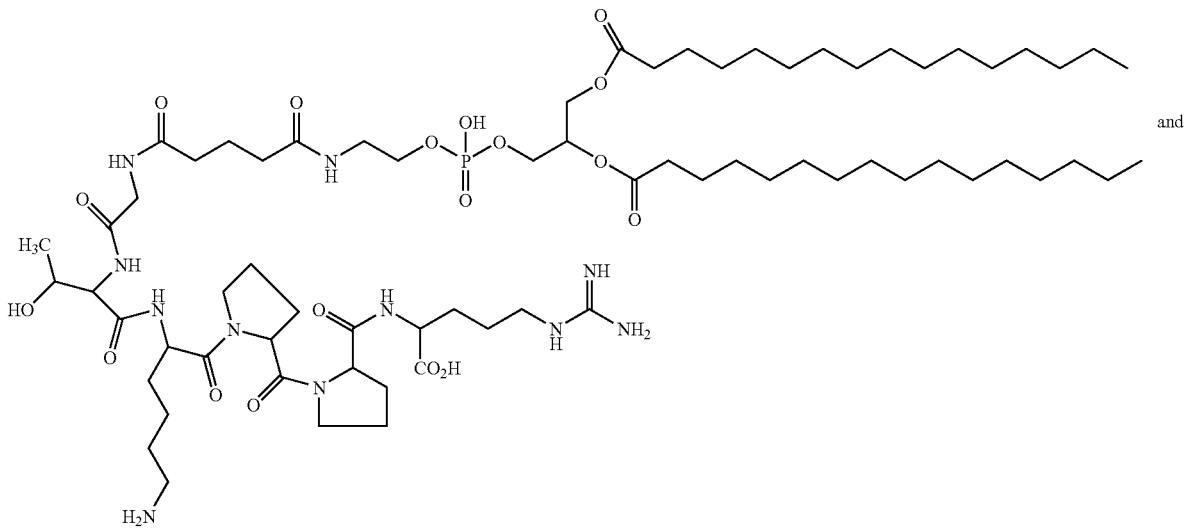

and

-continued

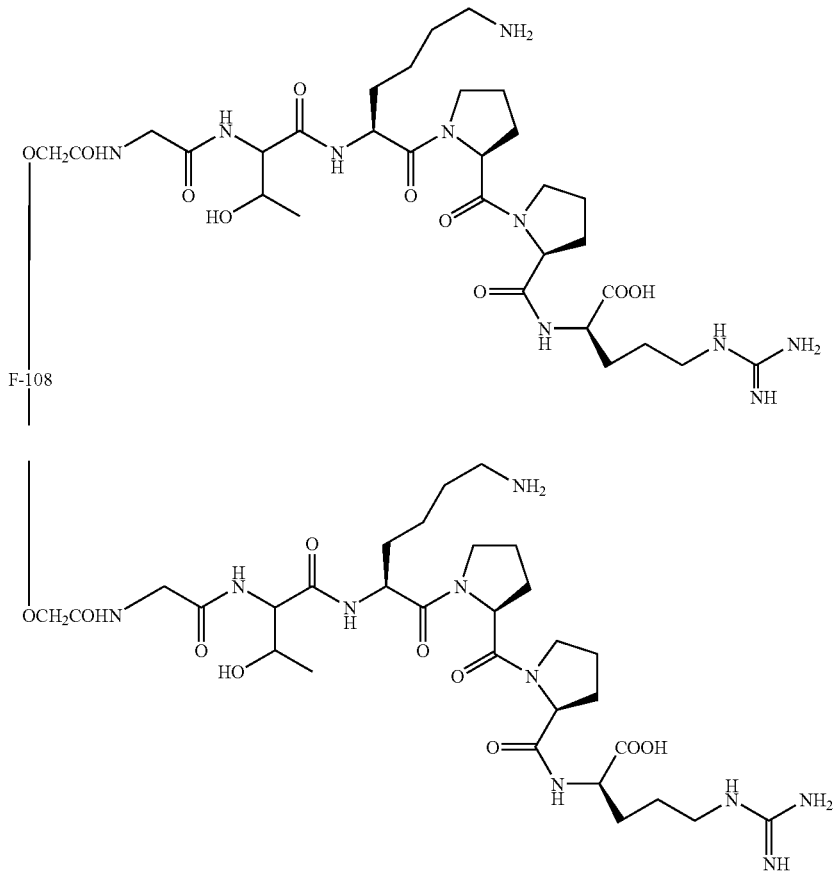

F-108

20. A process for preparing a compound of embodiment 1 comprising the following steps:

obtaining TKPPR (SEQ ID NO: 2) or an analogue thereof;

conjugating TKPPR (SEQ ID NO: 2) with the linker to give a compound of formula (IIb)

$$A\text{-}L \quad (IIb);$$

and forming a covalent or non-covalent bond between a compound of formula (IIb) and the substrate B or forming a covalent bond between the substrate B and the linker to form a conjugate B-L, and conjugating of the conjugate B-L with TKPPR (SEQ ID NO: 2) or an analogue thereof.

21. A process according to embodiment 20, in which the compounds of formula (IIb) are prepared as illustrated in the following Scheme

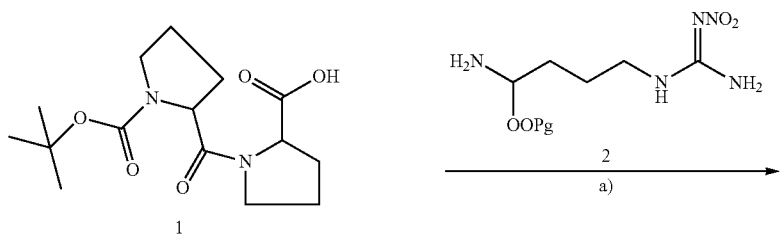

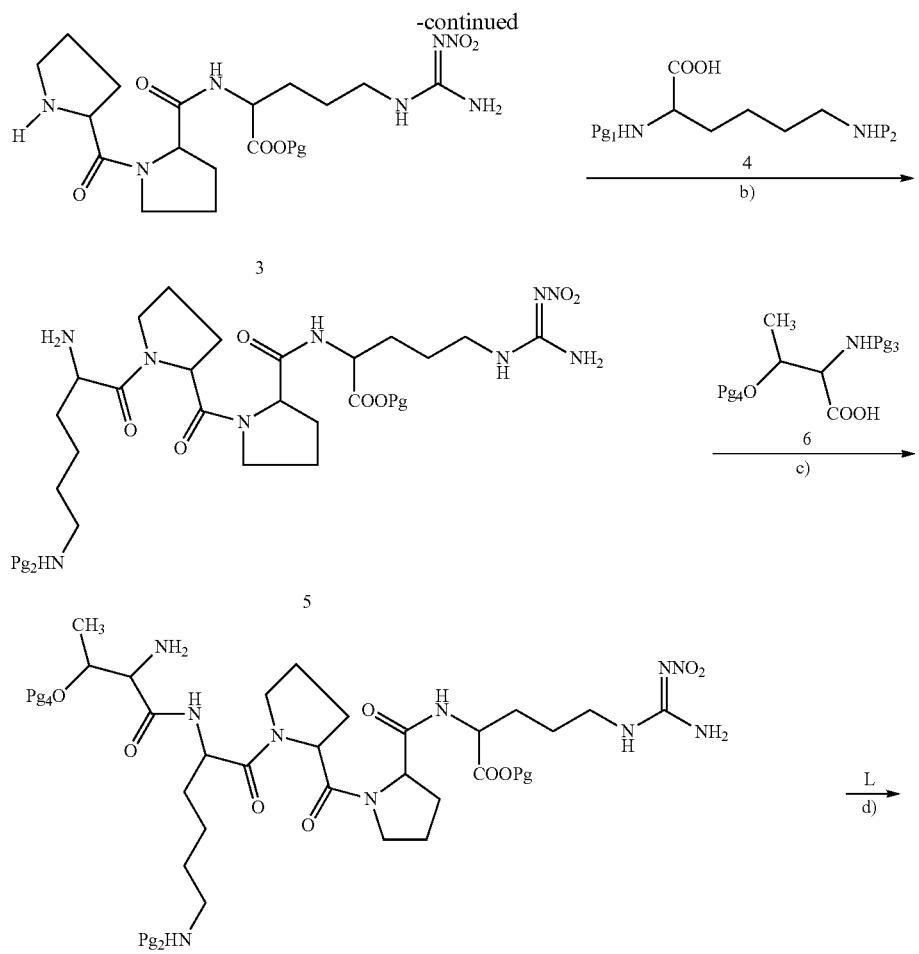

(Pg = protecting group)

in which
the steps a), b), and c) are all condensation reactions performed under basic conditions, and step d) is a condensation in basic conditions with the linker.

22. A composition for targeting endothelial cells or cells that express markers in common with endothelial cells, of humans and animals, in vivo or in vitro, and/or for administration of at least one bioactive agent, comprising at least one of the compounds of embodiment 1 with an optional detectable moiety.

23. A composition, according to embodiment 22, comprising an ultrasound detectable moiety and at least one of the compounds of formula (Ia) or (IIa).

24. A composition, according to embodiment 22, further comprising at least one bioactive agent incorporated in the detectable moiety.

25. A composition, according to embodiment 23, comprising a compound of formula (Ib), for targeting said ultrasound detectable moiety.

26. A method of imaging an angiogenic site in an human or animal comprising administering to said animal a composition comprising a detectable moiety and a compound of formula (Ia) or (IIa) and detecting said moiety at an angiogenic site.

27. A method of staging a tumor in an animal comprising administering a composition comprising a detectable moiety and a compound of formula (Ia) or (IIa) to said animal and detecting said moiety in said animal.

28. A method of ultrasound imaging comprising administering an ultrasound contrast media composition comprising a compound of formula (Ia) or (IIa) to said animal and imaging said contrast agent in said animal.

29. A method of screening at least one agent for the specificity of said agent to target endothelial cells or cells that express markers in common with endothelial cells, of an animal, comprising administering to said animal or contacting said cells in vitro with a composition comprising a compound of formula (Ib) and detecting said specificity.

30. A method of screening at least one targeted ultrasound contrast media, according to embodiment 29, comprising administering or contacting a compound of formula (Ib).

31. A method for the therapeutic delivery in vivo of a bioactive agent to a patient suffering from effects associated with angiogenesis disorders comprising administering a therapeutically effective amount of a composition comprising a compound of formula (Ia) or (IIa).

32. A method of treating an individual experiencing an effect of an angiogenesis disorder comprising administering a therapeutically effective amount of a composition comprising a compound of formula (Ia) or (IIa).

The invention is further demonstrated in the following examples. The examples are for purposes of illustration and are not intended to limit the scope of the present invention.

The disclosure of all of the above-described references, patents and patent applications are incorporated herein by reference in their entirety.

EXAMPLES

The stereochemistry of the chemical bonds in the drawings of the Examples will be omitted because the amino acids all have the natural configuration S at the chiral center and there is always retention of configuration in the exemplified reactions.

Example 1

Preparation of TKPPR-OH (SEQ ID NO: 2)

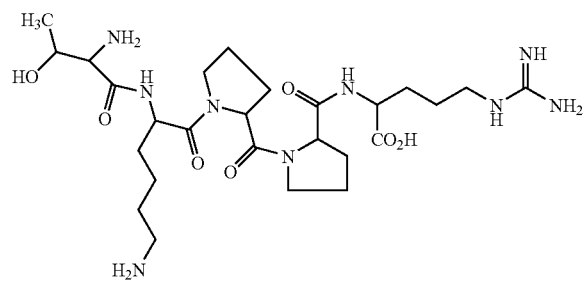

A) Preparation of Pro-Pro-Arg(NO$_2$)Obzl

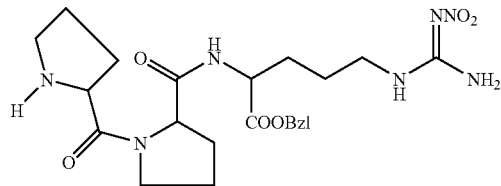

To a solution of Boc-Pro-Pro-OH (commercially available) (3.2 g, 10.25 mmol) in methylene chloride (100 mL) was added Arg(NO$_2$)Obzl.PTSA salt (commercially available) (6.54 g, 10 mmol) and the mixture was stirred for 5 min. This mixture was cooled to 5° C. and HATU ([O-(7-azabenzotriazol-1-yl)1,1,3,3,-tetramethyluronium hexafluorophosphate], (commercially available), (3.9 g, 10.25 mmol) was added in one lot followed by diisopropylethylamine (6.5 g, 50 mmol). After stirring the reaction mixture for 12 h at room temperature, the solvents were removed in vacuo, the residue dissolved in ethyl acetate and washed with saturated sodium bicarbonate, sodium bisulphate and finally with water. The organic layer was dried and solvent removed to afford the coupled product. This was purified by column chromatography over silica gel using 5% methanol in ethyl acetate as the eluent. Fractions containing the pure material were combined and solvent removed to obtain the pure product. To a solution of this protected tripeptide (5.42 g, 9 mmol) in methylene chloride (12 mL) was added trifluoro acetic acid (TFA) (12 mL) and the mixture was stirred for 1 hr at room temperature.

TFA and methylene chloride were removed in vacuo and the residue stirred with anhydrous ether for 15 min. The precipitated solid was collected and dried to afford 5.2 g of the title compound, as the TFA salt.

| | |
|---|---|
| Yield: | 95% |
| HPLC Purity: | 100% |
| Retention Time: | 9.8 min |
| Column: | YMC, C-18 (4.6 × 250 mm) |
| Solvent: | Water-Acetonitrile, both containing 0.1% TFA |
| Elution condition: | Initial, 20% acetonitrile, linear gradient to 100% acetonitrile in 30 min; |
| Flow rate: | 1.0 mL/min |
| Detection: | UV 254 nm. |

$^1$H-NMR, and HRMS spectra are consistent with the structure

B) Preparation of Lys(Z)-Pro-Pro-Arg(NO$_2$)Obzl (SEQ ID NO: 12)

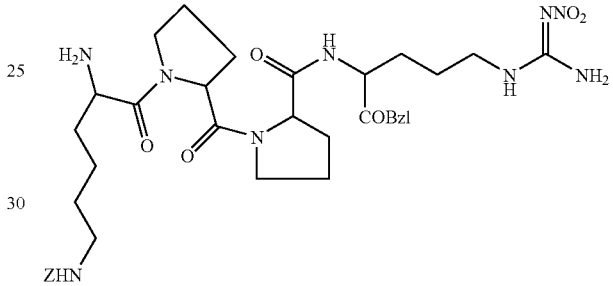

To a solution of Z protected lysine (commercially available) (3.05 g, 8.02 mmol) in methylene chloride (60 mL) was added the TFA salt of Pro-Pro-Arg(NO$_2$)Obzl (4.93 g, 8 mmol) and the mixture was stirred for 5 min. This mixture was cooled to 5° C. and HATU (3.05 g, 8.02 mmol) was added in one lot followed by diisopropylethylamine (4.16 g, 32 mmol). After stirring the reaction mixture for 6 h, the solvents were removed in vacuo, the residue dissolved in ethyl acetate and washed with saturated sodium bicarbonate, sodium bisulphate and finally with water. The organic layer was dried and solvent removed to afford the coupled product. This was purified by column chromatography over silica gel (150 g) using 5% methanol in ethyl acetate as the eluent. Fractions containing the pure material were combined and solvent removed to obtain the pure product. A solution of this protected tetra peptide (6.0 g, 7 mmol) in methylene chloride (15 mL) was added TFA (15 mL) and the mixture stirred for 1 hr at room temperature. TFA and methylene chloride were removed in vacuo and the residue stirred with anhydrous ether for 15 min. The precipitated solid was collected and dried to afford 5.8 g of the title compound, as the TFA salt.

| | |
|---|---|
| Yield: | 95% |
| HPLC: | 95.7% |
| Retention Time: | 14.02 min. |
| Column: | YMC, C-18 (4.6 × 250 mm) |
| Solvent: | Water-Acetonitrile, both containing 0.1% TFA |
| Elution condition: | Initial 20% acetonitrile, linear gradient to 100% acetonitrile in 30 min |
| Flow rate: | 1.0 mL/min |
| Detection: | UV 254 nm. |

$^1$H-NMR, and HRMS spectra are consistent with the structure

C) Preparation of Thr(Obzl)-Lys(Z)-Pro-Pro-Arg(NO$_2$)Obzl (SEQ ID NO: 2)

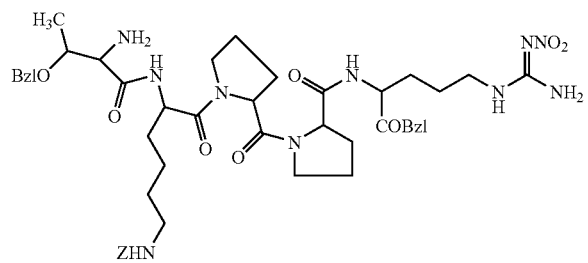

To a solution of Boc-threonine benzyl ether, (commercially available) (1.96 g, 6.3 mmol) in methylene chloride (50 mL) was added TFA salt of Lys(Z)-Pro-Pro-Arg(NO$_2$)Obzl (SEQ ID NO: 12) (5.25 g, 6 mmol) and the mixture was stirred for 5 min. This mixture was cooled to 5° C. and HATU (2.41 g, 6.3 mmol) was added in one lot followed by diisopropylethylamine (3.35 g, 25 mmol). After stirring the reaction mixture for 4 h at room temperature, the solvents were removed in vacuo, the residue dissolved in ethyl acetate and washed with saturated sodium bicarbonate, sodium bisulphate and finally with water. The organic layer was dried and solvent removed to afford the coupled product. This was purified by column chromatography over silica gel (150 g) using 5% methanol in ethyl acetate as the eluent. Fractions containing the pure material were combined and solvent removed to obtain the pure product (5.08 g, yield 91%). A solution of this protected penta-peptide (2.1 g, 2 mmol) in methylene chloride (4 mL) was added TFA (4 mL) and the mixture stirred for 1 hr at room temperature. TFA and methylene chloride were removed in vacuo and the residue stirred with anhydrous ether for 15 min. The precipitated solid was collected and dried to afford 2.1 g of the title compound as the TFA salt.

| | |
|---|---|
| Yield: | 98% |
| HPLC: | 98.3% |
| Retention Time: | 16.12 min |
| Column: | YMC, C-18 (4.6 × 250 mm) |
| Solvent: | Water-Acetonitrile, both containing 0.1% TFA |
| Elution condition: | Initial, 20% acetonitrile, linear gradient to 100% acetonitrile in 30 min |
| Flow rate: | 1.0 mL/min. |
| Detection: | UV 254 nm |

$^1$H-NMR, and HRMS spectra are consistent with the structure.

D) Preparation of TKPPR-OH (SEQ ID NO: 2)

To a solution of the above compound (300 mg, 0.28 mmol) in methanol (30 mL) and acetic acid (3.0 mL) was added Pd(OH)$_2$ (Degussa type, 100 mg) and the mixture was hydrogenated at 50 psi for 48 hr. The catalyst was filtered off and the solvents were removed to afford the crude product. This was triturated with anhydrous ether to obtain the product as a white powder. This crude product was further purified by preparative HPLC on a C-18 column using a linear gradient of 0-30% acetonitrile in 60 min. Fractions containing pure compound were combined and lyophilized to afford 210 mg of the pure TKPPR-OH (SEQ ID NO: 2).

| | |
|---|---|
| Yield: | 84%). |
| Retention Time: | 13.40 min. |
| Column: | YMC, C-18 (4.6 × 250 mm) |
| Solvent: | Water-Acetonitrile, both containing 0.1% TFA |
| Elution condition: | Initial, 0% acetonitrile, linear gradient to 30% acetonitrile in 30 min |
| Flow rate: | 1.0 mL/min. |
| Detection: | UV 220 nm. |

Elemental Analysis:

| | C | H | N |
|---|---|---|---|
| Calcd. | 40.13 | 5.47 | 13.16 |
| Found | 40.55 | 5.55 | 12.79 |

$^1$H-NMR, and HRMS spectra are consistent with the structure and with the literature data Example 2

Endothelial Cell Binding of TKPPR (SEQ ID NO: 2)-Conjugated Fluorescent Beads to HAEC A) Cell Culture Human aortic endothelial cells (HAEC) from Biowhittaker were grown as monolayers in EGM-MV medium from Biowhittaker according to the supplier's instructions.

Briefly, a frozen cryovial of cells (500,000 cells in about 1 mL) was thawed for 2-3 minutes in a 37° C. water bath and cells were seeded into a T-75 flask coated with collagen I (commercially available) containing 15 mL EGM-MV of medium pre-equilibrated with 5% CO$_2$ atmosphere. Cells were incubated in a standard tissue culture incubator at 37° C. HAEC were subcultured for up to 3 additional passages, using the following protocol:

Culture medium from confluent T75 flasks of HAEC (6-8 days after seeding) was removed by aspiration, and cells were washed with Dulbecco's phosphate-buffered saline without Mg$^{++}$ or Ca$^{++}$ (commercially available).

They were then trypsinized as recommended by Biowhittaker.

The resulting cell suspension was pelleted by centrifugation. The cell concentration was determined, and a volume of the resuspended cells containing 450,000 cells was added to a collagen I-coated T-75 flask (seeding density=6,000 cells/cm$^2$) and fresh culture medium was added to bring the final volume of the flask to 15 mL. Flasks were incubated at 37° C. in a standard tissue culture incubator in 5% CO$_2$ atmosphere, with loosened caps to allow gas exchange. The next day, medium was aspirated to remove non-adherent cells, and replaced with fresh medium. Thereafter, medium was replaced every 2-3 days.

For binding studies and characterization, pelleted cells were diluted to a concentration of 16,560 cells per mL, and 0.5 mL was seeded into each well of an 8-well chamber slide (Collagen I-coated, Becton Dickinson) to generate a seeding density of 12,000 cells/cm$^2$. Cells seeded into chamber slides were used for assays after 7 to 10 days, and were not further propagated.

B) Immunofluorescent Demonstration of Endothelial Cell Markers

Post-confluent (8-14 days in culture) HAEC that had been fixed in ice-cold methanol 5 min and air-dried 15 min were stained for von Willebrand Factor. Post-confluent HAEC were fixed in 4% paraformaldehyde and 2% sucrose in D-PBS for 5 min, then stained for VE-cadherin.

Staining was evaluated using an Olympus IMT-2 microscope equipped with a mercury lamp (Chiu Technical Corp, Model M-100) for fluorescence detection and employing either a fluorescein filter set, a Texas Red filter set, or a dual fluorescein/Texas Red filter set.

C) Preparation of Peptide-Conjugated Microspheres

TKPPR (SEQ ID NO: 2) (see preparation described in the Example 1) was attached to red fluorescent carboxylate-modified FluoSpheres™ (Molecular Probes), which are 2.0 µm microspheres provided at $3.9 \times 10^9$ particles/mL of distilled water. 1.0 mg TKPPR (SEQ ID NO: 2) was combined with 0.5 mL of 50 mM MES buffer (2-[N-Morpholino] ethanesulfonic acid, (commercially available), pH 6.0 and 0.2 mL FluoSpheres ($7.8 \times 10^8$ spheres) in a 1.5 mL Eppendorf snap top, polypropylene centrifuge tube and rotated for 30 min at room temperature (RT). Then 2.8 mg EDAC (1-ethyl-3-(3-dimethylaminopropyl)carbodiimide hydrochloride, (commercially available) in 0.025 mL MES was added and the tube was rotated for 2 h at RT. Following the addition of 0.005 mL 1 N NaOH and 5.7 mg glycine in 0.025 mL MES, the tube was rotated for 30 min more at RT. The beads were then washed by employing three cycles of centrifugation at 14,000 rpm (20,800×g) in an Eppendorf 5417R centrifuge for 15 min, discarding the resulting supernatant, and resuspending in D-PBS. Storage was at 4° C. in 0.4 mL DPBS containing 0.05% $NaN_3$ (final bead concentration was about $1.95 \times 10^9$/mL). Conjugation of glycine, GRGDSP (SEQ ID NO: 3) or BSA to the microspheres were carried identically except that BSA was added at 3.0 mg to 0.5 mL buffer.

D) TKPPR (SEQ ID NO: 2)-Conjugated Bead Binding Experiments

Experiment 1.

Red fluorescent microspheres derivatized with TKPPR (SEQ ID NO: 2), GRGDSP (SEQ ID NO: 3), or BSA (as described above) were diluted at 10 µL/mL EBM medium (Biowhittaker) supplemented with 0.1% (w/v) BSA (Sigma) and 20 µL/mL aprotinin (Sigma). Final bead concentration was $1.95 \times 10^7$/mL. Unconjugated microspheres were diluted at 5 µL/mL EBM/BSA buffer to give the same microsphere concentration ($1.95 \times 10^7$/mL) achieved with 10 µL/mL of the conjugated preparations. Before starting the assay, bead suspensions were disaggregated in a sonicating bath for 15 min. The wells of an 8-well chamber slide of confluent HAEC were drained of medium and rinsed with 0.5 mL per well of EBM/BSA buffer (without microspheres). To one well each, 250 µL of the following bead solutions (containing $4.9 \times 10^6$ beads) were added: TKPPR (SEQ ID NO: 2)-conjugated, BSA-conjugated, and unconjugated. The slide was incubated 30 min on an orbital shaker, drained, then washed once with 0.5 mL/well EBM/BSA buffer, and twice with 0.5 mL/well D-PBS containing 2 mM $MgCl_2$. Methanol was applied to the outside of the well separating scaffold to loosen the adhesive, then the scaffold was pulled off and the slide mounted with Gel/Mount (Biomeda) or Vectashield aqueous mounting medium.

Bead binding and localization was assessed at 200× magnification using the same microscopy equipment as described above. Digital images were collected of three different random fields in each well. The images were segregated into separate red or green channels in Adobe PhotoShop (image processing software, version 5.0), flattened (layer information removed), and saved as individual TIFF files. Micrografx Picture Publisher (version 7) was then used to enhance contrast by 100%. Finally, the processed images were inverted into black on a white background using Scion Image software (version beta 3b) and the integrated density was measured with the whole field selected.

Results

The integrated density is in arbitrary units selected by the image analysis software.

| Bead Type | Integrated density of bound beads |
|---|---|
| TKPPR (SEQ ID NO: 2) | 229.97 |
| GRGDSP (SEQ ID NO: 3) | 28.59 |
| BSA | 1.61 |
| Unconjugated | 8.11 |

It is evident that the TKPPR (SEQ ID NO: 2) sequence specifically targets the beads to the endothelial cells.

Experiment 2.

Details were as in experiment 1, except that the microsphere concentration was decreased to $4.9 \times 10^6$/mL (lowering to $1.2 \times 10^6$ the number of microspheres added per well) for each of the bead types, and the incubation buffer was changed to D-PBS containing 0.1% BSA and 10 µL/mL Sigma protease inhibitor cocktail (P-8340). The incubation time was decreased to 15 min on an orbital shaker, and the washes (3) were carried out using D-PBS containing 0.1% Tween 20 (Sigma). Also, in this experiment, cold methanol was added directly to the wells to fix the cells as well as loosen the scaffold. After scaffold removal, a final D-PBS rinse was added to the protocol before coverslipping. TKPPR-bead binding was quantitated in three fields, the other bead types were quantitated in one field only. Bound beads were quantitated by manual counting.

Results

| Bead Type | Number of bound beads |
|---|---|
| TKPPR (SEQ ID NO: 2) | 74, 103, 72 (ave. 83) |
| GRGDSP (SEQ ID NO: 3) | 2 |
| BSA | 1 |
| Unconjugated | 5 |

It is evident that the TKPPR (SEQ ID NO: 2) sequence specifically targets the beads to the endothelial cells.

E) Free TKPPR (SEQ ID NO: 2) Peptide Inhibition of TKPPR (SEQ ID NO: 2) -Conjugated Bead Binding to HAEC HEAC were seeded into each well of an 8-well chamber slide (Collagen I Cellware, Becton Dickinson) and allowed to achieve confluence at 37° C. Solutions containing both TKPPR (SEQ ID NO: 2)-beads (final concentration 4.9×10$^6$/mL) and green control beads (final concentration 4.9×10$^6$/mL) were prepared in D-PBS containing protease inhibitor cocktail (final dilution 1:50) and 0, 10, 25, 50, 100, 200, or 500 µM free TKPPR (SEQ ID NO: 2) peptide. 0.25 mL of each microsphere solution was added to a well in the drained chamber slide and incubated at RT for 15 min. Two wells received the bead solution (mixed unconjugated and TKPPR (SEQ ID NO: 2) beads as indicated above) lacking free competing TKPPR (SEQ ID NO: 2) peptide. The slide was then washed three times with 0.5 mL D-PBS containing 0.1% Tween 20, fixed with methanol for 1 min and mounted. The three images for each level of TKPPR (SEQ ID NO: 2) competition and the six images of the control were averaged and the % inhibition of binding was calculated using the following equation:

% Inhibition=100×(Control Density−Competition Density)/Control Density

A total of eleven 8-well slides were evaluated for competitive TKPPR (SEQ ID NO: 2)-bead binding to HAEC on 7 different days.

| Free TKPPR (SEQ ID NO: 2) [µM] | Average (n = 11) % Inhibition | SD | % CV |
|---|---|---|---|
| 10 | 30.8 | 26.1 | 84.7 |
| 25 | 50.7 | 20.0 | 39.4 |
| 50 | 50.5 | 19.5 | 38.6 |
| 100 | 62.0 | 17.8 | 28.7 |
| 200 | 72.2 | 15.9 | 22.0 |
| 500 | 70.6 | 20.3 | 28.8 |

The % inhibition data clearly show that TKPPR (SEQ ID NO: 2)-beads bind to HAEC in a competitive manner, further illustrated in the chart below. The equation y=A*(1−e$^{-ax}$) was fit to the % Inhibition data to develop a curve which best fits the data using CONSAM software.

Figure 5:
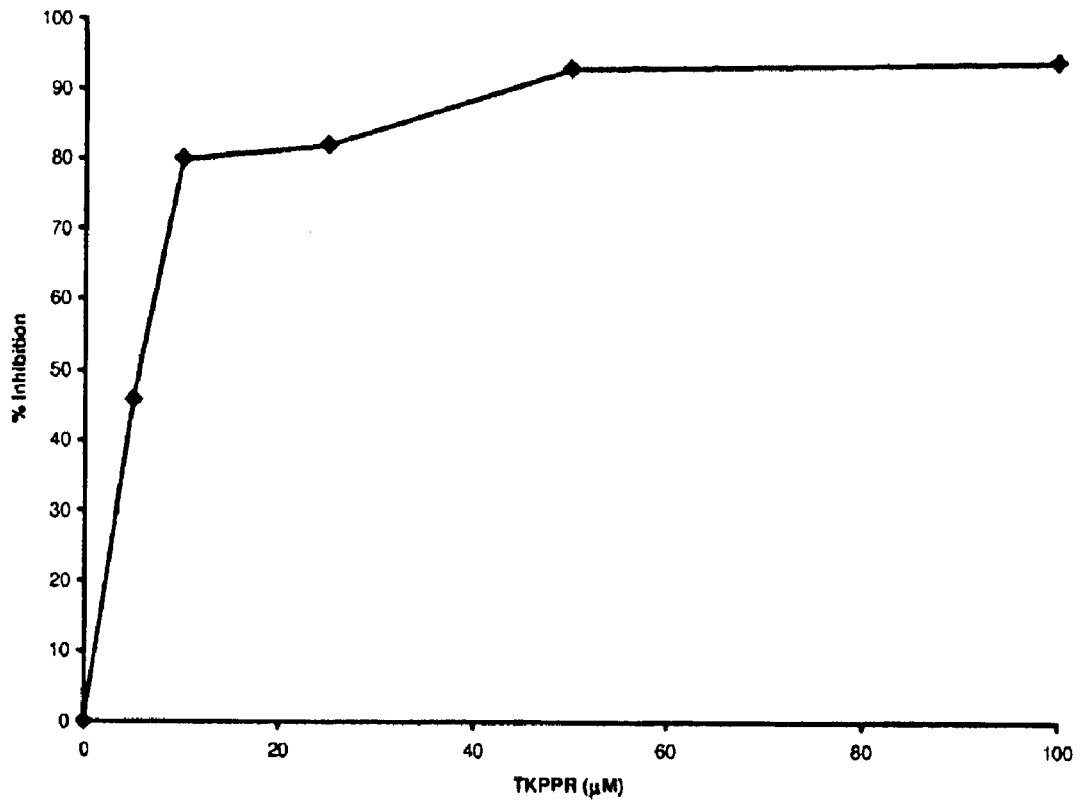
FIG. 5 demonstrates that the TKPPR (SEQ ID NO: 2) peptide sequence can direct specific binding of fluorescent microspheres to HAEC.

These results are summarized in FIG. 5 and demonstrate that the TKPPR (SEQ ID NO: 2) peptide sequence can direct specific binding of fluorescent microspheres to HAEC. This binding can be competed with free peptide.

Example 3

Evaluation of TKPPR (SEQ ID NO: 2)-Bead Binding to Endothelial Cells Under Flow

A) Collagen-Coating of Glass Coverslips

Circular 40 mm diameter glass coverslips (Bioptechs, Cat No. 40-1313-0319) were first derivatized by dipping in 3-aminopropyltriethoxysilane (Pierce, Cat No. 80370ZZ), 20% in acetone (HPLC grade, Sigma Aldrich Cat No. 27,072-5), rinsed in acetone, and air-dried. After autoclaving, the derivatized coverslips were placed into 60 mm round, sterile culture dishes, one coverslip per dish. Five mL of a Collagen I solution (Becton Dickinson, Cat No. 40236), 41.6 µg/mL in 20 mM acetic acid (adjusted to pH 6.7 with NaOH), was added to each coverslip-containing dish. After 15 min, 0.25 mL of 11.5 mg/mL bis(sulfosuccinimidyl) suberate (Pierce, Cat No. 21580ZZ) was added to each dish and mixed in by swirling. After a 105-minute incubation, the dishes were drained and 5 mL of sterile TBS (20 mM Tris-HCl, pH 7.5, 140 mM NaCl) was added to each dish.

B) Cell Culture

Cells were seeded at 12,000 cells per cm$^2$ onto 40-mm diameter glass coverslips (Bioptechs, Butler, Pa., Cat No. 40-1313-0319) that had been collagen I-coated.

C) Binding of TKPPR (SEQ ID NO: 2)-Beads to Endothelial Cells Under Flow

Coverslips containing confluent HAEC were mounted into a Bioptechs FCS2 parallel plate flow cell mounted on an Olympus IMT-2 inverted microscope. Typically, a silicon gasket was used which provided a 14-mm wide by 20-mm long perfusion area and which separated the glass plates by 0.25 mm. The temperature in the flow cell was maintained at 37° C. with a chamber controller. Coverslips were initially perfused with normal culture medium. Subsequently, the flow cell was perfused with bead solutions consisting of D-PBS containing 0.75 mM CaCl$_2$ and MgCl$_2$ and 0.1% of BSA and 1.95×10$^6$/mL of each bead type. A controlled-rate perfusion was achieved using a syringe pump (Harvard Equipment, model No. 901). The length of perfusion as well as any washes with D-PBS were varied as indicated. Wall shear stress T, in dynes/cm$^2$, was calculated using the equation (Lawrence et al., Blood 75:227-237, 1990):

$$T = \frac{3\mu Q}{2ba^2}$$

where µ is the coefficient of viscosity in poise (0.007, the viscosity of water, was used as an estimate), Q is the volumetric flow rate (cm$^2$/s), b is the channel width in cm (1.4 cm in our case), and a is the half channel height in cm (1.25×10$^{-2}$ cm unless otherwise indicated).

Bead binding of equal numbers of red fluorescent beads conjugated with TKPPR and green fluorescent beads conjugated with glycine was monitored after increasing lengths of perfusion and variable lengths of subsequent washing with the same solution lacking microspheres.

Results

The red TKPPR (SEQ ID NO: 2)-beads bound preferentially to the HAEC at 1.53 dynes/cm$^2$ (1.91 mL/min). The number of TKPPR (SEQ ID NO: 2) beads bound was significantly greater than the number of glycine (green) beads bound.

| Bead | Bound at 1.53 dynes/cm$^2$ |
|---|---|
| TKPPR (SEQ ID NO: 2) | 86 |
| Glycine | 10 |

Example 4

Preparation of DPPE-GLU-GTKPPR-OH (SEQ ID NO: 4)

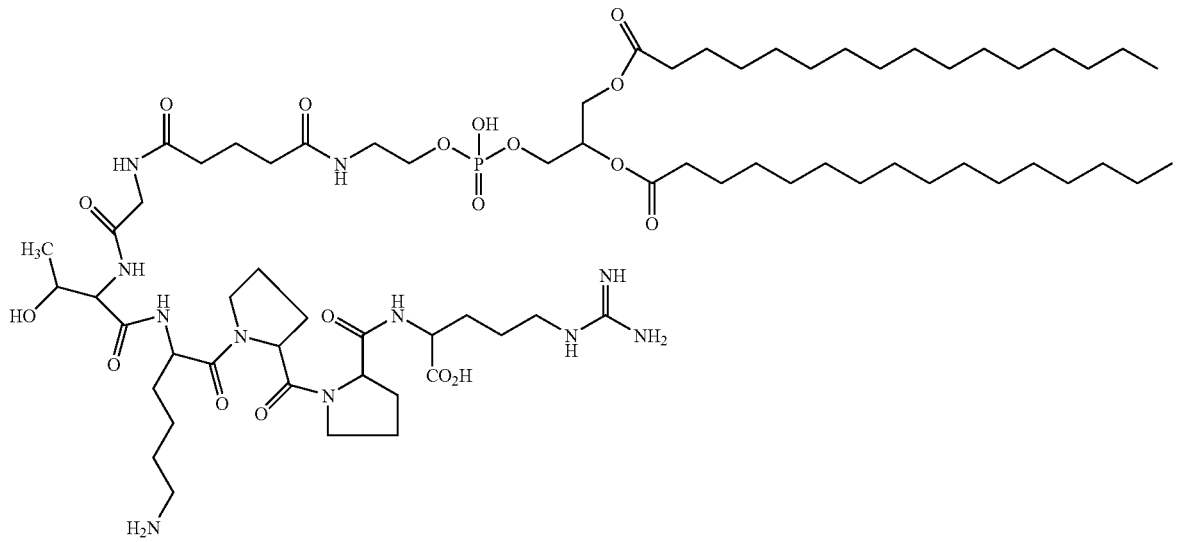

A) Preparation of Gly-Thr(Obzl)-Lys(Z)Pro-Pro-Arg(NO₂) Obzl (SEQ ID NO: 5)

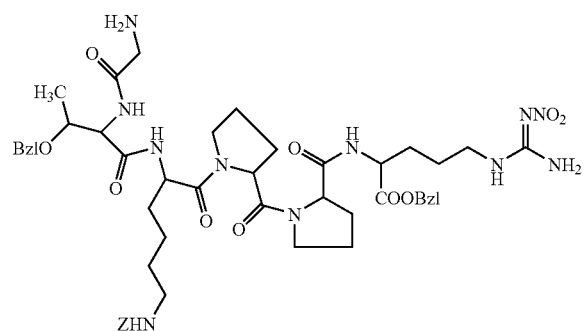

To a solution of Boc-glycine (commercially available) (368 mg, 2.1 mmol) in methylene chloride (20 mL) was added Thr(Obn)-Lys(Z)-Pro-Pro-Arg(NO₂)Obzl (SEQ ID NO: 2) (as prepared in Example 1)(2.1 g, 2 mmol) and the mixture was stirred for 5 min. This mixture was cooled to 5° C. and HATU (798 mg, 2.1 mmol) was added followed by diisopropylethylamine (1.05 g, 8.4 mmol). After stirring the reaction mixture for 4 h at room temperature, the solvents were removed in vacuo, the residue dissolved in ethyl acetate and washed with saturated sodium bicarbonate, sodium bisulphate and finally with water. The organic layer was dried and solvent removed to afford the coupled product. This was purified by column chromatography over silica gel (25 g) using 5% methanol in ethyl acetate as the eluent. Fractions containing the pure material were combined and solvent removed to obtain the pure product (1.9 g, yield 86%). A solution of this protected hexa-peptide (1.11 g, 1 mmol) in methylene chloride (1.5 mL) was added TFA (1.5 mL) and the mixture stirred for 1 hr at room temperature. TFA and methylene chloride were removed in vacuo and the residue stirred with anhydrous ether for 15 min. The precipitated solid was collected and dried to afford 1.05 g of the title compound.

| | |
|---|---|
| Yield: | 94.5% |
| HPLC: | 100% |
| Retention Time: | 15.96 min. |
| Column: | YMC, C-18 (4.6 × 250 mm) |
| Solvent: | Water-Acetonitrile, both containing 0.1% TFA |
| Elution condition: | Initial, 20% acetonitrile, linear gradient to 100% acetonitrile in 30 min |
| Flow rate: | 1.0 mL/min. |
| Detection: | UV 254 nm. |

$^1$H-NMR, and HRMS spectra are consistent with the structure

B) Preparation of N-Glutaroyl-Gly-Thr(Obzl)Lys(Z)-Pro-Pro-Arg(NO₂)Obzl (SEQ ID NO: 4)

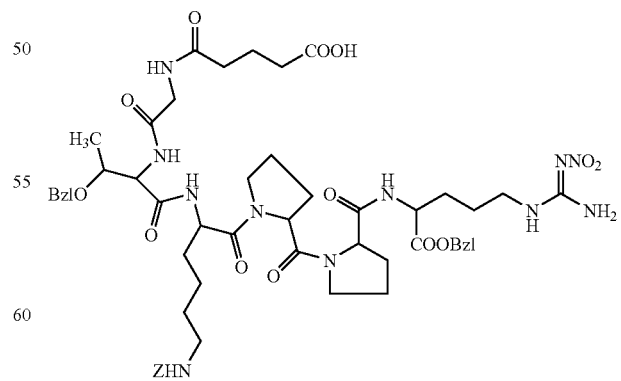

To a solution of Gly-Thr(Obzl)-Lys(Z)-Pro-Pro-Arg(NO₂) Obzl (SEQ ID NO: 5) (13 g, 1 mmol) in pyridine (5.0 mL) was added glutaric anhydride (110 mg, 1.0 mmol) and the mixture was stirred for 16 h. Pyridine was removed in vacuo, the residue dissolved in ethyl acetate and washed with water, 10% aq. HCl and finally with water. The organic layer was dried and solvent removed to afford 1.2 g of the required material.

| | |
|---|---|
| Yield: | 95.6% |
| HPLC: | 97.7% |
| Retention Time: | 18.40 min. |
| Column: | YMC, C-18 (4.6 × 250 mm); |
| Solvent: | Water-Acetonitrile, both containing 0.1% TFA |
| Elution condition: | Initial, 20% acetonitrile, linear gradient to 100% acetonitrile in 30 min |
| Flow rate: | 1.0 mL/min. |
| Detection: | UV 254 nm. |

$^1$H-NMR, and HRMS spectra are consistent with the structure

C) Preparation of DPPE-Glutaroyl-Gly-Thr(Obzl)-Lys(Z)-Pro-Pro-Arg(NO$_2$)Obzl (SEQ ID NO: 4)

| | |
|---|---|
| Yield: | 73% |
| HPLC: | 100% |
| Retention Time: | 14.25 min |
| Column: | YMC, C-4 (4.6 × 250 mm) |
| Solvent: | Water-Acetonitrile, both containing 0.1% TFA |
| Elution condition: | Initial, 80% acetonitrile, linear gradient to 100% acetonitrile in 20 min |
| Flow rate: | 1.0 mL/min |
| Detection: | UV 254 nm |

Elemental Analysis:

| | C | H | N | O | P |
|---|---|---|---|---|---|
| Calcd. | 59.53 | 8.20 | 9.06 | 21.55 | 1.67 |
| Found | 59.72 | 7.93 | 8.58 | | |

$^1$H-NMR, and HRMS spectra are consistent with the structure

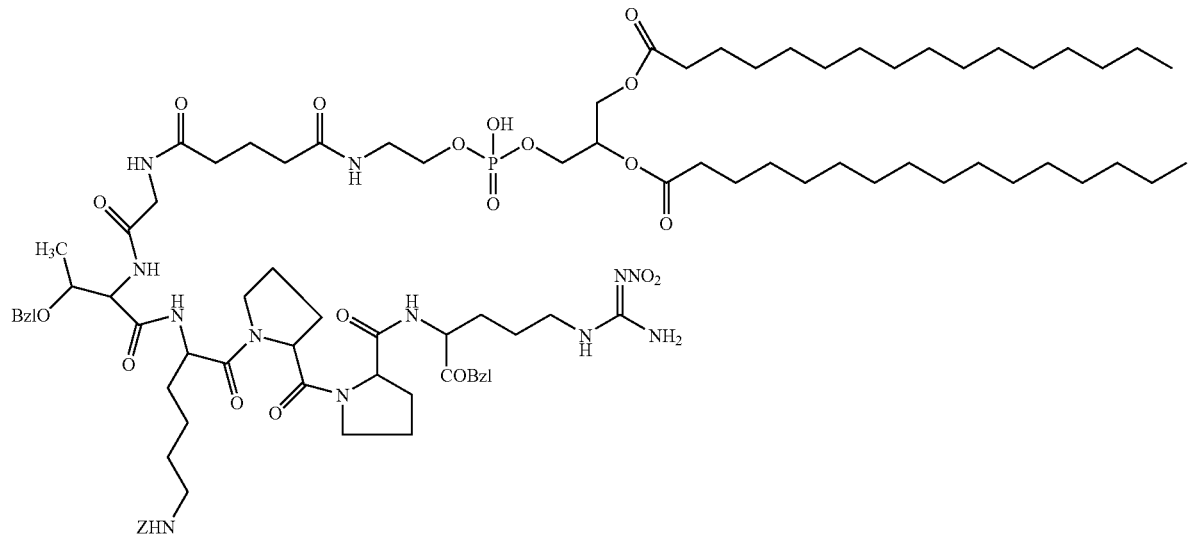

To a suspension of dipalmitoyl phosphatidyl ethanolamine (commercially available), (242 mg, 0.35 mmol) in methylene chloride (1.0 mL) was added TFA (200 □l) and the clear solution thus obtained was evaporated and dried under vacuo for 30 minutes. This was then redissolved in anhydrous methylene chloride (2.0 mL) and added to a solution of N-glutaroyl-Gly-Thr(Obzl)-Lys(Z)-Pro-Pro-Arg(NO$_2$)Obzl (SEQ ID NO: 4) (394 mg, 0.35 mmol) in methylene chloride (3.0 mL). After stirring the mixture for 10 min, HATU (142 mg, 0.37 mmol) followed by diisopropylethylamine (105 mg) were added and the stirring continued for 6 h at room temperature. The solvents were removed in vacuo, the residue dissolved in ethyl acetate, washed with saturated sodium bicarbonate, sodium bisulphate and finally with brine. The organic layer was dried and solvent removed to afford the coupled product. This was purified by column chromatography over silica gel (10 g) using 10% methanol in methylene chloride as the eluent. Fractions containing the pure material were combined and solvent removed to obtain 455 mg of the pure product.

D) Preparation of DPPE-Glutaroyl-Gly-Thr-Lys-Pro-Pro-Arg-OH (SEQ ID NO: 4) (DPPE-GLU-GTKPPR) (SEQ ID NO: 4)

To a solution of the compound prepared in previous step C??) (220 mg, 0.122 mmol) in methanol (15 mL), ethyl acetate (5.0 mL) and acetic acid (2.0 mL) was added Pd(OH)$_2$ (Degussa type, 80 mg) and the mixture was hydrogenated at 50 psi for 48 hr. The catalyst was filtered off and the residue was triturated with anhydrous ether to obtain the crude product. This was further purified by preparative HPLC on a C-4 column using a water-acetonitrile gradient (80-100% acetonitrile in 20 min). Fractions containing pure compound were combined and lyophilized to afford 130 mg of the desired DPPE-GLU-GTKPPR (SEQ ID NO: 4).

| | |
|---|---|
| Yield: | 74% |
| HPLC: | 100% |
| Retention Time: | 8.8 min. |
| Column: | YMC, C-4 (4.6 × 250 mm) |

-continued

| | Solvent: | Water-Acetonitrile, both containing 0.1% TFA |
|---|---|---|
| | Elution condition: | Isocratic, 80% acetonitrile and 20% water |
| | Flow rate: | 1.0 mL/min. |
| | Detection: | UV 220 nm |

Elemental Analysis:

| | C | H | N | O | P |
|---|---|---|---|---|---|
| Calcd. | 51.53 | 7.95 | 8.93 | 23.12 | 1.80 |
| Found | 51.04 | 8.07 | 8.91 | | |

$^1$H-NMR, and HRMS spectra are consistent with the structure

According to the same procedure G-TKPPR (SEQ ID NO: 5) was conjugated to the following phospholipids: DPPG dipalmitoylphosphatidyl glycerol through an ester bond instead of an amide bond; or DPPA dipalmitoylphosphatidic acid.

Example 5

Preparation of Gas-Filled Microbubble Compositions for Ultrasonic Echography Containing DPPE-Glu-GTKPPR (SEQ ID NO: 4)

A series of aqueous phospholipid suspensions were prepared with the following compositions:

A. 50 mg of DPPS, 2.5 mg of DPPE-Glu-GTKPPR (SEQ ID NO: 4), 1.5 g of glycerol and 5 g of propylene glycol;
B. 50 mg of DPPG, 150 mg of Pluronic® F68, 2.5 mg of DPPE-Glu-GTKPPR (SEQ ID NO: 4) and 4 g of glycerol;
C. 10 mg of DPPE-PEG2000, 30 mg of DAPC, 10 mg of DSPG, 2.5 mg of DPPE-Glu-GTKPPR (SEQ ID NO: 4), 3 g of glycerol and 3 g of propylene glycol;
D. 40 mg of DSPC, 10 mg of DPPA, 2.5 mg of DPPE-Glu-GTKPPR (SEQ ID NO: 4) and 3 g of lactose;
E. 100 mg of hydrogenated soy lecithin/dicetylphosphate (molar ratio 9:1), 2 mg of DPPE-Glu-GTKPPR (SEQ ID NO: 4) and 1.2 g of maltose
F. 100 mg of dimyristoylphosphatidylcholine (DMPC)/dipalmitoylphosphatidic acid (DPPA)/stearic acid (molar ratio 8:1:1), 2 mg of DPPE-Glu-GTKPPR (SEQ ID NO: 4) and 1.2 g of lactose
G. 40 mg of DPPC, 10 mg of DPPS, 2 mg of DPPE-Glu-GTKPPR (SEQ ID NO: 4) and 3 g of PEG 4000
H. 40 mg of DPPS, 10 mg of DSPC, 2 mg of DPPE-Glu-GTKPPR (SEQ ID NO: 4) and 3 g of PEG 4000
I. 25 mg of DSPC, 25 mg of DPPG, 1 mg of DPPE-Glu-GTKPPR (SEQ ID NO: 4), 5 mg of palmitic acid and 3 g of PEG4000.
J. 30 mg of DSPC, 10 mg of DPPA, 10 mg of DPPE-PEG2000, 1 mg of DPPE-Glu-GTKPPR (SEQ ID NO: 4) and 3 g of PEG 4000

The components of the each composition (from A to D) were dispersed in 20 mL of distilled water by heating at 70° C. and then extruded 3 times through 0.2 μm polycarbonate membranes (Nuclepore®). The resulting suspensions were treated according to the following process to generate gas microbubbles:

Suspension A: was homogenized under high speed mechanical agitation using Polytron® (12'000 rpm and 2 min.) under $C_4F_{10}$ gas;

Suspension B: 5 mL of the suspension was agitated vigorously using a two-syringe system (each syringe with a volume of 10 mL: one syringe contained 5 mL of the suspension and the other was filled with 0.5 mL of $C_4F_{10}$. The two syringes were connected by a three-way stopcock and were pumped energetically the two syringes in opposite directions (20 times for each syringe).

Suspension C: 1 mL of the suspension was placed in a 2-mL vial sealed with an airtight septum cap. The top air phase of the vial was evacuated and filled with $C_4F_{10}$. The sample vial was then vortexed using a vortexer (Mini-Bead Beater™, Biospec Products) at 3000 rpm for a duration of 2 minutes.

Suspension D: was frozen at −45° C. and lyophilized under a reduced pressure of 20 mbar; 1 g of the resulting powder was introduced into a vial, briefly put under vacuum (to eliminate air) then exposed to $C_3F_8$ and finally reconstituted with 10 mL of water.

Suspension E: Liposomes (50 mg/ml) were prepared in distilled water by the REV method (F. Szoka et al. PNAS USA 75 (1978) 4194). After extrusion through 1 μm polycarbonate filter, 2 mL of the preparation was mixed with 8 mL of a 15% maltose solution in distilled water. The resulting solution was frozen at −30° C. and lyophilized under 0.1 Tor. Thereafter atmospheric pressure was restored with perfluoropropane ($C_3F_8$). The resulting powder was then reconstituted with 10 ml of water.

Suspension F: same as with suspension E but lactose was used instead of maltose.

Suspensions G to J: the lipids were first dissolved in tertiary butanol (25 mL). The solution was then frozen at −45° C. and lyophilized under a reduced pressure of 20 mbar; 1 g of the resulting powder was introduced into a vial, briefly put under vacuum (to eliminate air) then exposed to $C_3F_8$ (suspension G), to $C_4F_{10}$ (suspension H), $C_4F_{10}$ or $C_3F_8$/air mixture (suspension I), $SF_6$ (suspension J) and finally reconstituted with 10 mL of water. The mixtures with air in suspension (I) were constituted by the following percentages: $C_4F_{10}$ or $C_3F_8$ 35, 50, 66% and the rest air.

All of these suspensions became milky and opaque after reconstitution or agitation. The resulting gas microbubbles were counted using a Coulter Multisizer. Gas microbubbles were observed with a size varying from 1 to 15 μm and a concentration varying from $10^7$ to $10^9$ per mL according to the type of suspension and the method of activation.

Example 6

Preparation of Gas-Filled Microbubbles Composition for Ultrasonic Echography not Containing DPPE-Glu-GTKPPR (SEQ ID NO: 4)

The compositions of Example 5 may be repeated exactly as described before except that no DPPE-GTKPPR (SEQ ID NO: 5) is added for all lipid preparations. Similar results of the bubble concentration may be obtained from Coulter Multisizer analysis.

Example 7

Evaluation of the Interaction of the Gas-Filled Microbubbles Compositions of Example 5 with HAEC in Static Culture A) Cell Culture Cells were seeded at 12,000 cells per cm into 8-well collagen I-coated chamber slides (Becton Dickinson,) or onto 48-well collagen I-coated microtiter plates (Becton Dickinson).

B) Immunofluorescence

Post-confluent (8-14 days in culture) HAEC may be fixed and stained for VWF and VE-cadherin as described in example 2.

C) TKPPR (SEQ ID NO: 2)-Conjugated Bubble Binding in Static Culture

Vials of the compositions of example 5 and of example 6 may be reconstituted with 5 mL of sterile saline, injected using a 20-gauge 1.5 inch needle. Bubbles may be then formed within the vials by shaking by hand vigorously for 30 seconds. 1 to 5 mL of the bubble formulation may be removed from each vial and diluted with 3 volumes of D-PBS (without calcium or magnesium) within 1 hour of use. Immediately prior to use, the diluted bubble solutions may be diluted again with an equal volume of D-PBS containing 0.2% BSA with or without added competing compounds.

Chamber slides containing confluent HAEC may be drained of culture medium, which was immediately replaced with one of the final bubble solutions prepared above. The wells may be slightly overfilled such that the liquid meniscus protrudes slightly above the plastic well-forming scaffold of the slide. Bubble solutions may be only added to alternate wells to minimize liquid cross-talk. The wells may be sealed with a piece of Parafilm and the slide incubated 20 minutes, inverted (according to Klibanov A. L., Advanced drug Delivery Reviews, 37, 1999, 139-157) to allow the bubbles to rise and make contact with the cells, after which the solutions may be poured off. Weakly associated bubbles may be removed by washing each well twice with 0.5 mL of D-PBS, swirling gently each time before pouring off. Additional D-PBS (0.5 mL) may be added to wells after the washes to keep the cells submerged until microscopic evaluation.

Bubbles from compositions of Example 5 may remain bound in large numbers to endothelial cells even after washing several times with buffer. The compositions of Example 5 without the targeting moiety may not remain attached to the HAEC after washing.

This association may be blocked with 10 to 100 μM free TKPPR (SEQ ID NO: 2) peptide.

Competition of binding of bubbles of compositions of Example 5 by free TKPPR (SEQ ID NO: 2) may be evaluated on multiple occasions.

The % inhibition data may clearly show that TKPPR (SEQ ID NO: 2)-bubbles bind to HAEC in a competitive manner. These data may be similar to those already described in Example 2.

Free tuftsin (TKPR) (SEQ ID NO: 1) also may inhibited TKPPR (SEQ ID NO: 2)-bubble compositions of example 5 binding to HAEC, but less effectively than free TKPPR (SEQ ID NO: 2).

Example 8

Evaluation of the Interaction of the Gas-Filled Microbubbles Compositions of Example 5 with HAEC Under Flow Cells may be seeded at 12,000 cells per $cm^2$ onto 40 mm diameter glass coverslips and grown as in Example 3. The protocol for exposure is the same as used in Example 3 except that the bubble containing solutions may be substituted for the bead suspensions and that initial binding of the bubbles may be achieved by inverting the flow chamber to allow the bubbles to come into contact with the cells as described in Example 7.

Perfusate solutions may be prepared by diluting a volume of reconstituted compositions of Example 5 in the formulation with 9 volumes of D-PBS containing 0.75 (mM) of $MgSO_4$ and $CaCl_2$.

The number of bubbles of compositions of Example 5 bound may increase with time for several minutes at a given flow rate, up to a flow rate producing 1.53 dynes/$cm^2$ of shear stress, although the binding capacity or binding saturation may be not determined. At 1.53 dynes/$cm^2$, bubbles (without the targeting moiety DPPE-Glu-GTKPPR (SEQ ID NO: 4) of Example 6) may not bind. However, once bound under a lesser flow rate (e.g. 1.53 dynes/$cm^2$), the shear stress on bubbles containing DPPE-Glu-GTKPPR (SEQ ID NO: 4) may be increased to 6.1 dynes/$cm^2$ without dislodging many of the bound bubbles.

Example 9

Evaluation of the Interaction of the Gas-Filled Microbubbles Compositions of Example 5 with RAEC in Static Culture Rabbit aortic endothelial cells (RAEC) from Biowhittaker (Cat No. AC-7018, lot 9CC086 from a custom isolation) may be obtained frozen on dry ice and stored in liquid nitrogen until thawing. RAEC may be cultured and used in bubble binding assays exactly as HAEC (described above), except that EGM2-MV medium (Biowhittaker Cat No. CC-3202) may be substituted for EGM-MV.

TKPPR (SEQ ID NO: 2) bubbles may bind well to aortic endothelial cells from rabbit, although cell to cell variability in binding is greater than with the lot of HAEC used in these studies. Nevertheless the data may demonstrate that the bubbles of compositions of Example 5 may be able to bind to RAEC and to be inhibited by free TKPPR (SEQ ID NO: 2) in a similar manner to the binding to HAEC.

Example 10

Evaluation of the Interaction of the Gas-Filled Microbubbles Compositions of Example 5 in KB Cells in Static Culture To determine whether TKPPR (SEQ ID NO: 2)-bubble binding is specific for endothelial cells, binding assays may be perform using KB cells, a human epidermoid carcinoma cell line. Human epidermoid carcinoma cells (KB cell line, ATCC 17-CCL, Batch F-12909) may be cultured as a monolayer in Minimum Essential Medium, formula 96-0373DJ from Gibco Life Technologies, at 37° C. in a humid incubator with a 5% $CO_2$ atmosphere.

Bubble binding was determined as previously described in Example 8.

The data may demonstrate that TKPPR (SEQ ID NO: 2)-bubbles bind preferentially to endothelial cells.

Example 11

TNFα (Tumor Necrosis Factor □) Activation of HAEC and Binding of TKPPR (SEQ ID NO: 2)-Bubbles Compositions of Example 5 Under Static Conditions To determine if activation of HAEC would enhance the binding of TKPPR (SEQ ID NO: 2)-bubbles, the cells may be treated with 0, 1, 5, or 10 ng/mL of TNFα for four hours prior to the binding assay. Bubble binding in each of the treated wells may then be compared with the untreated well, using the methods already described in Example 8.

The data may demonstrate that bubbles of compositions of Example 5 can distinguish stimulated from unstimulated endothelial cells.

Example 12

Inhibition of Bubbles of Compositions of Example 5 from Binding to HAEC in Static Culture by VEGF and Soluble KDR/Fc Chimera A) Cell Culture Cells may be seeded at 12,000 cells per cm$^2$ into 48-well collagen 1-coated microtiter plates (Becton Dickinson) as described in Example 2.

B) Inhibition of Bubble-Binding in Static Culture

Inhibition of bubble binding with $VEGF_{165}$ (Oncogene Research Products) and with soluble human KDR/Fc chimera (R&D Sytems Inc.) may be carried out using the protocol of Example 7.

VEGF potently may inhibit bubble binding. Soluble KDR/Fc chimera may also inhibit potently.

The combined results of inhibition with both VEGF and KDR/Fc may indicate that the bubbles interact with a VEGF receptor on HAEC, possibly KDR or more likely NP-1, which binds to KDR.

Example 13

Preparation of Gas-Filled Microbubble Composition for Ultrasonic Echography Containing 10% DPPE-Glu-GTKPPR (SEQ ID NO: 4)

The composition I of Example 5 was repeated exactly as described before except that 5 mg DPPE-GTKPPR (SEQ ID NO: 5) was added (instead of 2.5 mg) for all lipid preparations, yielding bubble compositions with 10% DPPE-GTKPPR (SEQ ID NO: 5). Similar results of the bubble concentration were obtained from Coulter Multisizer analysis.

Example 14

Evaluation of the Interaction of the Gas-Filled Microbubble Compositions with 1% and 5% DPPE-GTKPPR (SEQ ID NO: 5) with HAEC in Static A) Cell Culture Cells were seeded at 12,000 cells per cm$^2$ into 8-well collagen I-coated chamber slides (Becton Dickinson,) or onto 48-well collagen I-coated microtiter plates (Becton Dickinson).

B) Immunofluorescence

Post-confluent (8-14 days in culture) HAEC were fixed and stained for VWF and VE-cadherin as described in example 2.

C) TKPPR (SEQ ID NO: 2)-Conjugated Bubble Binding in Static Culture

Composition I of Example 5 was repeated exactly as described except that 0.5 mg DPPE-GTKPPR (SEQ ID NO: 5) was added (instead of 2.5 mg) yielding compositions with 1% DPPE-GTKPPR (SEQ ID NO: 5). Vials of this composition as well as that of composition I of Example 5 (5% DPPE-GTKPPR) (SEQ ID NO: 5) were reconstituted with 5 mL of sterile saline, injected using a 20-gauge 1.5 inch needle. Bubbles were then formed within the vials by shaking by hand vigorously for 30 seconds. 1 to 5 mL of the bubble formulation was removed from each vial and diluted with 3 volumes of D-PBS (without calcium or magnesium) within 1 hour of use. Immediately prior to use, the diluted bubble solutions were diluted again with an equal volume of D-PBS containing 0.2% BSA with or without added competing compounds.

Chamber slides containing confluent HAEC were drained of culture medium, which was immediately replaced with one of the final bubble solutions prepared above. The wells were slightly overfilled such that the liquid meniscus protruded slightly above the plastic well-forming scaffold of the slide. Bubble solutions were only added to alternate wells to minimize liquid cross-talk. The wells were sealed with a piece of Parafilm and the slide was incubated 20 minutes, inverted to allow the bubbles to rise and make contact with the cells, after which the solutions were poured off. Weakly associated bubbles were removed by washing each well twice with 0.5 mL of D-PBS, swirling gently each time before pouring off. Additional D-PBS (0.5 mL) was added to wells after the washes to keep the cells submerged until microscopic evaluation.

Results

Bubbles from composition I of Example 5 (5% DPPE-GTKPPR) (SEQ ID NO: 5) remained bound in large numbers to endothelial cells even after washing several times with buffer. The bubbles without the targeting moiety did not remain attached to the HAEC after washing.

| Composition | Bubbles bound |
| --- | --- |
| Composition I of Example 5 without targeting moiety | 203 |
| Composition I of Example 5 | 7053 |

This association was blocked with 10 to 100 μM free TKPPR (SEQ ID NO: 2) peptide.

| Composition | No competition | 10 μmol of TKPPR (SEQ ID NO: 2) | 100 μmol of TKPPR (SEQ ID NO: 2) |
| --- | --- | --- | --- |
| 1% Composition | 555 ± 83 | 96 ± 37 | 5 ± 1 |
| 5% Composition | 726 ± 17 | 865 ± 35 | 62 ± 38 |

In a side-by-side comparison of the compositions tested, 31% more bubbles were bound using the 5% composition, based on manual counting of the bubbles. In addition, 10 μM free TKPPR (SEQ ID NO: 2) was able to inhibit 82.7% of bubble binding using the 1% composition, but no inhibition by 10 μM free TKPPR (SEQ ID NO: 2) (19% more bubbles bound) was observed when the 5% composition was used.

Competition of binding of bubbles of the 1% composition by free TKPPR (SEQ ID NO: 2) was evaluated on multiple occasions.

| Free TKPPR (SEQ ID NO: 2) [μM] | Average % Inhibition |
|---|---|
| 5 | 45.7 |
| 10 | 79.6 |
| 25 | 82.0 |
| 50 | 92.7 |
| 100 | 93.7 |

Figure 6:
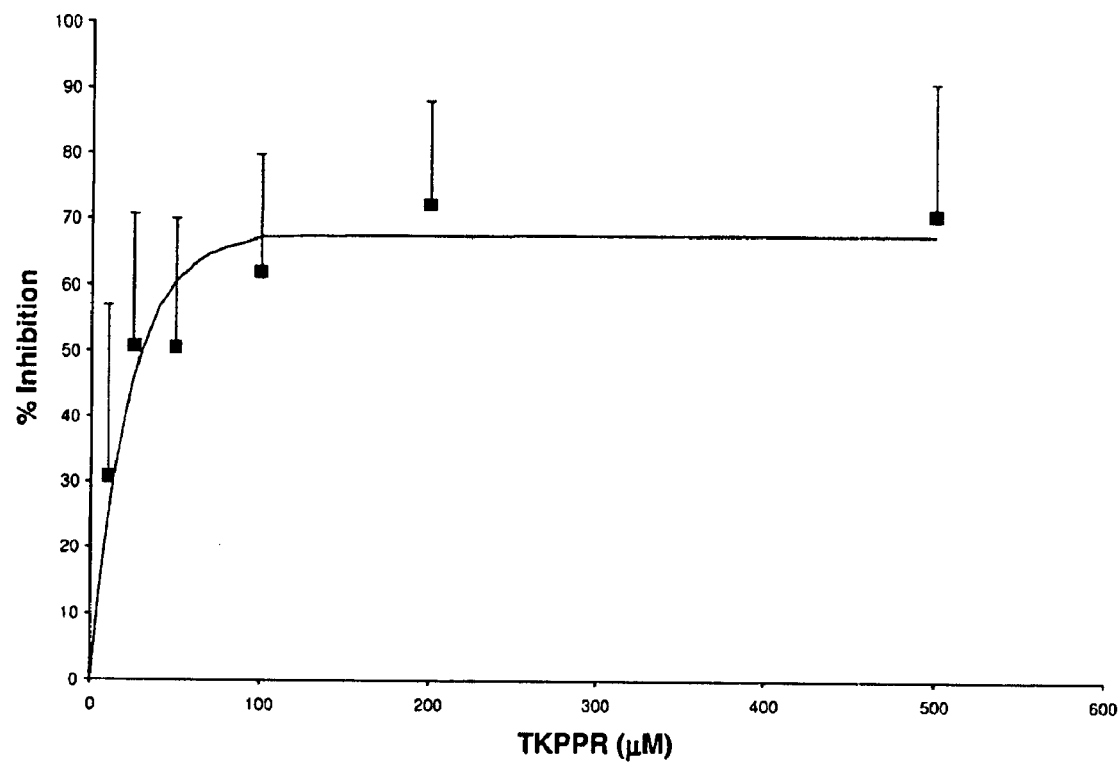
FIG. 6 demonstrates that the TKPPR (SEQ ID NO: 2)-bubbles bind to HAEC in a competitive manner.

The % inhibition data summarized in FIG. 6 clearly show that TKPPR (SEQ ID NO: 2)-bubbles bind to HAEC in a competitive manner, further illustrated in the chart below. These data are similar to those already described in Example 2.

Example 15

Evaluation of the Interaction of the 5% TKPPR(SEQ ID NO: 2) Gas-Filled Microbubble Composition (Composition I of Example 5) with HAEC Under Flow Cells were seeded at 12,000 cells per cm² onto 40 mm diameter glass coverslips and grown as in Example 3. The protocol for exposure was the same as used in Example 3 except that the bubble containing solutions were substituted for the bead suspensions and that initial binding of the bubbles was achieved by inverting the flow chamber to allow the bubbles to come into contact with the cells as described in Example 7.

Perfusate solutions were prepared by diluting a volume of reconstituted composition E of Example 5 and Example 6 in the formulation with 9 volumes of D-PBS containing 0.75 (mM) of $MgSO_4$ and $CaCl_2$.

Results

The number of bubbles (Composition I of Example 5) bound increased with time for several minutes at a given flow rate, up to a flow rate producing 1.53 dynes/cm² of shear stress, although the binding capacity or binding saturation were not determined. At 1.53 dynes/cm², bubbles (without the targeting moiety DPPE-Glu-GTKPPR) (SEQ ID NO: 4) did not bind. At 3.06 dynes/cm², 5% bubbles (Composition I of Example 5) did not bind. However, once bound under a lesser flow rate (e.g. 1.53 dynes/cm²), the shear stress on bubbles containing DPPE-Glu-GTKPPR (SEQ ID NO: 4) was increased to 6.1 dynes/cm² without dislodging many of the bound bubbles.

Example 16

Evaluation of the Interaction of the 5% TKPPR (SEQ ID NO: 2) Gas-Filled Microbubble Composition (Composition I of Example 5) with RAEC in Static Culture Rabbit aortic endothelial cells (RAEC) from Biowhittaker (Cat No. AC-7018, lot 9CC086 from a custom isolation) were obtained frozen on dry ice and stored in liquid nitrogen until thawing. RAEC were cultured and used in bubble binding assays exactly as HAEC (described above), except that EGM2-MV medium (Biowhittaker Cat No. CC-3202) was substituted for EGM-MV.

| Free TKPPR (SEQ ID NO: 2) (μM) | HAEC bubbles bound | RAEC bubbles bound |
|---|---|---|
| 0 | 1425 | 751 |
| 100 | 58 | 21 |

TKPPR (SEQ ID NO: 2) bubbles bound well to aortic endothelial cells from rabbit, although cell to cell variability in binding was greater than with the lot of HAEC used in these studies. The cells in the RAEC culture binding the fewest bubbles tended to be larger cells and elongated cells, more so than is typical for endothelial cells. Thus the heterogeneity in binding may have been due to contamination of the culture with non-endothelial cells. Nevertheless these data demonstrate that the 5% bubbles of composition I of Example 5 are able to bind to RAEC and to be inhibited by free TKPPR (SEQ ID NO: 2) in a similar manner to the binding to HAEC.

Example 17

Evaluation of the Interaction of the 5% TKPPR (SEQ ID NO: 2) Gas-Filled Microbubble Composition (Composition I of Example 5) with KB Cells in Static Culture To determine whether TKPPR (SEQ ID NO: 2)-bubble binding is specific for endothelial cells, binding assays were performed using KB cells, a human epidermoid carcinoma cell line. Human epidermoid carcinoma cells (KB cell line, ATCC 17-CCL, Batch F-12909) were cultured as a monolayer in Minimum Essential Medium, formula 96-0373DJ from Gibco Life Technologies, at 37° C. in a humid incubator with a 5% $CO_2$ atmosphere.

Bubble binding was determined as previously described in Example 7.

| HAEC bubble binding | KB cell bubble binding |
|---|---|
| 1118 ± 148 | 56 ± 10 |

These data demonstrate that TKPPR (SEQ ID NO: 2)-bubbles bind preferentially to endothelial cells.

Example 18

TNFα (Tumor Necrosis Factor α) Activation of HAEC and Binding of 5% TKPPR (SEQ ID NO: 2)-Bubbles (Composition I of Example 5) Under Static Conditions To determine if activation of HAEC would enhance the binding of TKPPR (SEQ ID NO: 2)-bubbles, the cells were treated with 0, 1, 5, or 10 ng/mL of TNFα for four hours prior to the binding assay. Bubble binding in each of the treated wells was then compared with the untreated well, using the methods already described in Example 6.

Results

| TNFα (ng/mL) | TKPPR (SEQ ID NO: 2)- Bubbles bound |
|---|---|
| 0 | 950 |
| 1 | 1,525 |
| 5 | 1,360 |
| 10 | 1,025 |

TNFα enhanced bubble binding at 1 ng/mL, this effect was reduced with 5 ng/mL TNFα, and essentially absent after treatment with 10 ng/mL. These data demonstrate that bubbles of composition I of Example 5 can distinguish stimulated from unstimulated endothelial cells.

Example 19

Inhibition of 5% TKPPR (SEQ ID NO: 2) Bubbles (Composition I of Example 5) from Binding to HAEC in Static Culture by VEGF and Soluble KDR/Fc Chimera A) Cell Culture Cells were seeded at 12,000 cells per cm² into 48-well collagen 1-coated microtiter plates (Becton Dickinson) as described in Example 2.

B) Inhibition of Bubble-Binding in Static Culture

Inhibition of bubble binding with $VEGF_{165}$ (Oncogene Research Products) and with soluble human KDR/Fc chimera (R&D Sytems Inc.) at the concentrations indicated below was carried out using the protocol of Example 6.

Results

| VEGF Added (ng/ml) | Bubbles Bound |
|---|---|
| 0* | 1246 ± 167 |
| 6.25 | 1184 ± 172 |
| 12.5 | 599 ± 6 |
| 25 | 342 ± 22 |
| 50 | 226 ± 39 |
| 75 | 190 ± 45 |

*same control

VEGF potently inhibited bubble binding with half-maximal inhibition at about 12.5 ng/mL (0.3 nM). Soluble KDR/Fc chimera also inhibited very potently.

| KDR/Fc Added (ng/ml) | Bubbles Bound |
|---|---|
| 0* | 1246 ± 167 |
| 125 | 1030 ± 12 |
| 250 | 786 ± 76 |
| 500 | 342 ± 78 |
| 1000 | 75 ± 5 |
| 2500 | 84 ± 3 |

*same control

Inhibition of 50% of maximal binding occurred at about 450 ng/mL (1.4 nM).

The combined results of inhibition with both VEGF and KDR/Fc indicate that the bubbles interact with a VEGF receptor on HAEC, possibly KDR or more likely the NP-1 receptor, which binds to KDR.

Example 20

Influence of Targeting Molecule Density on the Binding of Microbubble Compositions Containing DPPE-GTKPPR (SEQ ID NO: 5) (BRU 114) to HAEC in Static Culture The compositions were reconstituted and the assays were performed as described in Example 7 using microbubble compositions containing 1%, 5%, and 10% BRU-114 (Composition I of Example 5) as a % of total phospholipid in the composition Results As indicated in the table below, more bubbles from the 5% BRU-114 composition bound to HAEC than either the 1% or 10% composition. In addition, the 5% composition and the 10% composition required a higher concentration of free TKPPR (SEQ ID NO: 2) peptide to effectively block bubble binding to HAEC. Although fewer bubbles from the 10% composition bound to HAEC than the 5% composition, the bubbles from the 10% composition were the most resistant to inhibition by free TKPPR (SEQ ID NO: 2) peptide. These data indicate that targeted bubble binding is affected by the concentration of targeting molecule in the composition, with 5% of phospholipid providing the optimal balance of binding events and binding strength (as measured by resistance to inhibition by free ligand).

TABLE

Bubble Binding to HAEC- Effect of % targeting molecule in the composition on binding frequency and binding strength. % refers to % BRU-114 out of total phospholipid in the composition.

| Treatment | Bubbles Bound- 1% | Bubbles Bound- 5% | Bubbles Bound- 10% |
|---|---|---|---|
| None | 1640 | 2782 | 1858 |
| 10 microM TKPPR (SEQ ID NO: 2) | 10 | 1345 | 1093 |
| 50 microM TKPPR (SEQ ID NO: 2) | 5 | 440 | 857 |
| 100 microM TKPPR (SEQ ID NO: 2) | 4 | 12 | 399 |
| 200 microM TKPPR (SEQ ID NO: 2) | 4 | 13 | 66 |

Example 21

Evaluation of the Ability of Linear and Cyclic CTKPPRC (SEQ ID NO: 6) (BRU-305 and BRU-306) to Inhibit the Binding of Composition I of Example 5 (BRU 114) to HAEC in Static Culture Assays were performed as described for Example 7 using microbubble compositions containing 2% BRU-114 (Composition I of Example 5) as a % of total phospholipid in the composition.

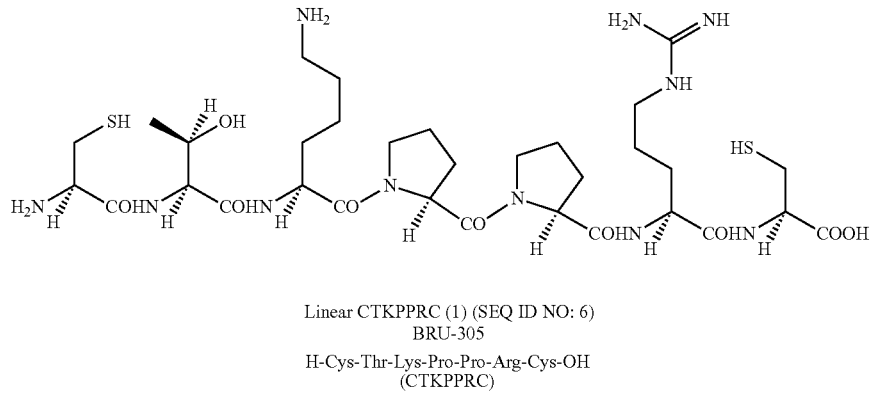

Linear CTKPPRC (1) (SEQ ID NO: 6)
BRU-305
H-Cys-Thr-Lys-Pro-Pro-Arg-Cys-OH
(CTKPPRC)

Synthesis of Linear and Cyclic CTKPPRC (SEQ ID NO: 6) (BRU-305 and BRU-306):

Experimental

General Methods for Solid Phase Peptide Synthesis (SPPS)

The linear peptide CTKPPRC (SEQ ID NO: 6) was synthesized by established automated protocols on an Advanced ChemTech Automated 496 Peptide Synthesizer using Wang resin (0.6 mmol/g), Fmoc-protected amino acids and DCI-mediated HOBt ester activation in NMP. Side-chain protected amino acids used in this study were: Fmoc-Cys(Trt)-OH, Fmoc-Arg(Pmc)-OH, Fmoc-Pro-OH, Fmoc-Lys(Boc)-OH and Fmoc-Thr(But)-OH. The peptide sequence on the Wang resin was synthesized in stepwise fashion by SSPS methods typically on a 0.5 mmol scale. The solid support was Wang resin preloaded with Fmoc-Cys(Trt)-OH. The amino acid coupling was carried out with a 4-fold excess each of amino acid and DIC-HOBt reagent in NMP (10 mL/g resin). The cleavage of the Fmoc-group was performed with 25% piperidine in DMF (10 mL/g resin) for 3 min followed by a second treatment with 25% piperidine in DMF (10 mL/g resin) for 10 min. After completion of the peptide synthesis, the resin was treated with the cleavage cocktail, "reagent B" (TFA:Water:phenol:Triisopropylsilane, 88:5:5:2) (10 mL/g resin) for 4 h. After evaporation of the volatiles under vacuum, the paste thus obtained was triturated with ether to provide a solid which was washed with ether (3×20 mL) by centrifugation and then dried under vacuum to obtain the required peptide as an off-white solid The aqueous solution containing the peptide was loaded onto a reversed phase C18 preparative column (YMC, 10×250 mm, 10μ 120 Å) which was equilibrated with acetonitrile (2%)-water with TFA (0.1%). The column was then eluted with water-acetonitrile solvent mixture (flow rate 10 mL/min), starting a linear gradient from 10% acetonitrile to 50% acetonitrile in 60 min and fractions (5 mL size) were collected. Each fraction was analyzed on an analytical reversed phase C18 column and fractions containing the product in >99% purity were pooled and freeze-dried to provide the pure peptide as a colorless fluffy solid.

Following the general procedure as outlined above, the linear peptide CTKPPRC (SEQ ID NO: 6) (1) was synthesized in 45% yield as colorless fluffy solid.

MS (ES$^+$): 804.3 (M+H)$^+$; 402.9 (doubly charged); 268.9 (triply charged).

$^1$H NMR (D$_2$O): δ 1.15 (d, 3H, Thr-CH$_3$), 1.30-1.45 (m, 2H), 1.53-1.67 (m, 5H), 1.70-2.05 (m, 9H), 2.24-2.38 (m, 2H), 2.83-2.95 (m, 4H), 2.98-3.12 (m, 2H), 3.18 (t, 2H), 3.52-3.64 (m, 2H), 3.21-3.81 (m, 2H), 4.05 (q, 1H), 4.27 (m, 3H), 4.38 (m, 1H), 4.48 (m, 1H), 4.62 (t, 1H) and 4.69 (t, 1H).

HPLC: Retention Time 17.03 min; Assay: >99% (area %); Column: YMC, C18; 0.46×25 cm; solvent: Water (0.1% TFA)-Acetonitrile (0.1% TFA), Initial condition: 2% acetonitrile; Linear Gradient Elution to 45% acetonitrile in 47 min; Flow rate: 1 mL/min; Detection: 220 nm

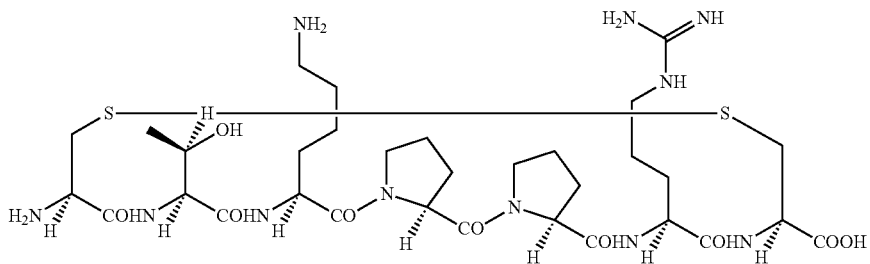

Cyclic disulfide CTKPPRC (2) (SEQ ID NO: 6)
BRU-306

H-Cys-Thr-Lys-Pro-Pro-Arg-Cys-OH (CTKPPRC)

Cyclic disulfide CTKPPRC (SEQ ID NO: 6) (2) was prepared from the corresponding linear peptide by air oxidation in water-DMSO (5%). About 20 mg of the linear peptide 1 was dissolved in water-DMSO (5%) (200 mL, 1 mg/10 mL of water) and the pH of the solution was adjusted to 8.5 with NH$_4$OH (1.0 N). The solution was taken up in a wide mouth beaker and stirred for 24 h at room temperature. After neutralization with dil. HCl, the solution was loaded onto a reversed phase C18 preparative column (YMC ODS, 20×250 mm, 10μ 120 Å) pre-equilibrated with 5% acetonitrile in water (0.1% TFA). The compound was eluted from the column using a linear gradient of acetonitrile into water (both containing 0.1% TFA), starting at 10% acetonitrile and ramping to 50% acetonitrile in 60 min. The fractions (10 mL size) were analyzed on a YMC ODS analytical reversed phase C-18 column (10μ, 120 Å) and fractions containing the product in >99% purity were pooled and freeze-dried to afford the title compound 2 (15 mg, 75% yield) as a fluffy colorless solid.

MS (ES$^+$): 802.3 (M+H)$^+$; 401.7 (doubly charged); 268.2 (triply charged)

$^1$H NMR (D$_2$O): δ 1.18 (d, 3H, Thr-CH$_3$), 1.31-1.48 (m, 2H), 1.51-1.68 (m, 7H), 1.71-2.04 (m, 8H), 2.18-2.35 (m, 3H), 2.83-2.94 (m, 2H), 3.05 (m, 1H), 3.15 (m, 2H), 3.26 (m, 2H), 3.42-3.61 (m, 5H), 4.21 (m, 2H), 4.30 (m, 3H), 4.45 (m, 2H) and 4.51 (m, 1H).

HPLC: Retention Time 14.90 min; Assay: >99% (area %); Column: YMC, C18; 0.46×25 cm; solvent: Water (0.1% TFA)-Acetonitrile (0.1% TFA), Initial condition: 2% acetonitrile; Linear Gradient Elution to 32% acetonitrile in 30 min; Flow rate: 1 mL/min; Detection: 220 nm.

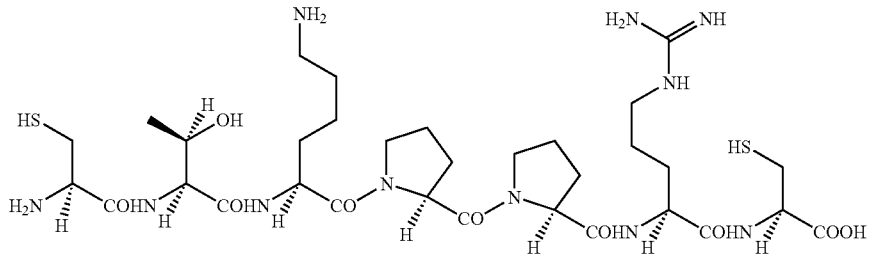

1

H-Cys-Thr-Lys-Pro-Pro-Arg-Cys-OH
(CTKPPRC)

Air Oxidation

Conc.-1 mg in 10 mL of
5% DMSO in water
24 h, RT

-continued

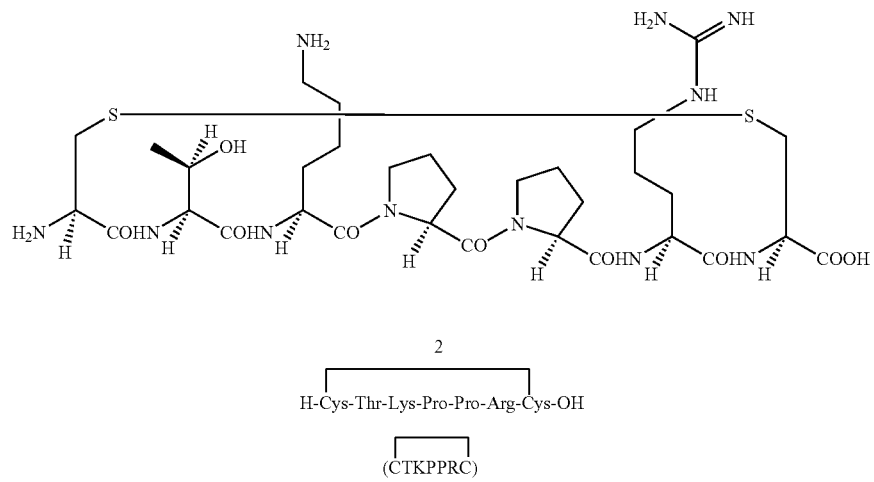

2

H-Cys-Thr-Lys-Pro-Pro-Arg-Cys-OH (CTKPPRC)

Results:

As indicated in the table below, compositions containing linear CTKPPRC (SEQ ID NO: 6) (BRU-305) or cyclized CTKPPRC (SEQ ID NO: 6) (BRU-306) had no ability to block the binding of microbubbles containing BRU-114 in their composition to HAEC. This data provides further evidence of a specific interaction between TKPPR (SEQ ID NO: 2) and the endothelial cell receptor.

TABLE

Bubble Binding to HAEC- Effect of competition with linear CTKPPRC (SEQ ID NO: 6) (BRU-305), cyclized CTKPPRC (SEQ ID NO: 6) (BRU-306), and TKPPR (SEQ ID NO: 2) (BRU-95) on binding frequency. Binding is represented as % of control binding in the absence of competing peptides.

| Treatment | Bubbles Bound % |
|---|---|
| None | 100 |
| 25 microM TKPPR (SEQ ID NO: 2) | 16 |
| 50 microM BRU-305 | 97 |
| 100 microM BRU-305 | 78 |
| 200 microM BRU-305 | 88 |
| 50 microM BRU-306 | 97 |
| 100 microM BRU-306 | 71 |
| 200 microM BRU-306 | 99 |

Example 22

Evaluation of the Ability of Tuftsin (TKPR) (SEQ ID NO: 1) to Inhibit the Binding Composition I of Example 5 (BRU 114) to HAEC in Static Culture Compositions were reconstituted and assays were performed as described in Example 7 using microbubble compositions containing 1% BRU-114 (Composition I of Example 5) as a % of total phospholipid in the composition.

Results:

As indicated in the table below, TKPR (SEQ ID NO: 1) (Tuftsin) is less potent than TKPPR (SEQ ID NO: 2) (BRU-95) at inhibiting the binding of microbubbles containing BRU-114 (Composition I of Example 5) in their composition to HAEC.

TABLE

Bubble Binding to HAEC- Effect of competition TKPR (Tuftsin) and TKPPR (BRU-95) on binding frequency. Binding is represented as average total bubbles bound (of duplicate measurements).

| Treatment | Bubbles Bound |
|---|---|
| None | 737 |
| 5 microM TKPPR (SEQ ID NO: 2) | 790 |
| 10 microM TKPPR (SEQ ID NO: 2) | 528 |
| 25 microM TKPPR (SEQ ID NO: 2) | 106 |
| 50 microM TKPPR (SEQ ID NO: 2) | 56 |
| 100 microM TKPPR (SEQ ID NO: 2) | 17 |
| 5 microM TKPR (SEQ ID NO: 1) | 1152 |
| 10 microM TKPR (SEQ ID NO: 1) | 976 |
| 25 microM TKPR (SEQ ID NO: 1) | 1171 |
| 50 microM TKPR (SEQ ID NO: 1) | 904 |
| 100 microM TKPR (SEQ ID NO: 1) | 556 |

Example 23

Synthesis of DPPE-Glu-DI(AMINODIOXAOCTANOYL)-TKPPR-OH (SEQ ID NO: 4) (BRU-292)

Synthetic scheme:

FLOW SHEET
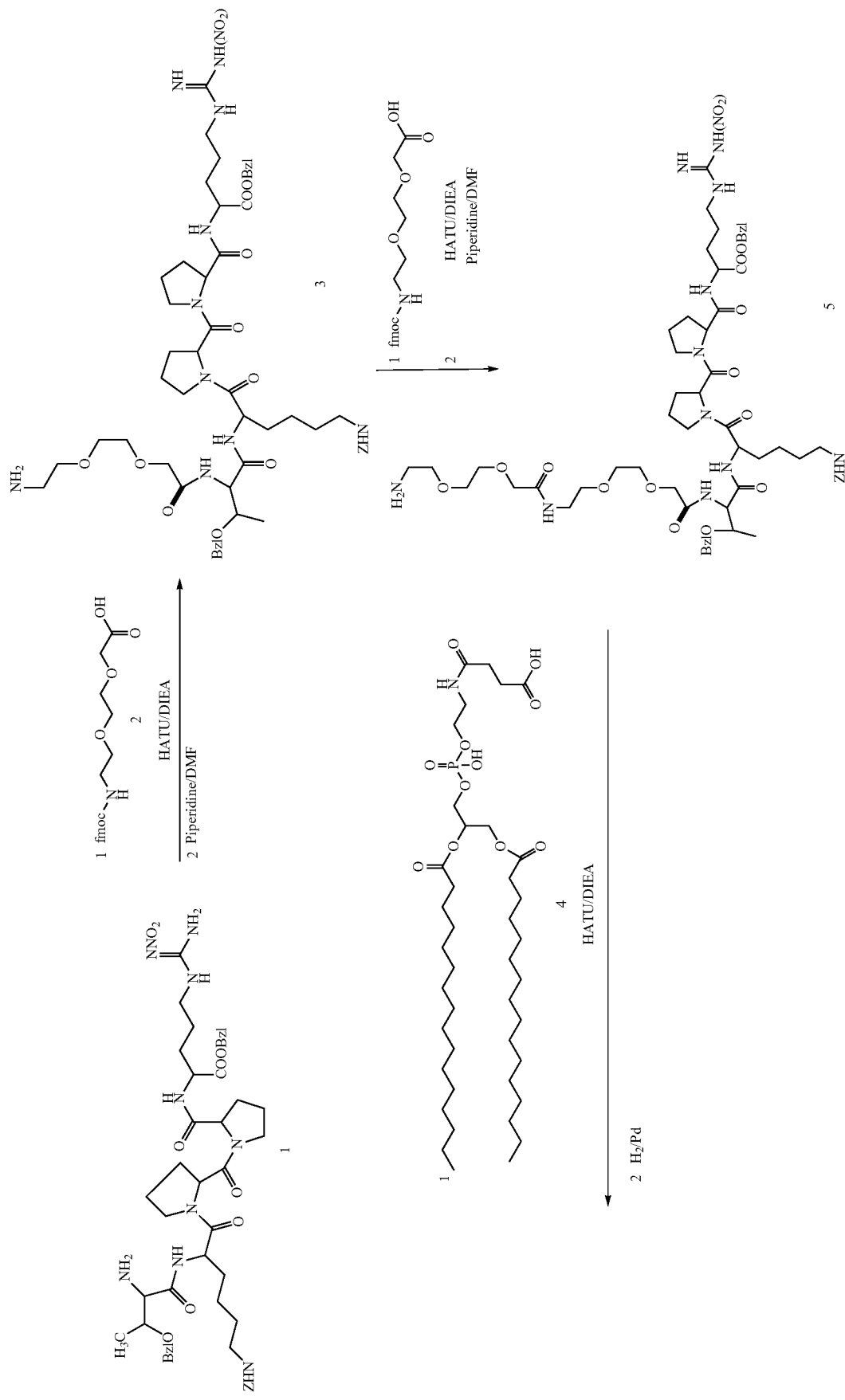

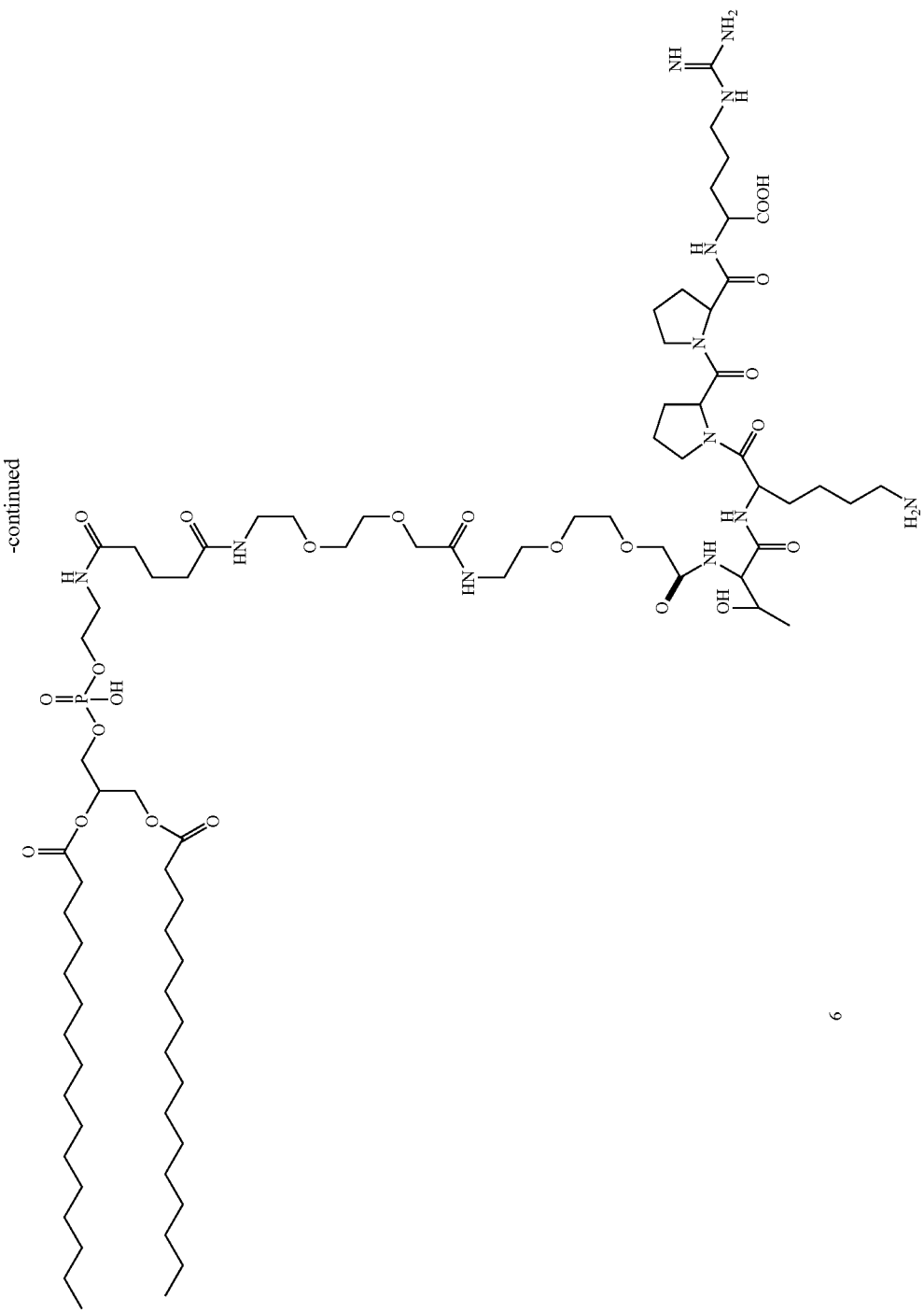

Experimental

Preparation of Aminodioxaoctanoyl-Thr(OBnzl)-Lys(Z)Pro-Pro-Arg(NO$_2$)Obzl (3) (SEQ ID NO: 2)

To a solution of Fmoc-aminodioxaoctanoic acid (2) (400 mg, 1.1 mmol) in methylene chloride (20 mL) was added Thr(OBzl)-Lys(Z)-Pro-Pro-Arg(NO$_2$)OBzl (SEQ ID NO: 2) (1.07 g, 1 mmol) and the mixture was stirred for 5 min. This mixture was cooled to 5° C. and HATU (400 mg, 1.1 mmol) was added followed by diisopropylethylamine (282 mg, 2.2 mmol). After stirring the reaction mixture for 4 h at room temperature, the solvents were removed in vacuo, the residue dissolved in ethyl acetate (50 mL) and washed with saturated sodium bicarbonate (3×25 mL), sodium bisulphate (2×25 mL) and finally with water (25 mL). The organic layer was dried and the solvent removed to obtain the coupled product as a colorless glassy solid (1.35 g). This was purified by column chromatography over silica gel (30 g) using 5-10% methanol in methylene chloride as the eluent. Fractions containing the material were combined and the solvent removed to obtain the pure product (1.01 g, yield 82%). To a solution of this protected peptide (950 mg, 0.72 mmol) in methylene chloride (1.5 mL) was added 20% piperidine in acetonitrile (20 mL) and the mixture was stirred for 1 h at room temperature. The solvents were removed and the residue was triturated with hexane (3×50 mL) and dried. This was purified by column chromatography over silica gel (15 g) using 5-10% methanol in methylene chloride as the eluent. Fractions containing the material were combined and the solvent removed to obtain the pure product (690 mg, yield 87%).

HPLC: Retention Time 15.74, Column: YMC, C-18 (4.6×250 mm); Solvent: Water-Acetonitrile, both containing 0.1% TFA:, Elution condition: Initial, 20% acetonitrile, linear gradient to 100% acetonitrile in 30 min; Flow rate: 1.0 mL/min.; Detection, UV 254 nm $^1$HNMR: (DMSO) δ 1.10 (d, J=5.5 Hz, 3H, CH$_3$), 1.21-2.20 (m, 18H, CH$_2$), 2.95 (bs, 2H, CH$_2$), 3.12 (bs, 2H, CH$_2$), 3.50-3.75 (m, 4H, NCH$_2$), 4.10-4.55 (m, 6H, OCH$_2$, NCH, NHCH, H$_2$NCH), 4.99 (s, 2H, benzylic CH$_2$), 5.10 (dd, 2H, benzylic CH$_2$) 7.28-7.42 (m, 15H, ArH), 7.95-8.50 (m, 6H, NH)

Mass Spectrum: 1102.6 (M+H)$^+$

Preparation of Di(aminodioxaoctanoyl)-Thr(OBzl)-Lys(Z)Pro-Pro-Arg(NO$_2$)OBzl (4) (SEQ ID NO: 2)

To a solution of Fmoc-aminodioxaoctanoic acid (2) (156 mg. 0.4 mmol) in methylene chloride (10 mL) was added aminodioxaocta-Thr(OBzl)-Lys(Z)-Pro-Pro-Arg(NO$_2$)Obzl (SEQ ID NO: 2) (400 mg, 0.36 mmol) and the mixture was stirred for 5 min. This mixture was cooled to 5° C. and HATU (160 mg, 0.4 mmol) was added followed by diisopropylethylamine (131 mg, 0.1 mmol). After stirring the reaction mixture for 6 h at room temperature, the solvents were removed in vacuo, the residue dissolved in ethyl acetate (50 mL) and washed with saturated sodium bicarbonate (3×25 mL), sodium bisulphate (2×25 mL) and finally with water (25 mL). The organic layer was dried and solvent removed to obtain the coupled product as a colorless glassy solid (510 mg). This was purified by column chromatography over silica gel (20 g) using 5-10% methanol in methylene chloride as the eluent. Fractions containing the material were combined and solvent removed to obtain the pure product (425 mg, yield 79.5%). A solution of this protected peptide (400 mg, 0.27 mmol) was added 20% piperidine in acetonitrile (20 mL) and the mixture was stirred for 1 h at room temperature. The solvents were removed and the residue was triturated with hexane (3×50 mL) and dried. This was purified by column chromatography over silica gel (15 g) using 5-10% methanol in methylene chloride as the eluent. Fractions containing the material were combined and solvent removed to obtain the pure product (310 mg, yield 91%).

HPLC: Retention Time 16.66, Column: YMC, C-18 (4.6×250 mm); Solvent: Water-Acetonitrile, both containing 0.1% TFA:, Elution condition: Initial, 20% acetonitrile, linear gradient to 100% acetonitrile in 30 min; Flow rate: 1.0 mL/min.; Detection UV 254 nm $^1$HNMR: (DMSO) δ 1.10 (d, J=5.5 Hz, 3H, CH$_3$), 1.21-2.20 (m, 18H, CH$_2$), 2.95 (bs, 2H, CH$_2$), 3.12 (bs, 2H, CH$_2$), 3.50-3.75 (m, 4H, NCH$_2$), 4.10-4.55 (m, 6H, OCH$_2$, NCH, NHCH, H$_2$NCH), 4.99 (s, 2H, benzylic CH$_2$), 5.10 (dd, 2H, benzylic CH$_2$) 7.28-7.42 (m, 15H, ArH), 7.95-8.50 (m, 6H, NH)

Mass Spectrum: 1247.4 (M+H)$^+$

Preparation of DPPE-Glutaroyl-di(aminodioxaoctanoyl)-Thr-Lys-Pro-Pro-Arg-OH (6) (SEQ ID NO: 4)

To a suspension of N-Glutaroyl-dipalmitoyl phosphatidyl ethanolamine (4) (162 mg, 0.2 mmol) in methylene chloride (1.0 mL) was added TFA (200 uL) and the clear solution thus obtained was evaporated and dried in vacuo for 30 minutes. This was then redissolved in anhydrous methylene chloride (2.0 mL) and added to a solution of di(aminodioxaocta)-Thr(OBzl)-Lys(Z)-Pro-Pro-Arg(NO$_2$)OBzl (SEQ ID NO: 2) (248 mg, 0.2 mmol) in methylene chloride (3.0 mL). HATU (77 mg, 0.2 mmol) followed by diisopropylethylamine (52 mg, 0.4 mmol) were added and the reaction mixture was stirred for 6 h at room temperature. The solvents were removed in vacuo, the residue dissolved in ethyl acetate (50 mL), washed with saturated sodium bicarbonate (3×25 mL), sodium bisulphate (2×30 mL) and finally with brine (30 mL). The organic layer was dried and the solvent removed to obtain the coupled product as a colorless glassy solid (395 mg). This was purified by column chromatography over silica gel (10 g) using 10% methanol in methylene chloride as the eluent. Fractions containing the material were combined and the solvent removed to obtain the coupled product (315 mg, yield 73%). To a solution of this product (204 mg, 0.1 mmol) in methanol (15 mL), ethyl acetate (5.0 mL) and acetic acid (2.0 mL) was added Pd(OH)$_2$ (Deguzza type, 80 mg) and the mixture was hydrogenated at 50 psi for 48 h. The catalyst was filtered off and the solvents removed to obtain the crude product as a glassy solid. This was triturated with anhydrous ether to obtain the product as a white powder. This crude product was further purified by preparative HPLC on a C-4 column using 75% acetonitrile in water as the eluent. Fractions containing compound were combined and lyophalized to obtain the product 6, as a colorless fluffy solid (66 mg, Yield, 39.5%).

HPLC: Retention Time 8.8 min, Column: YMC, C-4 (4.6×250 mm); Solvent: Water-Acetonitrile, both containing 0.1% TFA:, Elution condition: Isocratic, 80% acetonitrile/20% water, Flow rate: 1.0 mL/min.; Detection uv 220 nm $^1$HNMR: (DMSO) δ 0.86 (t, 6H, CH$_3$), 1.03 (d, J=5.5 Hz, 3H, CH$_3$), 1.24 (bs, 48H, CH$_2$), 1.25-2.20 (m, 30H, CH$_2$), 2.25 (bs, 1H, CH$_2$), 2.95 (bs, 2H, CH$_2$), 3.20-3.35 (m, 24H, CH$_2$), 3.40-3.85 (m, 4H, NCH$_2$), 3.95-4.55 (m, 15H, CH$_2$, NCH, NHCH, CHCOOH)), 5.10 (bs, 1H, CH), 7.55-8.20 (m, 5H, NH).

Mass Spectrum: 1676.2 (M+H)$^+$

Elemental Analysis:

Found C, 51.58; H, 8.22; N, 8.61%

Calcd. for $C_{80}H_{147}N_{12}O_{23}P \cdot 2CF_3COOH \cdot 3H_2O$ C, 51.52; H, 7.98; N, 8.58; O, 24.51; F, 5.82; P, 1.58%.

Example 24

Influence of the Linker on the Binding of Composition I of Example 5 (BRU 114) to HAEC in Static Culture The compositions were reconstituted and assays were performed as described for Example 7 using microbubble compositions containing 1% BRU-292 (Composition of Example 23), which has a longer linker between the phospholipid ($B_{1a}$) and the targeting moiety (A) than BRU-114 (Composition I of Example 5) and 1% BRU-114.

Results:

As indicated in the table below, bubble binding to HAEC of the 1% BRU-114 composition and the 1% BRU-292 composition were similar in the presence of 2.5 µM free TKPPR (SEQ ID NO: 2) peptide. However, as the concentration of competing peptide was increased to 50 µM, it was apparent that binding of bubbles containing BRU-292 was stronger than those formulated with BRU-114, as the former were essentially unaffected by 25 µM TKPPR (SEQ ID NO: 2) while the same treatment blocked most BRU-114-containing bubble binding. Thus, a longer spacer between the lipid portion and the targeting portion of the entire targeting molecule enhances binding.

TABLE

Bubble Binding to HAEC- Effect of spacer length in the targeting molecule on binding frequency and binding strength. Values are the average of two measurements.

| Treatment | Bubbles Bound-BRU-114 Formulation | Bubbles Bound-BRU-292 Formulation |
|---|---|---|
| 2.5 microM TKPPR (SEQ ID NO: 2) | 1237 | 888 |
| 10 microM TKPPR (SEQ ID NO: 2) | 535 | 833 |
| 25 microM TKPPR (SEQ ID NO: 2) | 75 | 718 |
| 50 microM TKPPR (SEQ ID NO: 2) | 9 | 462 |

Example 25

Preparation of Air-Filled Microballoon Composition for Ultrasonic Echography Containing DPPE-Glu-GTKPPR (SEQ ID NO: 4)

Microballoons may be prepared as described in example 3 of the patent EP 0458745 using 80 mg DPPE-GLU-GTKPPR (SEQ ID NO: 4) and 0.8 g of a 50/50 DL lactide/glycolide copolymer (from Boehringer), 4 mL of octane and 200 mL of tetrahydrofurane (THF).

Example 26

Preparation of F-108-(OCH$_2$CONHGTKPPR)$_2$ (SEQ ID NO: 13)

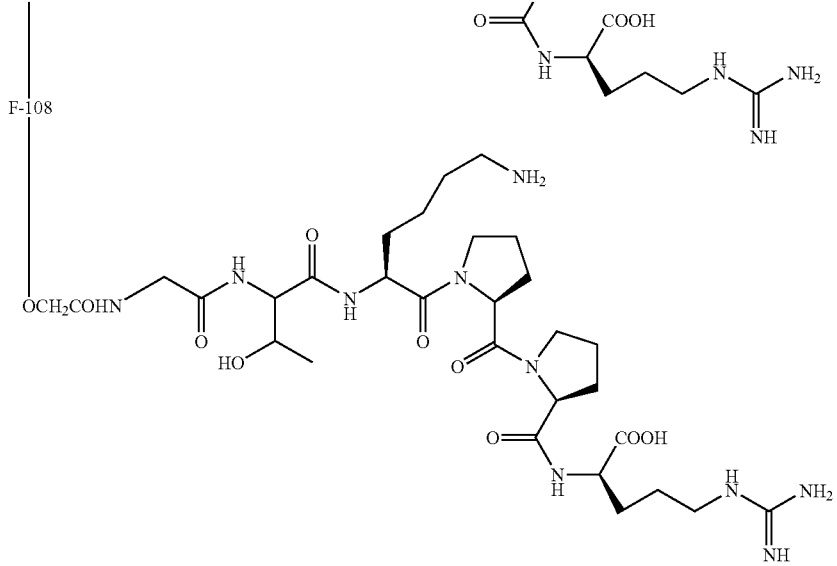

A) F-108(OCH₂COOH)₂

HOOCCH₂O-F108-OCH₂COOH

To a solution of Poloxamer F-108(OH)₂ (commercially available copolymer) 14.0 g (1.0 mmol) in THF (250 ml) was added NaH 0.1 g (4.2 mmol) and the mixture was stirred at RT for 4 h. Tertiarybutylbromoacetate 1.2 g (6.0 mmol) was added and the mixture was stirred at 45° C. for 24 h. Excess NaH was destroyed by the addition of t-butanol. THF was removed and the product was crystallized from isopropanol. Trifluoroacetic acid (25 mL) was added to 10.2 g (0.72 mmol) of the t-butylester and the mixture stirred at RT for 24 h. Ether was added and the precipitate obtained was recrystallized form ethyl alcohol. The dicarboxylic acid (50 mg) was dissolved in 2 mL of water and titrated against 0.1N tetramethylammoniun hydroxide using methylorange as an indicator. The results indicated that the substitution was (74%).

¹H-NMR, and HRMS spectra are consistent with the structure.

B) F-108(OCH₂COCl)₂

ClOCCH₂O-F108-OCH₂COCl

To a solution of F-108(OCH₂COOH)₂ (0.28 g, 0.02 mmol) in CCl₄ (7.0 mL) was added thionyl chloride (0.3 mL, 4.0 mmol) and the mixture was refluxed for 2 h. The solvents were removed on a rotary evaporator and the residue was treated with dry ether (50.0 mL) The precipitated solid was filtered, washed with ether, dried under vacuum and used in the next step without further purification.

Yield: 0.22 g (78%). ¹H-NMR, and HRMS spectra are consistent with the structure.

C) H₂N-Pro-Pro-Arg(Pmc)-OtBu

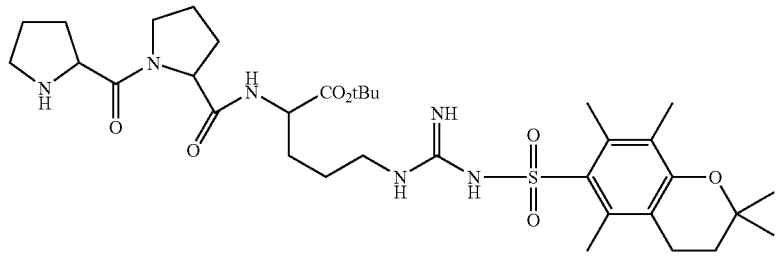

To a solution of the Fmoc-Pro-Pro (commercially available) 1.0 g (0.0023 mol) in methylene chloride was added HATU 0.95 g (0.0025 mol) and the mixture was cooled to 0° C. Diisopropylethyamine 0.43 g (0.6 mL, 0.0033 mol) was added and the mixture was stirred at 0° C. for 5 min. Arginine (Pmc) t-butyl ester 1.0 g (0.002 mol) was added and the mixture was stirred at 0° C. for 30 min and at RT for 5 h. Methylene chloride was then removed and the residue was treated with sodium bicarbonate solution and extracted with ethyl acetate. The ethyl acetate layer was washed with water and dried (Na₂SO₄). The ethyl acetate solution was evaporated and the oil obtained was dried under vacuum to give a foamy solid.

Fmoc-Pro-Pro-Arg(Pmc)-OtBu 1.7 g (1.86 mmol) was dissolved in acetonitrile (50 mL) and treated with piperidine (2 mL) and the mixture was stirred at RT for 4 h. The solvents were removed and the residue was purified by chromatography using methylene chloride-methanol (8:2).

¹H-NMR, and HRMS spectra are consistent with the structure.

D) H₂N-K (Mtt)-Pro-Pro-Arg (Pmc)-OtBu

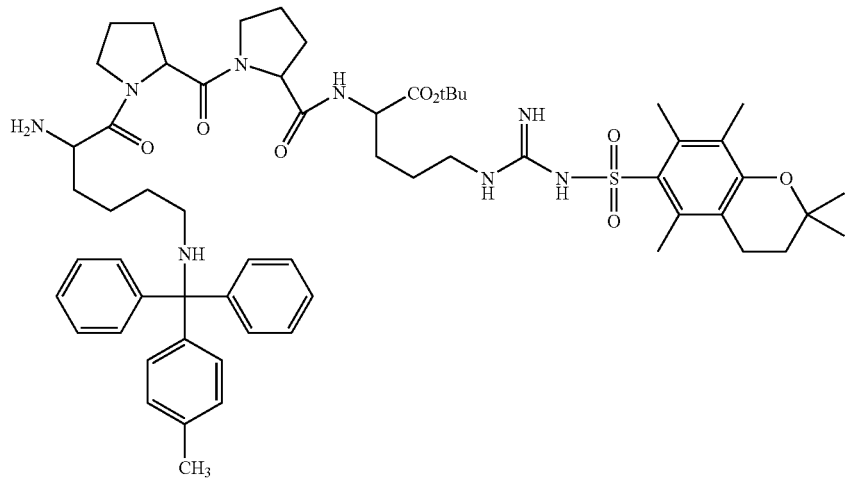

To a solution of N<sup>α</sup>-Fmoc-N<sup>ε</sup>-(4-methyltrityl)-L-lysine (commercially available) 2.12 g (0.0056 mol) and HATU 3.5 g (0.0056 mol) in methylene chloride (25 mL) was added diisopropylethylamine 0.9 g (1.2 mL, 0.007 mol) and the mixture stirred at 0° C. for 10 min. H-Pro-Pro-Arg (Pmc) t-butyl ester 3.0 g (0.00434 mol) was then added and the mixture was stirred at RT for 6 h. Methylene chloride was removed and the residue was treated with a saturated solution of sodium bicarbonate. This was then extracted with ethyl acetate, washed with water and dried (Na₂SO₄). The ethyl acetate solution was evaporated and the residue was dried under vacuum to give a foamy solid. The crude product obtained was purified by silica gel column chromatography using methylene chloride-methanol (95:5). The product containing fractions were collected and evaporated to give a foamy solid.

To a solution of the tetrapeptide in acetonitrile (20 mL), piperidine (5 mL) was added and stirred for 4 h. Acetonitrile and excess piperidine were removed and the residue was chromatographed over silica gel column. (CH₂Cl₂:CH₃OH, 95:5).

Yield: 2.2 g (86%).

¹H-NMR, and HRMS spectra are consistent with the structure.

E) H₂N-T (tBu)-K (Mtt)-Pro-Pro-Arg (Pmc)-OtBu (SEQ ID NO: 2)

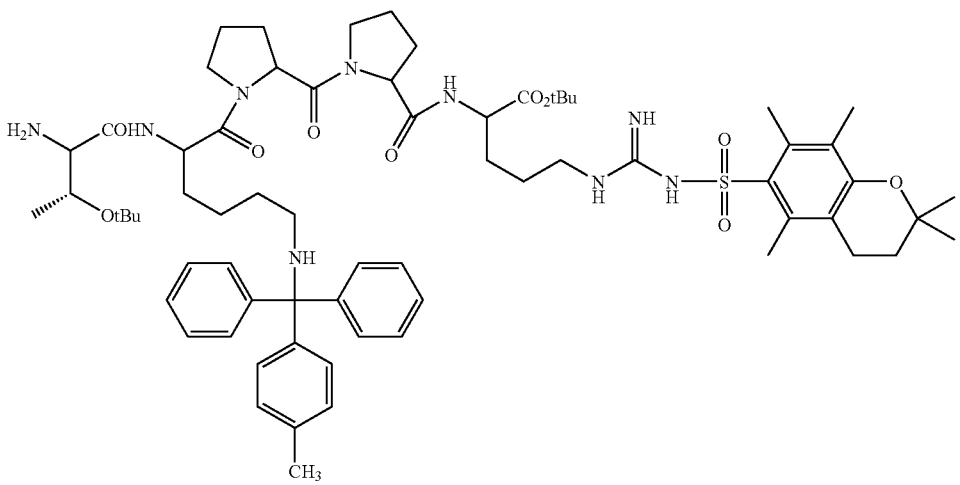

To a cooled (0° C.) solution of Fmoc-threonine t-Bu (commercially available) 1.0 g (0.00275 mol) and HATU 1.045 g (0.00275 mol) in methylene chloride was added diisopropyl ethylamine 0.39 g (0.54 mL, 0.003 mol) and the mixture was stirred at 0° C. for 5 min. The tetra peptide D) 2.2 g (0.002 mol) was then added and the mixture was stirred at 0° C. for 30 min and at RT for 12 h. Methylene chloride was then removed and the residue was treated with a saturated solution of sodium bicarbonate and extracted with ethyl acetate. The ethyl acetate layer was washed with water and dried (Na₂SO₄). The ethyl acetate was removed to give an oil, which was purified by silica gel column chromatography (CH₂Cl₂:CH₃OH 95:5). Fractions containing the compound were collected and evaporated to give an oil, which was dried, under vacuum to give a foamy solid.

Fmoc-T (tBu)-K (Mtt)-Pro-Pro-Arg (Pmc)-OtBu (SEQ ID NO: 2) was reacted with piperidine in acetonitrile and the mixture was stirred at RT for 4 h. The solvents were removed and the residue was purified by silica gel column chromatography ($CH_2Cl_2$:$CH_3OH$ 95:5). Fractions containing the product were collected and evaporated to give an oil which was dried under vacuum to give a solid.

Yield 1.6 g (90%).

$^1$H-NMR, and HRMS spectra are consistent with the structure.

F) $H_2N$-G-T (tBu)-K (Mtt)-Pro-Pro-Arg (Pmc)-OtBu (SEQ ID NO: 5)

stirred at RT for 12 h. Methylene chloride was removed and the residue was treated with a saturated solution of sodium bicarbonate and extracted with ethyl acetate. The ethyl acetate layer was washed with water and dried ($Na_2SO_4$). The ethyl acetate was removed to give an oil, which was purified by silica gel column chromatography, $CH_2Cl_2$:$CH_3OH$, 95:5). Fractions containing the compound were collected and evaporated to give an oil, which was dried under vacuum to give a foamy solid.

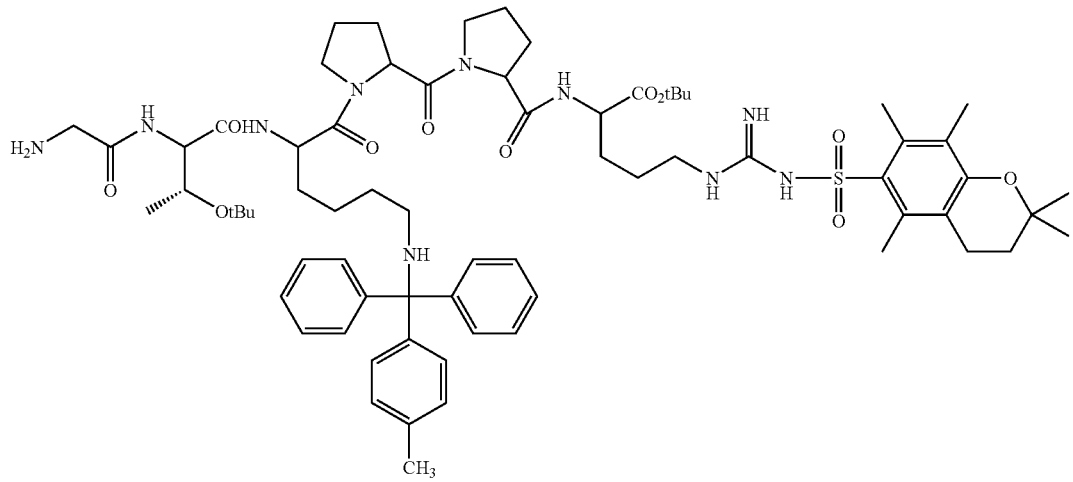

To a cooled (0° C.) solution of $H_2N$-T(tBu)-K (Mtt)-Pro-Pro-Arg(Pmc)-OtBu (SEQ ID NO: 2) 1.6 g (0.0012 mol) and HATU 0.57 g (0.0015 mol) in methylene chloride (10.0 mL) was added disopropylethylamine 0.39 g (0.54 mL, 0.003 mol) and the mixture was stirred at 0° C. for 10 min. Fmoc-glycine 0.44 g (0.0015 mol) was added to the reaction mixture and Yield: 1.65 g (84%)

$^1$H-NMR, and HRMS spectra are consistent with the structure.

G) F-108[$OCH_2CONH$-G-T(tBu)-K(Mtt)-Pro-Pro-R(Pmc)-OtBu]$_2$ (SEQ ID NO: 13)

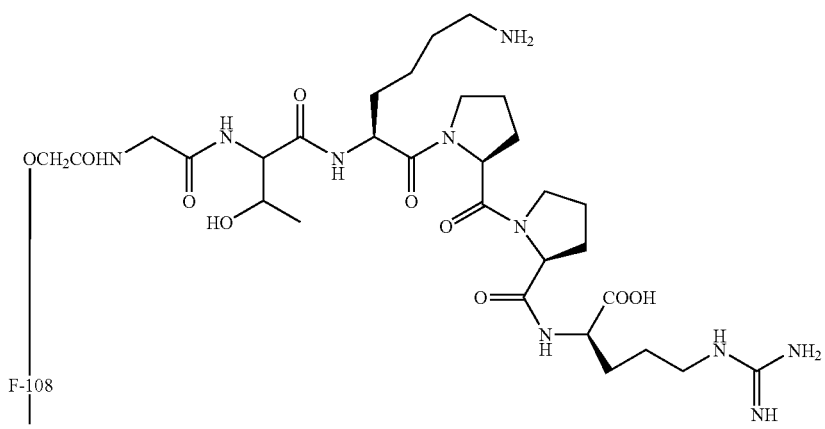

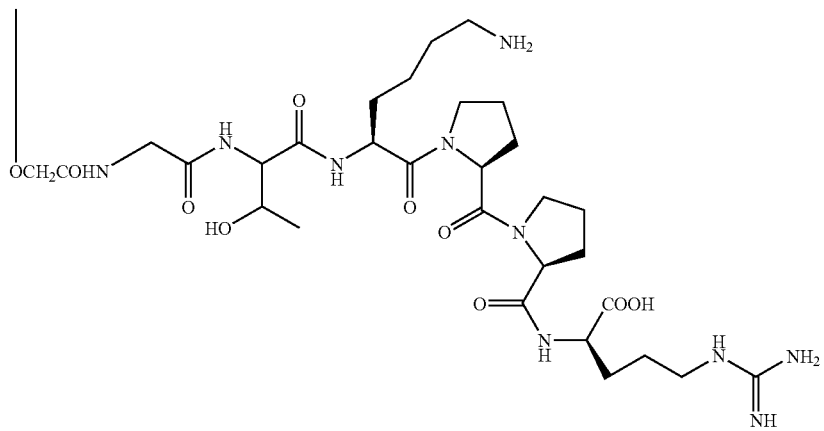

To a solution of H₂N-G-T(tBu)-K(Mtt)-Pro-Pro(R(Pmc)-OtBu (SEQ ID NO: 5) 0.14 g (0.009 mmol) in methylene chloride (2.0 mL) were added F-108(OCH₂COCl)₂B) 30 mg (0.023 mmol) and diisopropylethylamine 30 mg (40 □L, 0.23 mmol) and the mixture was stirred at RT for 24 h. Methylene chloride was removed and the residue was treated with ether. The precipitated solid was filtered and dried under vacuum. The solid obtained was dissolved in water (7.0 mL) and dialyzed in water for 24 h. The solution containing the polymer was then freeze dried to give a white solid. Yield: 0.13 g To F-108[OCH₂CONH-G-T(tBu)-K(Mtt)-Pro-Pro-R(Pmc)-OtBu]₂ (SEQ ID NO: 13) 0.12 g (0.0074 mmol) were added phenol 25.0 mg, triisopropylsilane 0.1 mL and trifluoroacetic acid (1.0 mL). The reaction mixture was stirred at RT for 12 h. TFA was removed under vacuum and the residue was dried under vacuum. The thick paste obtained was triturated with ether and the ethereal solution was decanted. The residue was dried under vacuum to give the TFA salt as a white solid. The TFA salt was dissolved in water (1.0 mL) and basified with 2 N NH₄OH (pH=10). The solution obtained was dialyzed for 24 h in water. The solution obtained was freeze dried to give F-108-(OCH₂COHNGTKPPR)₂ (SEQ ID NO: 13) as a white solid.

Yield: 92 mg (77%).

¹H-NMR, and HRMS spectra are consistent with the structure.

Example 27

Synthesis of TKPPR (SEQ ID NO: 2) Dimer (BRU-317)

Synthetic Scheme:

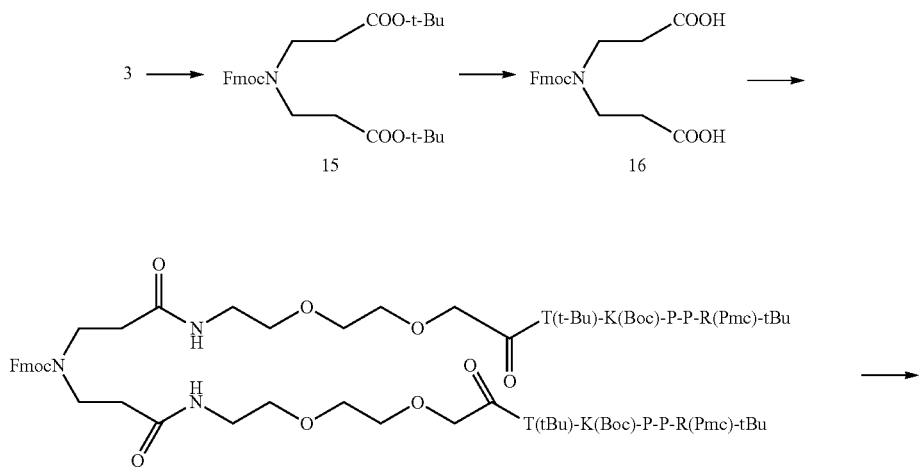

-continued

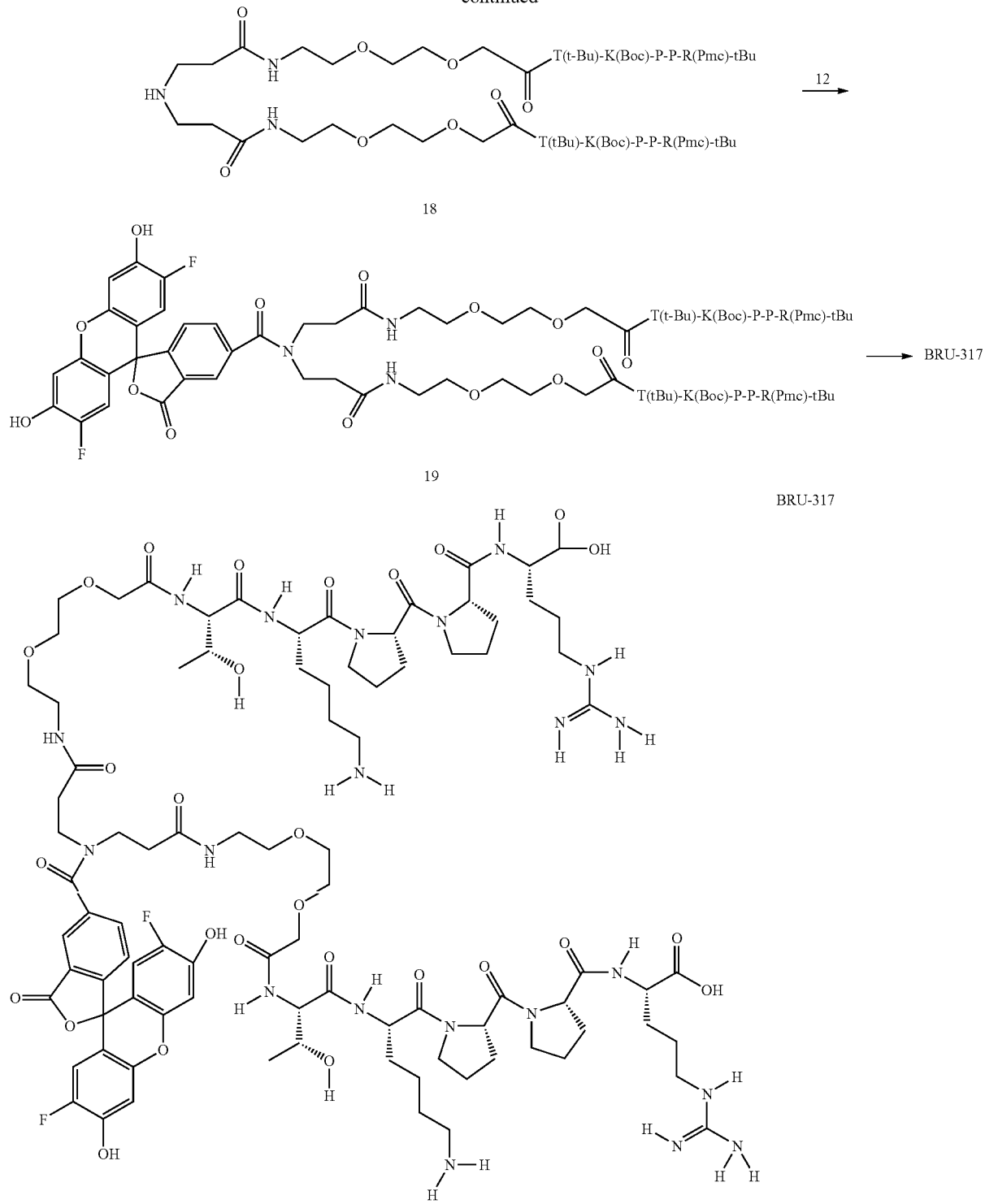

Experimental

Fmoc Amine 15:

Amine 3 (2.73 g, 10 mol) was dissolved in a mixture of THF/water (40:10) and cooled in an ice bath. Fmoc-NHS ester (5.1 g, 15 mmol) was added as a solid followed by solid sodium bicarbonate (1.34 g, 15 mmol). The reaction mixture was stirred for 20 h at RT. The solution was diluted with 100 ml of EtOAc and washed with saturated sodium bicarbonate (2×50 ml), water (1×100 ml) and dried (sodium sulfate). Evaporation of the solvent followed by chromatography of the crude product on flash silica gel (200.0 g) yielded the product as a colorless paste (6:4 hexane:EtOAc). Yield: 3.2 g (65%). $R_f$: 0.38 (1:1 EtOAc/Hexane). $^1$H NMR (CDCl$_3$) δ

(2S, 18H, Methyls), 2.25 (t, 2H, —COCH$_2$), 2.5 (t, 2H, COCH$_2$), 3.4 (t, 2H, N—CH$_2$), 3.5 (t, 2H, N—CH$_2$), 4.25 (t, 1H, Ar—CH), 4.5 (d, 2H, O—CH$_2$), 7.25 (m, 2H, Ar—H), 7.4 (m, 2H, Ar—H), 7.6 (d, 2H, Ar—H) and 7.75 (d, 2H, Ar—H). MS m/z 518.3 [M+Na].

Bisacid 16:

Fmoc amino ester 15 (3.0 g, 6 mmol) was dissolved in TFA/Anisole (22 ml 20:2, v/v) and stirred at RT for 2 h. All the volatiles were removed under reduced pressure and the residue was triturated with absolute ether (20 ml). The precipitated solid was filtered and washed with ether. The solid was then recrystallized from acetonitrile to yield a colorless solid. Yield: 1.5 g (65%). m.p.>200° C. (dec.). $^1$H NMR (DMSO-d$_6$) δ 3.0 (t, 2H, CO—CH$_2$), 3.15 (t, 2H, CO—CH$_2$), 4.1, (t, 2H, N—CH$_2$), 4.15 (t, 2H, N—CH$_2$), 5.05 (t, 1H, Ar$_2$—CH), 5.1 (2H, O—CH$_2$), 8.05 (t, 2H, Ar—H), 8.1 (t, 2H, Ar—H), 8.45 (d, 2H, Ar—H) and 8.5 (d, 2H, Ar—H). MS m/z 384.1 [M+H].

Bisamide 17:

Bisacid 16 (0.13 g, 0.34 mmol) was dissolved in THF/CH$_2$Cl$_2$ (2:1, 3 ml) and cooled in an ice bath. HATU (0.38 g, 1 mmol) was added followed by DIEA (0.26 g, 2 mmol) and stirred for 30 min at 0° C. Amine 9 (0.84 g, 0.69 mmol) inn 2 ml of CH$_2$Cl$_2$ was added and the reaction mixture was allowed to come to RT and stirred for 20 h. The solution was diluted with 50 ml of ethyl acetate and washed with saturated sodium bicarbonate (2×50 ml) and water and dried. Solvents were removed under reduced pressure and the residue was chromatographed over flash silica gel (150.0 g). Elution with 10% methanol in chloroform eluted the required product. The fractions with the compound were pooled and evaporated under reduced pressure to yield the product as a colorless foam. Yield: 0.82 g (86%). R$_f$: 0.75 (8:2 CHCl$_3$:MeOH). MS m/z 2791.4 [M+H]. HPLC: t$_R$: 25.23 min (C$_8$, RP, Zorbax column; 250×4.6 mm; Solvent A: Water with 0.1% TFA and Solvent B: ACN with 0.1% TFA; Elution rate—1 ml/min; Detection—220 nm).

Amine 18:

The Fmoc-amine 17 (0.49 g, 0/0.175 mmol) was dissolved in 10% piperidine in ACN (5 ml. V/v) and stirred for 30 min at RT. All the volatiles were removed under reduced pressure and the residue was chromatographed over flash silica gel (50.0 g). Elution with 20% methanol in chloroform eluted the required amine as a colorless foam after the evaporation of the solvents. Yield: 0.22 g 50%). R$_f$: 0.375 (3:1, Chloroform:methanol). MS m/z 2568.6 [M+H]. HPLC: t$_R$: 22.77 min (Zorbax C$_8$ RP column; 250×4.6 mm; Solvent A: Water with 0.1% TFA; Solvent B: ACN with 0.1% TFA; Elution rate: 1 ml/min; Detection—220 nm).

BRU-317:

The amine 18 (0.22 g, 0.085 mmol) was dissolved in dry DMF (0.25 ml) and treated with Oregon Green N-hydroxy succinimidyl ester (0.0433 g, 0.085 mmol) and DMAP (11 mg, 0.09 mmol) and stirred for 20 h and then warmed to 45° C. and kept at that temperature for 72 h. The reaction mixture was then diluted with water and the precipitated solid was filtered and washed with water. The bright orange solid was dried and deblocked with 6 ml of TFA and anisole (v/v—5:1) for 6 h. All the volatiles were removed under reduced pressure and the residue was diluted with 10 ml of anhydrous ether. The solid separated was filtered off and washed with ether (3×10 ml). The precipitate was then purified on a preparative HPLC column [YMC C$_{18}$ RP column; 250×30 mm; S-10Pμ; 120 Å; Elution rate—30 ml/min; Solvent A: Water with 0.1% TFA; Solvent B: ACN with 0.1% TFA; Detection 230 nm; 10-70% B in 60 min]. t$_R$: 20.32 min [YMC C$_{18}$ RP analytical column; 250×4.6 mm; Elution rate—1 ml/min; Detection at 230 nm; 10-35% B in 35 min]. $^1$H NMR in D$_2$O confirmed the expected characteristic peaks and also indicated the ratio of the one proton of the Oregon Green to the two threonine units to be 1:6 confirming the expected structure. MS m/z 1003.3 [M+2H]/2, 669.4 [M+3H]/3, 502.1 [M+4H]/4. Anal. Calcd for C$_{91}$H$_{131}$F$_2$N$_{21}$O$_{28}$, ● 5 CF$_3$COOH, ● 9 H$_2$O C, 44.3; H, 5.7; F, 11.8 and N, 10.7. Found C, 44.7; H, 5.55; F, 11.41 and N, 10.84.

Example 28

Synthesis of TKPPR (SEQ ID NO: 2) Tetramer (BRU-326)

Synthetic scheme:
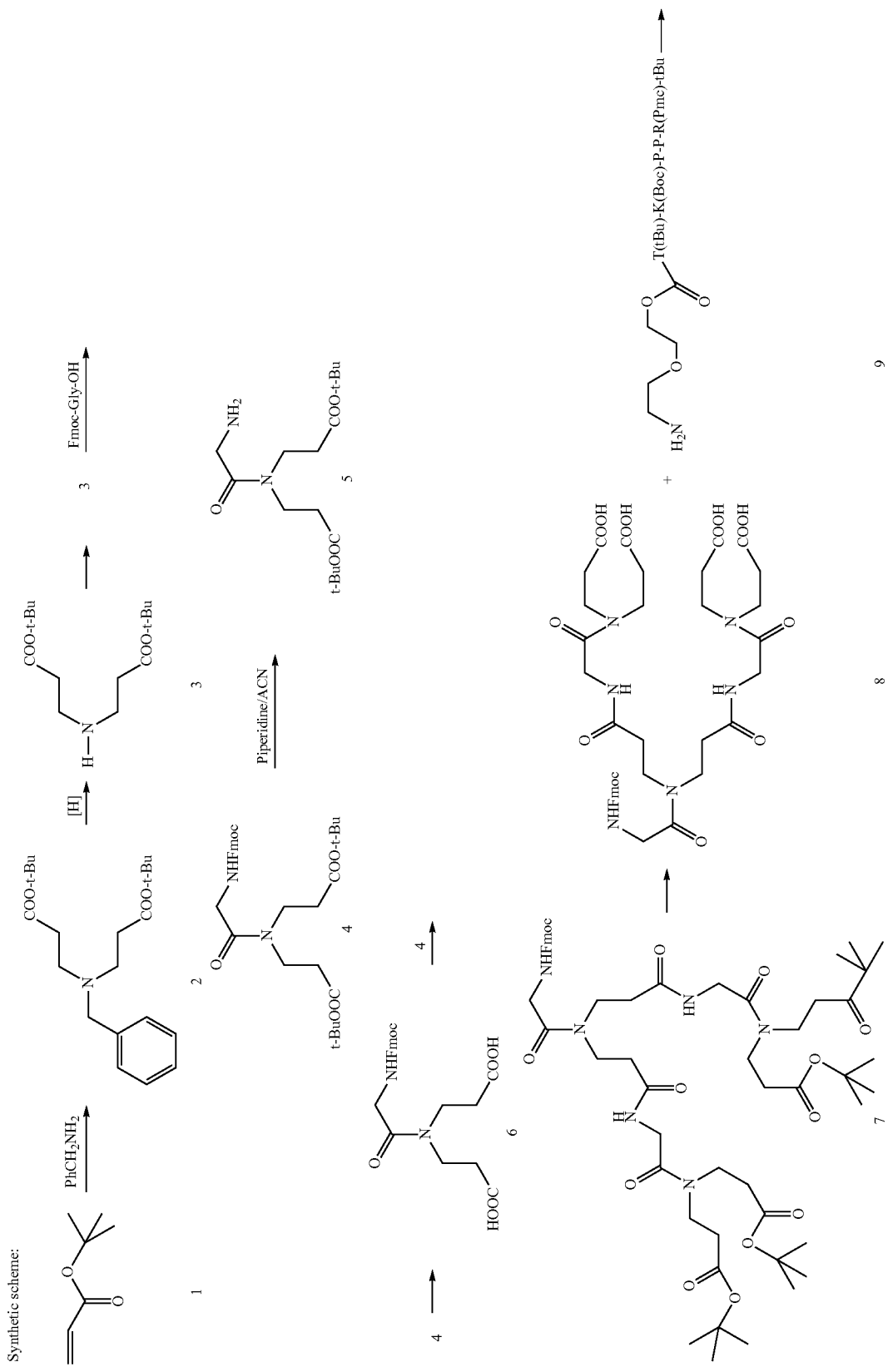

-continued
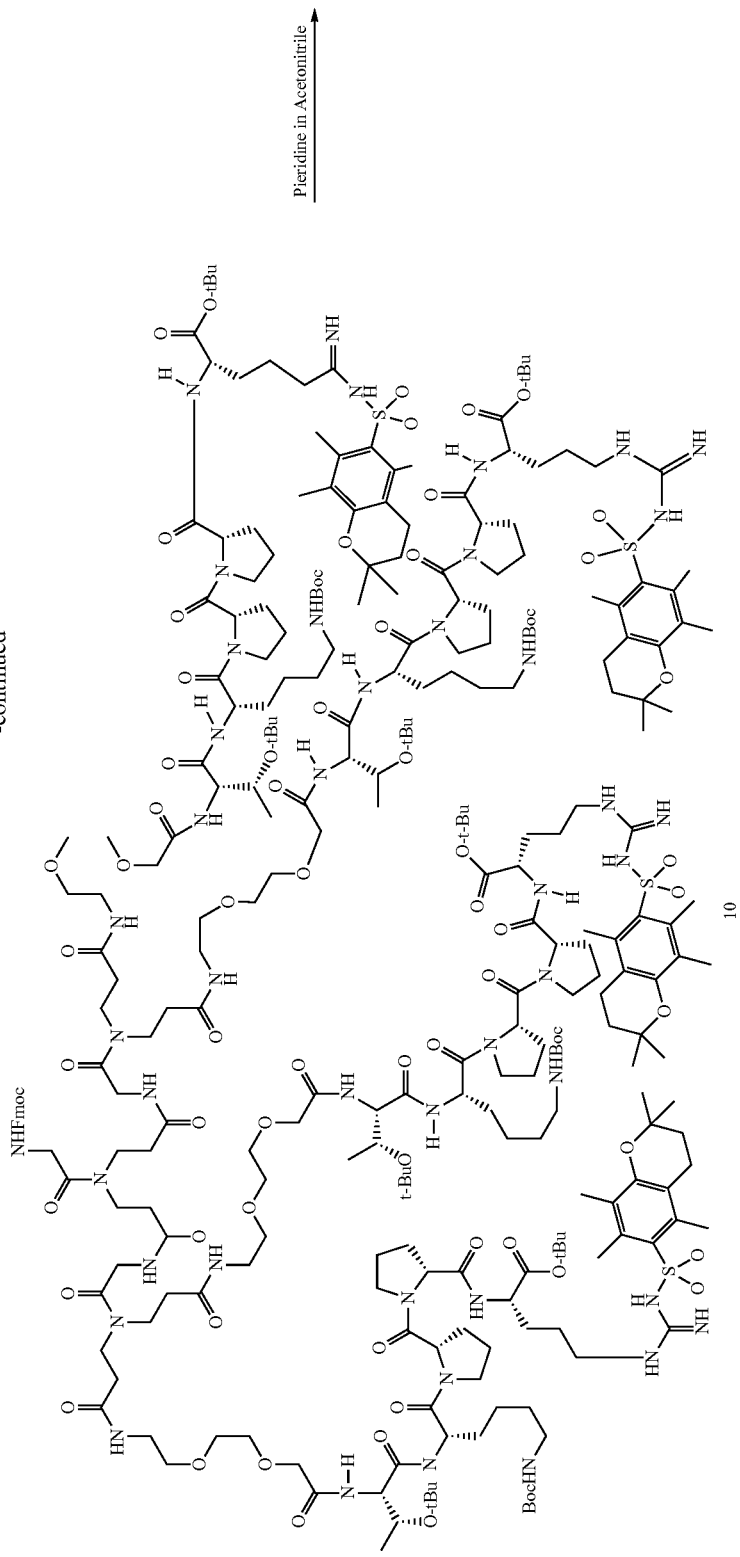

-continued
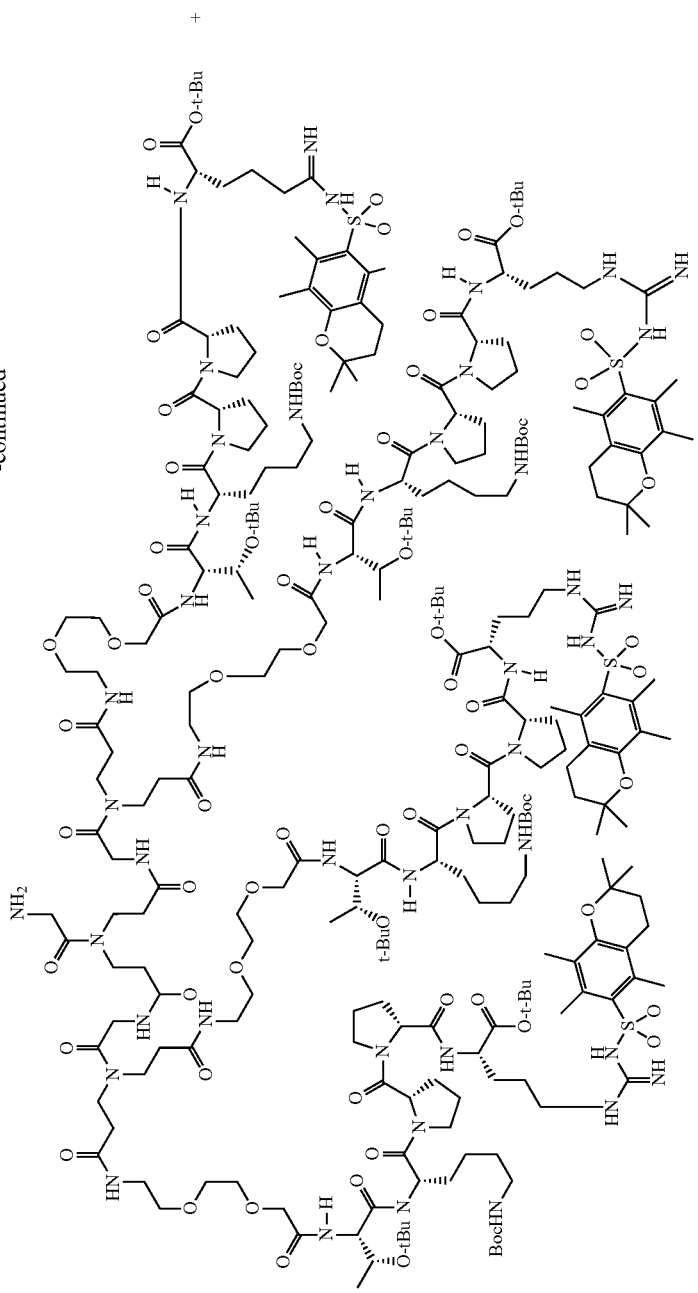

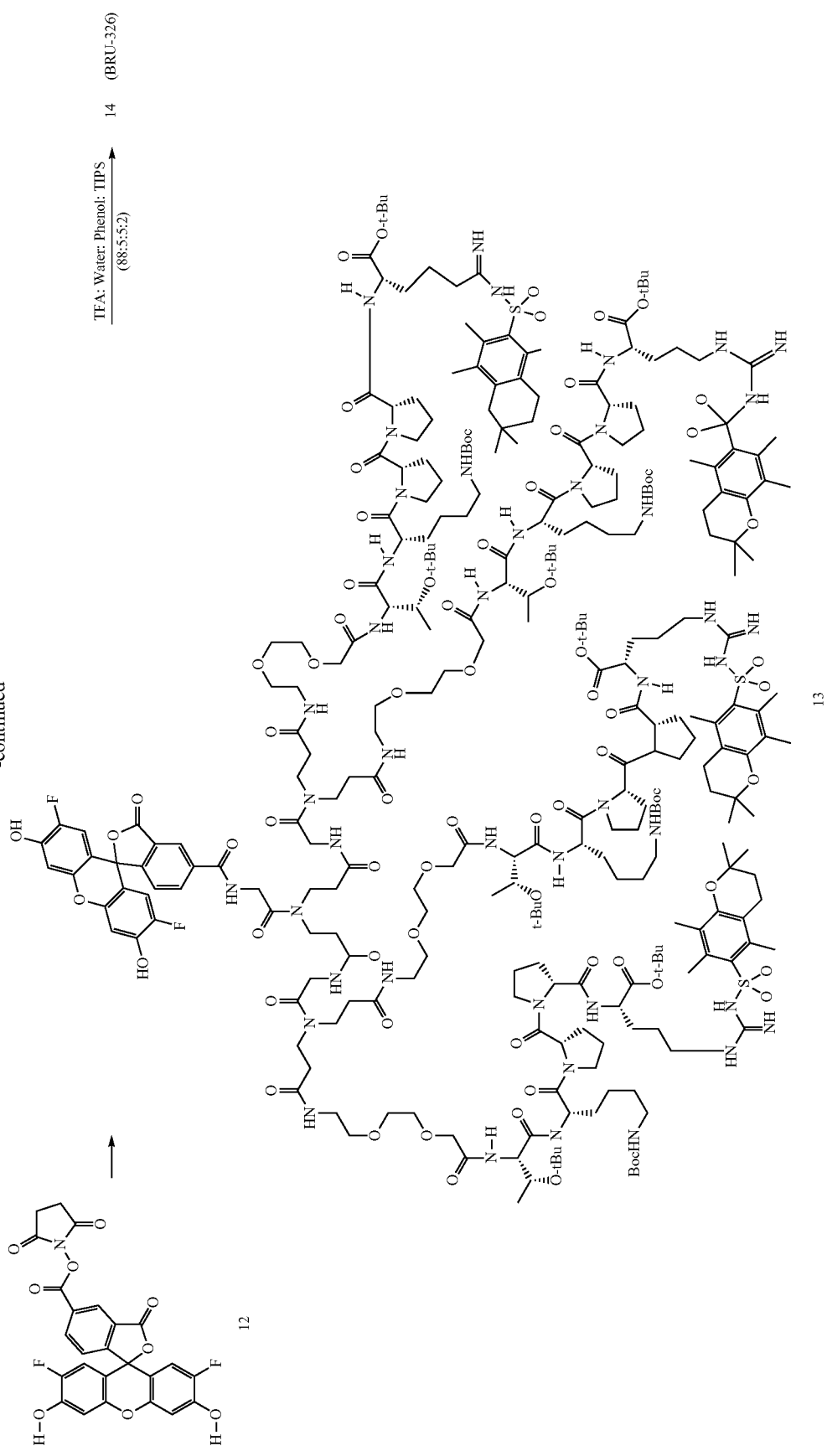

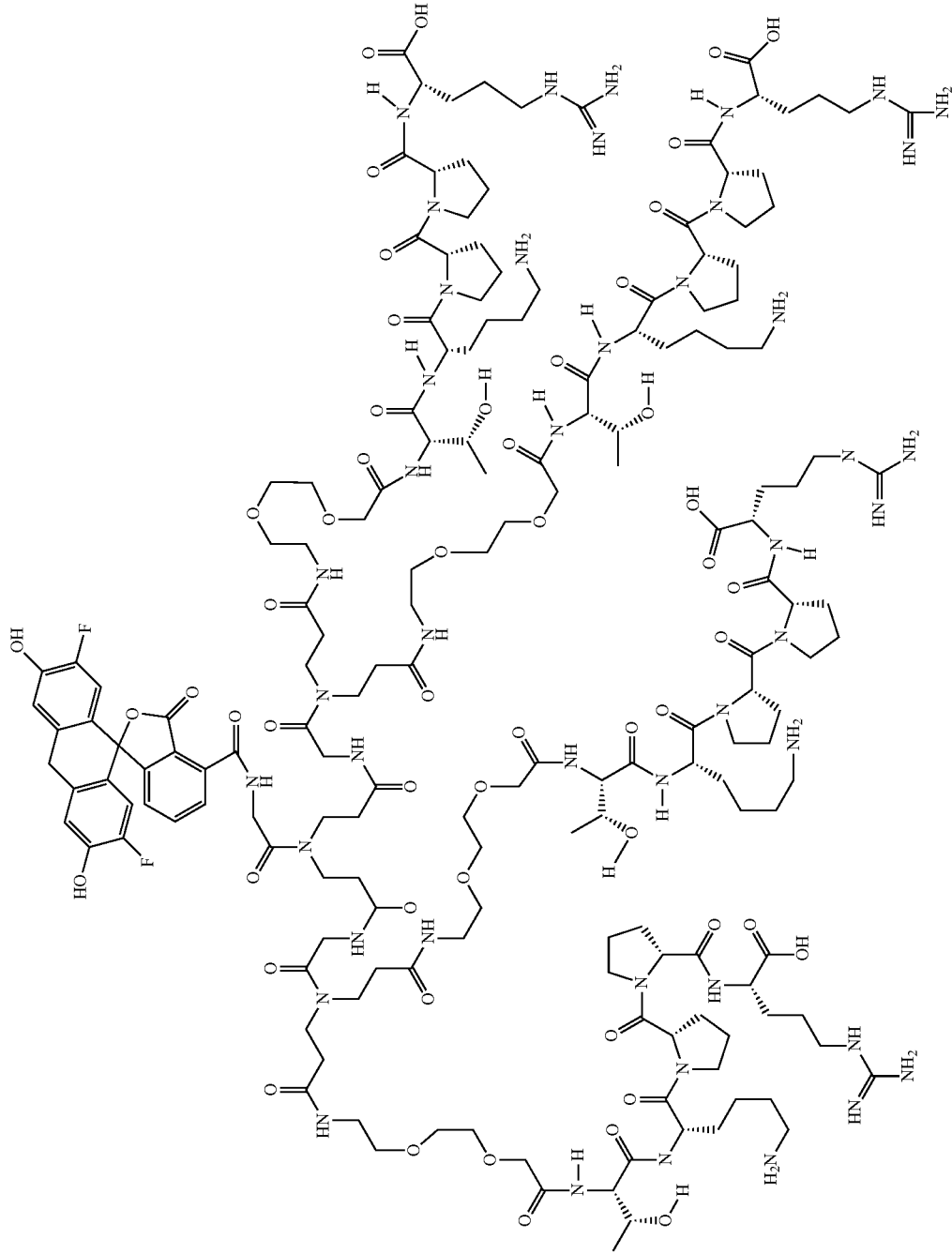

Experimental:

General:

All the amino acids were purchased from commercial sources like Advanced ChemTech, NovaBiochem and/or Neosystem. All the solvents used were of HPLC quality and were procured from VWR Scientific, Inc. NMR spectra were run on Varian Unity Inova-500 MHz instrument and the Mass Spectra were obtained from Agilent LCMSD 1100. Merck silica gel (400 mesh) was used for column chromatography. Elemental analyses were performed by Quantitative Technologies, Inc.

The abbreviations used in the discussion denote the following:

Pmc—2,2,4,6,7-Pentamethyldihydrobenzofurane-5-sulfonyl
Boc—Tertiarybutyloxycarbonyl
t-Bu—Tertiarybutyl
Fmoc—Fluorenylmethyloxycarbonyl
ACN—Acetonitrile
EtOAC—Ethyl acetate
MeOH—Methanol Preparation of Compound 2:

A mixture of benzylamine (10.7 g, 0.1 mol) and t-butyl acrylate (27.0 g, 0.21 mol) was heated under nitrogen at 80° C., till the benzylamine disappeared by TLC (3 h). The crude reaction mixture was loaded onto a silica gel column (800.0 g) and washed with 4.0 L of hexane and then eluted with 10% ethyl acetate in hexane. The fractions containing the product were pooled and evaporated to yield the desired compound as a colorless oil. $R_f$: 0.81 (1:1 Hexane/EA). Yield: 23.0 g (63%). $^1$H NMR (CDCl$_3$) δ1.45 (s, 9H, t-Bu), 2.4 (t, 4H, —COCH$_2$), 2.75 (t, 4H, —N—CH$_2$), 3.6 (s, 2H, N—CH$_2$—Ar) and 7.25 (m, 5H, Ar—H). MS m/z 364.2 [M+H]

Preparation of Compound 3:

Amine 2 (2.12 g, 5.84 mmol) in THF (25 ml) was hydrogenated in the presence of Pd(OH)$_2$ on carbon (50% by wt water and Pd content 20%; 0.4 g) until the starting amine disappeared on TLC (6 h). The reaction mixture was filtered through celite and the filtrate was concentrated under reduced pressure to yield the amine as a colorless oil. Yield: 1.52 g (95.5%). $^1$H NMR (CDCl$_3$) δ 1.5 (s, 18H, t-Bu), 2.1 (m, 1H, N—H), 2.45 (t, 3H, —COCH$_2$) and 2.8 (t, 4H, —N—CH$_2$). MS m/z 274.5 [M+H].

Compound 4:

Fmoc-Gly-OH (4.5 g, 15 mmol) in dry dichloromethane (25 ml) was treated with HATU (6.88 g, 18.0 mmol) followed by DIEA (5.16 g, 40 mmol) and stirred at 0° C. for 20 min. To this activated acid amine 3 (3.78 g, 13.85 mmol) was added in dichloromethane (25 ml) and stirred at RT for 20 h. The reaction mixture was then diluted with ethyl acetate (150 ml) and washed with saturated sodium carbonate solution (3×100 ml), water (3×100 ml) and dried (sodium sulfate). The solution was filtered and concentrated under reduced pressure to a paste. The crude paste was chromatographed on flash silica gel (500 g). The column was washed with 25% ethyl acetate in hexane (4 L) to remove any fast moving impurities and then continued elution with 6:4 ethyl acetate:hexane yielded the product as a colorless viscous oil. Yield: 7.0 g (91.5%). $^1$H NMR (CDCl$_3$) δ 1.5 (s, 18H, t-Bu methyls), 2.5 (m, 4H, —COCH$_2$), 3.6 (m, 6H, —N—CH$_2$), 4.25 (t, 1H, Ar$_2$—CH), 4.4 (d, 2H, —O—CH$_2$) and 5.8 (bs, 1H, —NH). MS m/z 563.3 [M+H].

Compound 5:

A solution of Fmoc-amine 4 (3.5 g, 6.34 mmol) in 10% piperidine in acetonitrile (v/v, 30 ml) was stirred at RT for 30 min by which time the starting material disappeared on TLC. The reaction mixture was concentrated under reduced pressure and the residue was purified on a flash silica gel column (200.0 g). Elution with 1% MeOH in chloroform removed most of the impurities and continued elution with 5% MeOH in chloroform yielded the product as a colorless solid. m.p.—57-58° C. Yield: 1.56 g (74.6%). $^1$H NMR (CDCl$_3$) ☐ 1.4 (s, 18H, methyls), 1.7 (bs, 2H, —NH$_2$), 2.5 (m, 4H, —COCH$_2$), 3.5-3.6 (m, 6H, —NCH$_2$). MS m/z 331.2 [M+H].

Compound 6:

Fmoc-amine 4 (3.5 g, 6.34 mmol) was dissolved in TFA: anisole (10:2, v/v, 24 ml) and stirred at RT for 6 h. All the volatiles were removed under reduced pressure and the residue was triturated with dry ether (50 ml). The precipitated solid was removed by filtration and washed with dry ether (3×25 ml). The above solid was recrystallized from acetonitrile to provide the diacid as a crystalline solid. Yield: 1.88 g (67%). m.p.—172-173° C. $^1$H NMR (DMSO-d$_6$) δ 2.4 (m, 4H, —CH$_2$—COOH), 3.3 (m, 6H, —N—CH$_2$), 3.75 (t, 1H, Ar$_2$—CH), 4.1 (t, 2H, —O—CH$_2$), 7.15 (t, 2H, Ar—H), 7.2 (t, 2H, Ar—H), 7.55 (d, 2H, Ar—H) and 7.75 (d, 2H, Ar—H). MS m/z 441.1 [M+H].

Compound 7:

A solution of the Fmoc-amino acid 6 (0.314 g, 0.71 mmol) in dry dichloromethane and THF (10 ml, 7:3 v/v) was cooled in an ice-bath and treated with HATU (0.65 g, 1.71 mmol) followed by DIEA (0.26 g, 2 mmol) and stirred at 0° C. for 30 min under nitrogen. Amine 5 (0.495 g, 1.5 mmol) in dry dichloromethane (5 ml) was added to the above activated acid followed by DIEA (0.26 g, 2 mmol) and the reaction mixture was stirred at RT for 20 h. The reaction mixture was diluted with 200 ml of EtOAc and the organic layer was washed with saturated sodium carbonate (2×100 ml), water (2×100 ml) and dried (sodium sulfate). The solution was filtered and evaporated under reduced pressure to yield the crude product as a brown paste. The paste was loaded onto a flash silica gel column and chromatographed (125.0 g). The column was initially washed with 700 ml of chloroform followed by 2% methanol in chloroform until all the products were eluted out of the column. The fractions with the compound were pooled and evaporated under reduced pressure to furnish the tetra ester 7 as a colorless paste. Yield: 0.67 g (88.7%). $^1$H NMR (CDCl$_3$) δ 1.4 (s, 36H, methyls), 2.5 (m, 12H, —CO—CH$_2$), 3.5-3.7 (m, —N—CH$_2$), 4.2-4.4 (3m, 6H, —CO—CH$_2$—N—), 5.75 (bm, 1H, NH-Fmoc) and 7.25-7.75 (m, 8H, Ar—H). MS m/z 1065.4 [M+H].

Tetra Acid 8:

The tetra ester 7 (0.67 g, 0.63 mmol) was dissolved in TFA/anisole (12 ml, 10:2 v/v) and stirred at RT for 20 h. All the volatiles were removed under reduced pressure and the residue was triturated with dry ether (50 ml). The solid separated was washed with ether (3×25 ml) and then recrystallized from acetonitrile. Yield: 0.24 g (45%). m.p. 135-136° C. HPLC: $t_R$—27.22 min [YMC—RP C$_{18}$ column; 25×0.46 cm; elution rate—1 ml/min; Solvent A—Water (0.1% TFA) and solvent B—ACN (0.1% TFA); 50-100% B in 50 min]. $^1$H NMR (DMSO-d$_6$) δ 2.6 (m, 12H, —CO—CH$_2$), 3.6 (m, 12H, —N—CH$_2$), 4.1 (m, 6H, —CO—CH$_2$—N), 4.4 (m, —OCH$_2$ and Ar$_2$—CH) and 7.4-8.0 (m, 8H, Ar—H). MS m/z 841.2 [M+H].

Amine 9:

a) Fmoc-Pro-Pro-Arg(Pmc)-t-Bu:

A solution of commercially available Fmoc-Pro-Pro-OH (1.96 g, 4.44 mmol) was dissolved in dry dichloromethane (25 ml) and cooled in an ice bath. HATU (2.1 g, 5.4 mmol) was added followed by DIEA (0.774 g, 6 mmol). The reaction mixture was stirred for 10 min and then to the above activated acid, H-Arg(Pmc)-t-Bu (2.2 g, 4.44 mmol) was added as a solid followed by DIEA (0.774 g, 6 mmol). The solution was allowed to come to RT and stirred for 20 h at RT. The mixture was poured into saturated sodium bicarbonate solution (100 ml) and stirred for 5 min. The organic layer was separated and washed with water (2×100 ml) and dried (sodium sulfate). Evaporation of the solvent yielded the product as a colorless foam. Yield: 4.15 g (100%). MS m/z 913.4 [M+H].

b) H-Pro-Pro-Arg(Pmc)-t-Bu):

A solution of the Fmoc-Pro-Pro-Arg(Pmc)-t-Bu (4.15 g, 4.4 mmol) in 10% piperidine in acetonitrile (v/v, 50 ml) was stirred at RT for 30 min. All the volatiles were removed under reduced pressure and the residue was chromatographed on flash silica gel (360.0 g). All the fast moving impurities were removed by washing the column with 10% methanol in chloroform. Continued elution with 20% methanol in chloroform containing 0.1% TEA eluted the required amine. The fractions containing the amine were pooled and evaporated to furnish the amine as a colorless foam. $R_f$: 0.125 (20% methanol in chloroform). Yield: 3.0 g (98%). MS m/z 691.4 [M+H].

c) Fmoc-Lys(Boc)-Pro-Pro-Arg(Pmc)-t-Bu: (SEQ ID NO: 12)

Fmoc-Lys(Boc)-OH (2.11 g, 4.5 mmol) in dry $CH_2Cl_2$ (25 ml) was cooled in an ice bath and treated with HATU (1.9 g, 5 mmol) and DIEA (0.71 g, 5.5 mmol) and stirred for 10 min. H-Pro-Pro-Arg(Pmc)-t-Bu (3.0 g, 4.34 mmol) was added followed by DIEA (0.71 g, 5.5 mmol) to the activated acid and stirred at RT for 20 h. The reaction mixture was diluted with 200 ml of ethyl acetate and washed with saturated sodium carbonate (2×200 ml) followed by water (2×200 ml) and dried (sodium sulfate). Evaporation of the solvents under reduced pressure furnished an off white foam which was taken to the next step without further purification. Yield: 5.1 g (100%). MS m/z 1141.8 [M+H].

d) H-Lys(Boc)-Pro-Pro-Arg(Pmc)-t-Bu (SEQ ID NO: 12):

Fmoc-Lys(Boc)-Pro-Pro-Arg(Pmc)-t-Bu (5.1 g, 4.34 mmol) was dissolved in 10% piperidine in acetonitrile (50 ml, v/v) and stirred for 30 min at RT. All the volatiles were removed under reduced pressure to yield a paste and the paste was loaded onto a flash silica gel column (250.0 g) and chromatographed. Elution with 9:1 chloroform:methanol yielded the product as a colorless foam. Yield: 3.55 g (89%). $R_f$: 0.2 (MeOH:CHCl3—1:9). MS m/z 920.0 [M+H]

e) Fmoc-Thr(t-Bu)-Lys(Boc)-Pro-Pro-Arg(Pmc)-t-Bu (SEQ ID NO: 2):

H-Lys(Boc)-Pro-Pro-Arg(Pmc)-t-Bu (3.55 g, 3.86 m mmol) was added to a solution of the activated acid prepared from Fmoc-Thr(t-Bu)-OH (1.6 g, 4 mmol) and HATU (1.9 g, 5 mmol) and DIEA (1.29 g, 10 mmol) in dry $CH_2Cl_2$ (25 ml) and stirred for 20 h at RT.

The reaction mixture was then diluted with ethyl acetate (200 ml) and washed with saturated sodium carbonate (2×200 ml), water (2×200 ml) and dried (sodium sulfate). The solution was filtered and the solvents were removed under reduced pressure to leave behind a paste. The paste was chromatographed over flash silica gel (400 g). Elution with 2% methanol in chloroform furnished the product as a colorless foam. Yield: 3.5 g (70%).

m.p. 135-138° C. MS m/z 1298.2 [M+H].

f) H-Thr(t-Bu)-Lys(Boc)-Pro-Pro-Arg(Pmc)-t-Bu (SEQ ID NO: 2):

Fully protected TKPPR (0.4 g, 0.3 mmol) was dissolved in 10% piperidine in ACN (10 ml, v/v) for 30 min at RT. All the volatiles were removed under reduced pressure and the residue was chromatographed over flash silica gel (50.0 g). Elution with 10% methanol in chloroform eluted the amine as a colorless foam. Yield: 0.11 g (34%). MS m/z 1076.7 [M+H].

g) Fmoc-HN—$CH_2$—$CH_2$—O—$CH_2$—$CH_2$—O—$CH_2$—CO-Thr(t-Bu)-Lys(Boc)-Arg(Pmc)-t-Bu:

Commercially available Fmoc-8-amino-3,6-dioxaoctanoic acid (0.55 g, 0.425 mmol) was activated with HATU (0.19 g, 0.5 mmol) and DIEA (0.065 g, 0.5 mmol) in 2 ml of dry dichloromethane at 0° C. for 10 min and then H-Thr(t-Bu)-Lys(Boc)-Pro-Pro-Arg(Pmc)-t-Bu (SEQ ID NO: 2) (0.4 g, 0.37 mmol) in dry dichloromethane (2 ml) was added and stirred at RT for 20 h. Solvent was evaporated under reduced pressure and the residue was chromatographed over flash silica gel (50.0 g). Elution with 5% methanol in chloroform eluted the product as an off white foam. Yield: 0.346 g (65%). $R_f$: 0.75 (MeOH:CHCl$_3$—1:9). MS m/z 1443.6 [M+H].

Amine 9:

The above protected amine (0.34 g, 0.24 mmol) was dissolved in 10% piperidine in ACN (5 ml, v/v) and stirred for 30 min at RT. All the volatiles were removed under reduced pressure and the residue was triturated with dry ether (10 ml). The solid was filtered and washed with dry ether (3×10 ml). The solid was again dissolved in 20 ml of ethyl acetate and washed with water (2×20 ml) and dried (sodium sulfate). The above product was chromatographed over 25.0 g of flash silica gel and elution with 25% methanol in chloroform eluted the product as a colorless foam. Yield: 0.226 g (56%). Rf: 0.38 (85:15 CHCl3:MeOH). MS m/z 1221.5 [M+H].

Tetra Amide 10:

A solution of the tetra acid 8 (0.189 g, 0.225 mmol) was dissolved in anhydrous THF (2 ml) and cooled to 0° C. HATU (0.51 g, 1.35 mmol) was added followed by 2 ml of anhydrous dichloromethane. DIEA (0.194 g, 1.5 mmol) was added and the solution was stirred for 30 min at 0° C. Amine 9 (1.11 g, 0.91 mmol) and DIEA (0.194 g, 1.5 mmol) in 2 ml of dichloromethane were added and the reaction mixture was allowed to come to RT and stirred for 20 h. The mixture was then quenched with 10 ml of saturated sodium bicarbonate solution and then diluted with 30 ml of EtOAc. The organic layer was separated, washed with water (2×50 ml), saturated sodium bicarbonate (2×50 ml) and dried (sodium sulfate). Evaporation of the solvents furnished a brown gum and the gummy product was loaded onto a flash silica gel column (200.0 g) and chromatographed. The column was eluted with 2000 ml each of 5%, 10% and 15% methanol in chloroform. Finally the product was eluted with 20% methanol in chloroform. The fractions containing the product were pooled and evaporated to give the teraamide as an off white foam. Yield: 0.61 g (48%). $R_f$: 0.56 (7:3 CHCl$_3$-MeOH). MS m/z 2827.2 [M+H/2], 1885.7 [M+3H/3], 1414.7, [M+4H/4], 1111.9 [M+5H/5].

Amine 11:

The fully protected amine 10 (0.198 g, 0.035 mmol) was dissolved in 10% piperidine in ACN (5 ml) and stirred for 30 min at RT. All the volatiles were removed under reduced pressure and the residue was dissolved in 50 ml of dichloromethane and washed with water (5×50 ml) and dried (sodium sulfate). The solvent was evaporated to about 5 ml and then diluted with 20 ml of anhydrous ether and cooled in ace. The solid separated was filtered and washed with anhydrous ether. The solid was then dried under high vacuum for 2 h at RT to yield the amine as a colorless foam. Yield: 0.15 g (76%). No further purification was done and this was immediately used in the next step. NMR showed the disappearance of the signals representative of the Fmoc group. MS m/z 2717.4 [M+2H]/2, 1811.6 [M+3H]/3, 1359.0 [M+4H]/4, 1087.2 [M+5H]/5.

BRU-326:

Amine 11 (0.15 g, 0.0267 mmol) was dissolved in anhydrous DMF (0.2 ml) and was treated with commercially available Oregon Green N-hydroxy succinimidyl ester (0.034 g, 0.067 mmol) and DMAP (0.008 g, 0.067 mmol) and stirred at RT for 50 h. At the end of the period, the solvent was removed under high vacuum at RT and then treated with 5 ml of ice cold water and triturated. The precipitated solid was filtered and thoroughly washed with water. The solid was again dissolved in DMF and co-evaporated several times to remove any water present. The above crude amide with the label was dissolved in TFA:Anisole:Water (10 ml. 95:5:1. V/v/v) and stirred at RT for 6 h. All the volatiles were removed under vacuum and the residue was triturated with anhydrous ether (10 ml). The bright yellow solid was filtered and washed with ether (3×10 ml) and dried under vacuum in the absence of light. The solid was then purified on a preparative HPLC. Conditions: Column—YMC—RP, $C_{18}$; 250 mm×30 mm; S-10Pµ; 120 Å; elution rate—25 ml/min; solvent A—water with 0.1% TFA and solvent B—acetonitrile with 0.1% TFA; 20-100% B in 240 min. The fractions containing the major peak were collected, pooled and freeze dried. Yield: 47.5 mg (45%). 1H NMR in $D_2O$ was indicative of all, the expected characteristic peaks of the amino acids and Oregon Green. The integral ratio of the one proton of the Oregon Green to the four threonine units in the molecule turned out to be exactly 1:12 as expected. Analysis further confirmed the expected product. $t_R$: 18.19 min (YMC RP $C_{18}$ column; 250×4.6 mm; S-10Pµ; 120 Å; 10-40% B in 30 min; elution rate: 1 ml/min; wavelength monitored—230 nm. Anal. Calcd for $C_{173}H_{270}F_2N_{46}O_{55}$, ● 12 $CF_3COOH$, ● $9H_2O$, C, 43.47; H, 5.56; F, 13.26 and N, 11.84. Found: C, 43.17; H, 5.40, F, 12.86, N, 11.78. MS m/z 783.3 {M+5H]/5, 652.9 [M+6H]/6, 559.7 {M+7H]/7 and 490.0 {M+8H]/8.

Experimental:

Example 29

Synthesis of TKPPR (SEQ ID NO: 2) Dimer and Tetramer (BRU-337 and BRU-346) on a Lysine Core with Trioxa Oregon Gren at C-terminal A solid phase approach (using safety catch resin) to synthesize a small inert core molecule of radially branching lysine dendrites onto which a number of (bioactive) TKPPR (SEQ ID NO: 2) peptides with markers were anchored. The inert lysine core, which is attached to a solid phase support, allows the synthesis of desired peptides (di- or tetra or octavalent) directly on the branched lysine core. The final multivalent ligand thus carries markers at tips of peptide tethers that radiate from a central lysine core.

The synthesis of BRU-337, the dimeric-TKPPR (SEQ ID NO: 2) (15) and BRU-346, the tetrameric-TKPPR (SEQ ID NO: 2) (16) with Oregon Green as a marker at the C-terminal was initiated from the Fmoc-Gly-sulfamylbenzoyl-MBHA (1) resin following the Fmoc-solid phase peptide coupling protocol using HATU as coupling agent and is shown in the synthesis flow chart [the number in the flow chart indicates the number of the compound (peptide) shown in the line]. As a first step, the commercially available 4-sulfamylbenzoyl MBHA resin was reacted with Fmoc-Gly-OH in the presence of PyBop-DIEA at −20° C. in DMF to provide the starting material, Fmoc-Gly-Sulfamyl-Benzoyl-MBHA (1) resin. After removal of the Fmoc group of the Fmoc-Gly-Sulfamyl-Benzoyl-MBHA (1) resin, the loading of the peptide sequence TKPPR (SEQ ID NO: 2) was carried out after attaching Fmoc-Lys(Fmoc)-OH to the Gly-Sulfamyl-Benzoyl-MBHA resin. The standard Fmoc protocol was employed in the loading procedure using 6 equivalents of each amino acid and coupling reagent HATU for each amine coupling (for dimeric construct, 6 equivalents). The last amino acid threonine (Thr) was loaded as boc derivative to avoid the removal of the Fmoc either when the peptide on the resin or after displacement of the peptide form the resin by the nucleophile. After completion of the loading process, the sulfamyl amide nitrogen was activated by reacting with iodoacetonitrile (1-ACN) (20 equiv.) in the presence of DIEA (5 equiv.) in NMP. After subjecting to the nucleophilic displacement reaction with TTDA-OG (14) (see Scheme 1), the isolated protected peptide was then treated with the reagent 'B' (TFA:Water:Phenol:Triiso-propylsilane; 88:5:5:2) to remove protecting groups. The crude peptide was then purified on a semi-preparative (C18) column to isolate the pure dimeric peptide. Analytical data such as MS, $^1$H NMR and HPLC confirmed the structure and homogeneity of the isolated product. Synthetic steps involved in the preparation of dimeric TKPPR (SEQ ID NO: 2), 15 with a reporter moiety, Oregon Green, are shown in the following synthesis flow chart and the scheme 1.

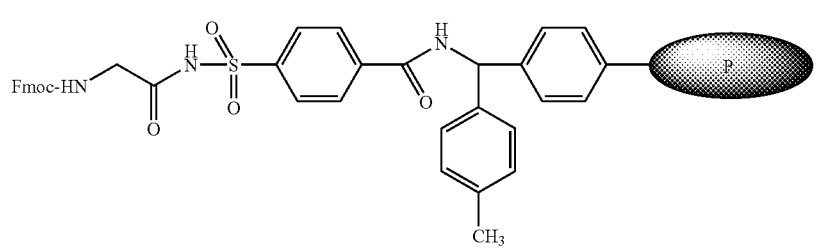

1

Figure 7:
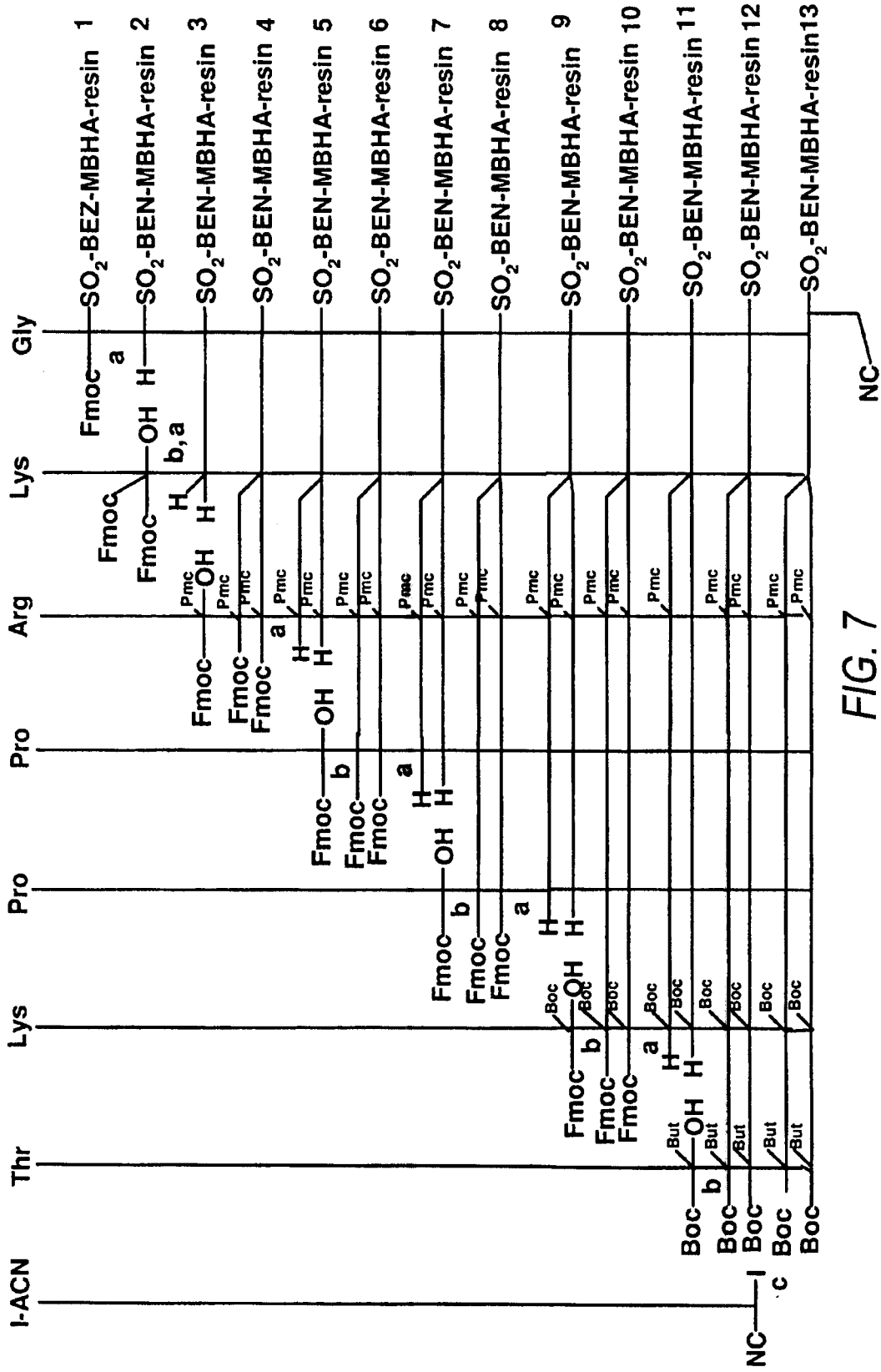
FIG. 7 depicts synthesis flow chart.

Synthesis Flow Chart is Summarized in FIG. 7.
Loading of TKPPR (SEQ ID NO: 2) on Fmoc-Gly-4-Sul-famylBenzoyl-MBHA Resin to prepare a Dimeric Construct Scheme 1
Nucleophilic Displacement and Deprotection reactions

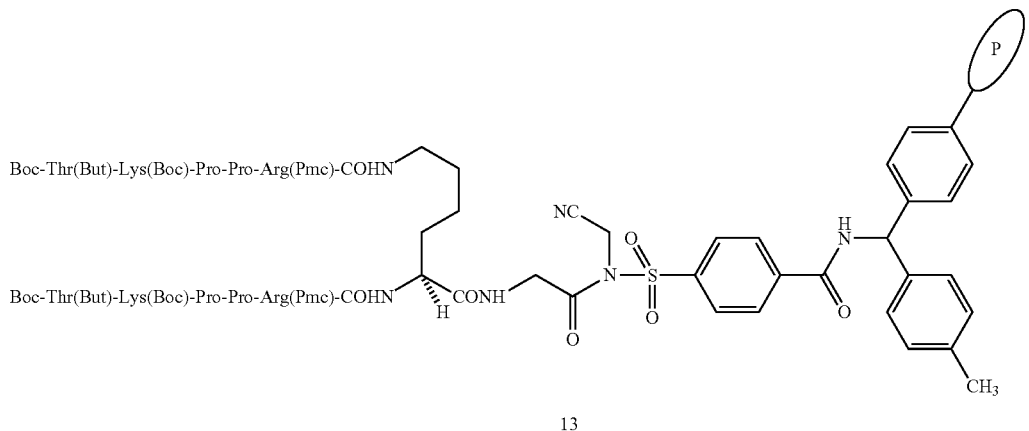

13 i) Nucleophilic Displacement reaction with TTDA-Oregon Green ii) Deprotection with 'reagent B' and purification by HPLC

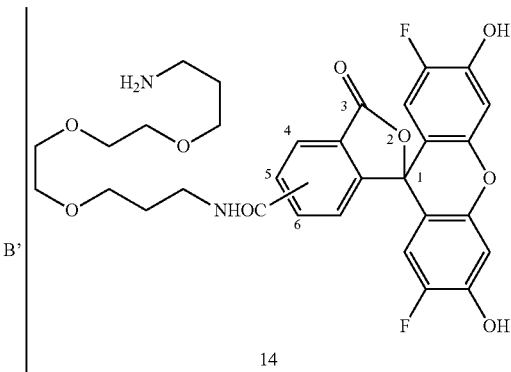

14

TTDA-Oregon Green
TTDA = 4,7,10-Trioxa-1,13-TridecaneDiamine

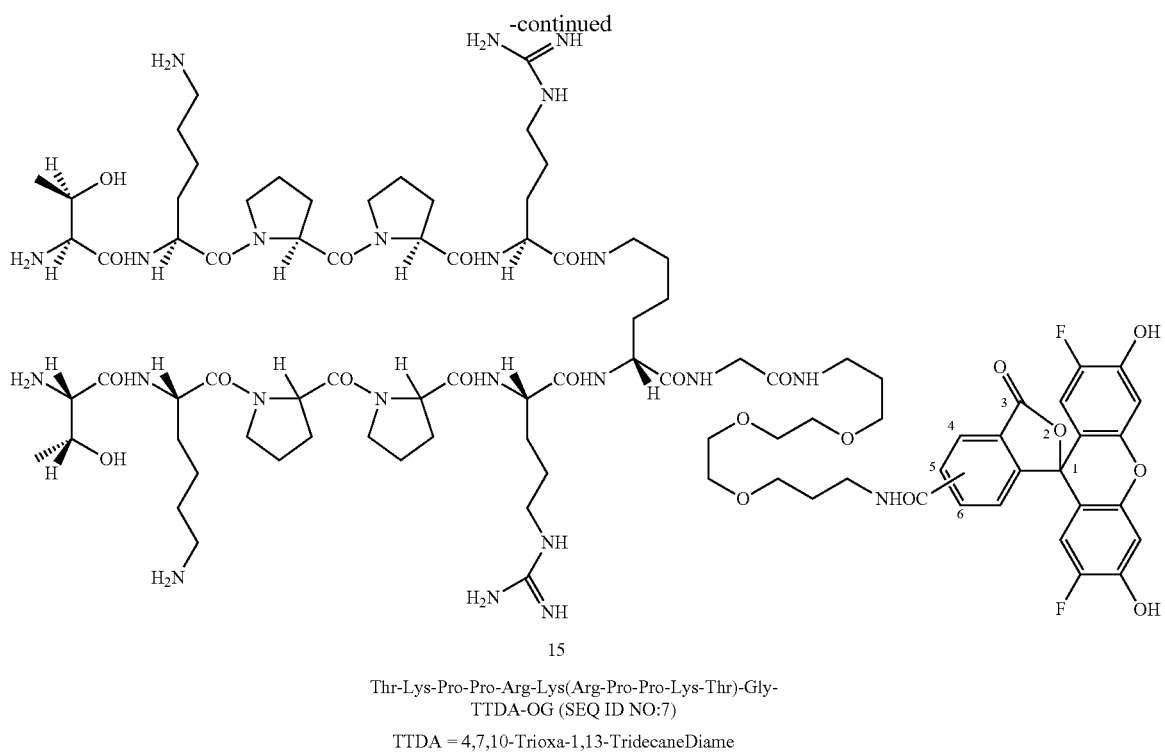

15

Thr-Lys-Pro-Pro-Arg-Lys(Arg-Pro-Pro-Lys-Thr)-Gly-TTDA-OG (SEQ ID NO:7)

TTDA = 4,7,10-Trioxa-1,13-TridecaneDiame

Likewise BRU-346 (16), a tetrameric, and an octameric construct (not shown) were also made following the same protocol as described in the synthesis of dimeric product using amino acid, Fmoc-Lys(Fmoc)-OH in the appropriate step for the necessary branching to increase the mutimeric numbers.

Tetramer BRU-346 (16):

TKPPR-K(RPPKT)-K[K(RPPKT)TKPPR]-G-Z-OG (SEQ ID NO: 8) (Tetramer)

"TKPPR" by Itself is (SEQ ID NO: 2), the Four Together are (SEQ ID NO: 9)

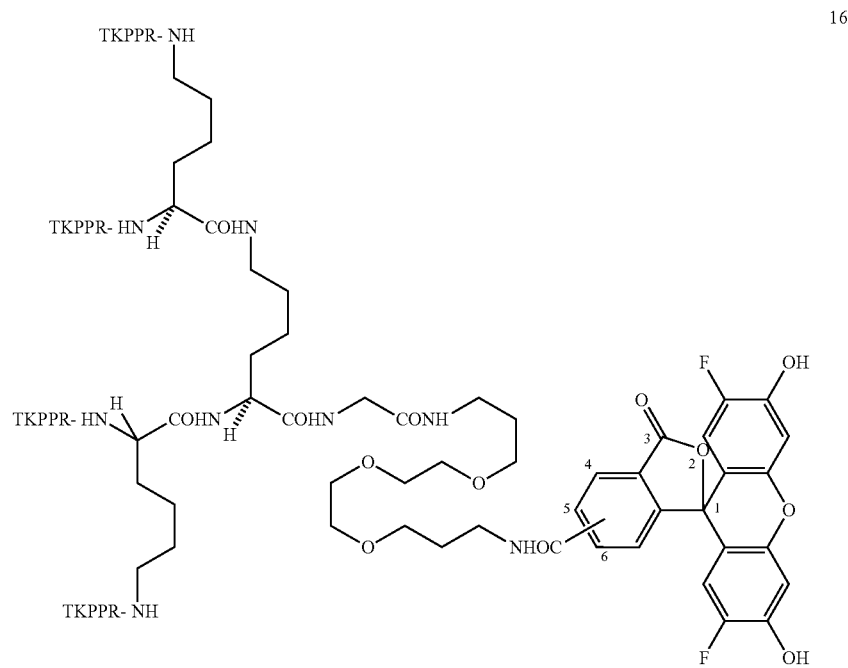

16

-continued

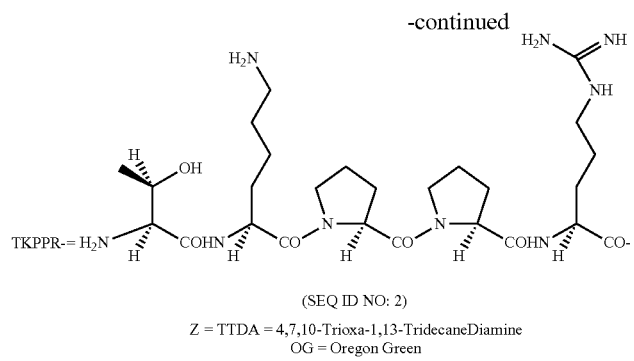

(SEQ ID NO: 2)

Z = TTDA = 4,7,10-Trioxa-1,13-TridecaneDiamine
OG = Oregon Green

BRU-346, the above tetramer, 16 was isolated and purified by HPLC, and analyzed for its purity and homogeneity by MS, $^1$HNMR and HPLC.

Results:

As shown in more detail infra, BRU-337 and BRU-346 (15 and 16) did not exhibit the same binding characteristics when compared to that of BRU-326, a similar tetrameric TKPPR (SEQ ID NO: 2) which had a linker/spacer between the bioactive TKPPR (SEQ ID NO: 2) units and the branching core (synthesized in Example 28). In BRU-337 and BRU-346 (15 and 16), TKPPR (SEQ ID NO: 2) units are attached directly to the inactive lysine core and only the reporter moiety, Oregon Green is kept farther away from the binding portion. The position of the binding unit TKPPR (SEQ ID NO: 2) close to the inert lysine core might have played an important role in decreasing the binding affinity of these compounds. With a view of that, therefore, the synthesis of similar multimeric TKPPR (SEQ ID NO: 2) on lysine core with a spacer between the binding unit and the inert lysine core should have improved binding properties.

Experimental:

General

Starting materials for the synthesis were obtained from Aldrich Chemical, Fluka Chemical and from Advanced Chemtech Co (Louisville Ky.). Solvents for reactions, chromatographic purification and HPLC analysis were E. Merck Omni grade and obtained from VWR Corporation. N-Methylpyrrolidinone (NMP), N,N-dimethylformamide (DMF), methanol (MeOH) were purchased from Fisher Scientific Company and were Peptide Synthesis grade or Bio grade quality. Piperidine (sequencing grade) was purchased from Fisher Scientific Company or from Aldrich Chemical Company (redistilled 99+%). Trifluoroacetic acid (spectrophotometric grade or sequencing grade) was purchased from Aldrich Chemical Company or from Fluka Chemical Company. Anisole (99%), diisopropylethylamine (DIEA) were purchased from Aldrich Chemical Company. O-(7-azabenzotriazol-1-yl)-1,1,3,3-tetramethyluronium hexafluorophosphate (HATU) and benzotriazole-1-yl-oxy-tis-pyrrolidinophosphonium hexafluorophosphate (PyBop) were purchased from PerSeptive Biosystems. NMR spectral data were obtained employing a Varian Instruments Innova 500 instrument. Mass spectral data were obtained on an Agilent LC-MSD (1100) single quad mass spectrometer using electrospray ionization and loop injections of purified materials. Analytical HPLC data were generally obtained using a Shimadzu LC-6A dual pump gradient system employing 250 mm×4.6 mm i.d. YMC C18 column (120 Å pore size, 10μ particle size) and gradient or isocratic elution systems using 0.1% aqueous TFA and 0.1% TFA in acetonitrile as solvent A and solvent B respectively. Detection of compounds was accomplished using UV at 220 nm.

Solid Phase Synthesis—General Procedure

Cleavage of the Fmoc Group. The cleavage of the first Fmoc group was performed with 20% piperidine in DMF (10 mL/g resin) for 5 min followed by a second treatment with 20% piperidine in DMF for 10 min. All further Fmoc-group cleavages during peptide chain elongation were performed with 25% piperidine in DMF for 10 min followed by a second treatment with 25% piperidine in DMF for 20 min.

Activation and Coupling procedure. Fmoc amino acid (4 equivalents, for multimeric constructs 6 equivalents), HATU [O-(7-azabenzotriazol-1-yl)-1,1,3,3-tetramethyluronium hexafluoro-phosphate] (4 or 6 equivalents) and diisopropylethylamine (DIEA, 6 or 8 equivalents) were dissolved in DMF (10 mL). The clear solution was transferred to the solid phase reaction vessel that contained the resin bound peptide. After shaking for 4 h, the washing procedure was applied and then samples of the resin were removed for bromophenol blue test. A double coupling was performed in a few cases of slightly positive tests.

Washing procedure. After each amino acid coupling or removals of the Fmoc group the resin was washed with 15 mL/g resin of the following solvents: DMF (3×15 mL/g), dichloromethane (3×15 mL/g) and DMF (3×15 mL/g). After the end of the synthesis and before cleavage of the peptide from the resin additional washings with acid free dichloromethane (3×15 mL/g) were performed.

Activation with Iodoacetonitrile. The resin bound N-acylsulfonamide (200 mg) was washed with NMP (3×3.0 mL). To the swollen resin were added NMP (2 mL), DIEA (5 equivalents). After filtration through an alumina basic plug prior to use, iodoacetonitrile (20 equivalents) was added to the reaction mixture and the reaction flask was shielded from light. The resin was agitated for 24 h, filtered, and washed with NMP (3×3 mL) and $CH_2Cl_2$ (3×3 mL) or THF (3×3 mL).

Nucleophilic displacement reaction with TTDA-Oregon Green. To the resin (150 mg, with activated peptide) containing flask were added DMF (2 mL), DIEA (2 equivalents) and TTDA-oregon Green (14) (1.1 equivalents) and the reaction mixture was stirred for 24 h. Filtered to remove the resin and washed the resin with $CH_2Cl_2$ (2 mL), and the combined filtrate was concentrated on a vacuum to obtain the expected product as a thick paste which was taken up for the deprotection step without further purification.

Deprotection of Peptides. Peptides obtained after nucleophilic displacement from the resin were treated with the cleavage cocktail, "Reagent B" (TFA:Water:Phenol:Triisopropylsilane, 88:5:5:2) (10 mL/g resin) for 4 h. After evaporation of the volatiles under vacuum, the paste was triturated with ether to provide a solid which was washed with ether (3×20 mL) by centrifugation and then dried under vacuum to obtain the required peptide as an orange colored solid.

Purification of peptides by reversed phase (C18) HPLC. The aqueous solution containing the peptide was loaded onto a reversed phase C18 preparative column (YMC, 10×250 mm, 10μ 120 Å) which was equilibrated with acetonitrile (2%)-water with TFA (0.1%). The column was then eluted with water-acetonitrile solvent mixture (flow rate 10 mL/min), starting a linear gradient from 10% acetonitrile to 50% acetonitrile in 60 min and fractions (5 mL size) were collected. Each fraction was analyzed on an analytical reversed phase C18 column and fractions containing the product in >99% purity were pooled and freeze-dried to provide the pure multimeric compound as an orange colored fluffy solid.

Fmoc-Gly-sulfamylbenzoyl-MBHA (1) To a 50 mL solid phase reaction flask, were added 4-sulfamylbenzoyl MBHA resin (1.0 g, 0.75 mmol/g) (swollen with DMF), DMF (10 mL), DIEA (0.72 mL, 3.75 mmol) and Fmoc-Gly-OH (2.25 mmol). The reaction mixture was shaken for 10 min followed by cooling to −20° C. After 20 min, PyBop (2.25 mmol) was added as a solid and the mixture was shaken for 8 h. The reaction mixture was then allowed to come to room temperature overnight with continued shaking after the 8 h coupling. The resin was separated from the solution by filtration, washed thoroughly with $CHCl_3$ (5×20 mL) and dried under vacuum at room temperature for 24 h. The loading of Fmoc-Gly on the resin was estimated by spectrometric analysis of the piperidine-dibenzofulvene adduct released by treatment of a small portion of the resin with piperidine. Thus the loading was found to be 0.52 mmol/g.

Dimer: TKPPRK(RPPKT)G-Z-OG (15) (SEQ ID NO: 7) Following the general procedure of solid phase peptide synthesis as outlined above, the dimeric TKPPR (SEQ ID NO: 2) construct (0.25 mmol scale) was built upon the Fmoc-Gly-sulfamylbenzoyl-MBHA (1) resin as shown in the synthesis flow chart. After completion of the loading process, the sulfamylamide nitrogen was activated by reacting with iodoacetonitrile (I-ACN) (20 equiv.) in the presence of DIEA (5 equiv.) in NMP. After subjecting to the nucleophilic displacement reaction with TTDA-OG (14) (see Scheme 1), the isolated protected peptide was then treated with the reagent 'B' (TFA:Water:Phenol:Triisopropylsilane; 88:5:5:2) to remove protecting groups. The crude peptide was then purified on a semi-preparative (C18) column to isolate the pure dimeric peptide 15 in 20% yield as an orange colored fluffy solid.

MS (ES$^+$): 980.5 (doubly charged); 654.1 (triply charged); 490.7 (tetra charged) and 392.8 (penta charged).

$^1$H NMR (D$_2$O): δ 1.15 (d, 6H, Thr-CH$_3$), 1.32-2.05 (m, 28H), 2.14-2.25 (m, 3H), 2.79-2.91 (m, 3H), 2.96-3.20 (m, 6H), 3.37-3.85 (m, 18H), 3.95-4.21 (m, 4H), 4.28-4.38 (m, 2H), 4.52-4.65 (m, 3H), 6.65-6.85 (2d, 3H), 7.35 (d, 1H), 8.05 (d, 1H) and 8.45 (s, 2H).

HPLC: Retention Time 16.23 min; Assay: >99% (area %); Column: YMC, C18; 0.46×25 cm; solvent: Water (0.1% TFA)-Acetonitrile (0.1% TFA), Initial condition: 35% acetonitrile; Linear Gradient Elution to 85% acetonitrile in 50 min; Flow rate: 1 mL/min; Detection: 220 nm Tetramer: TKPPR-K(RPPKT)-K[K(RPPKT)TKPPR]-G-Z-OG (SEQ ID NO: 8) (16) Tetramer 16 was isolated as an orange colored solid in 15% yield adopting the procedure that employed for the preparation of the dimer 15.

MS (ES$^+$): 1125.6 (triply charged); 844.5 (tetra charged); 675.9 (penta charged) and 563.5 (hexa charged).

$^1$H NMR (D$_2$O): δ 1.20 (d, 6H, Thr-CH$_3$), 1.35-2.10 (m, 50H), 2.18-2.35 (m, 5H), 2.82-2.95 (m, 6H), 2.96-3.25 (m, 10H), 3.37-3.85 (m, 24H), 4.05-4.25 (m, 7H), 4.28-4.38 (m, 3H), 4.55-4.68 (m, 5H), 6.67-6.95 (2d, 3H), 7.45 (d, 1H), 8.15 (d, 1H) and 8.55 (s, 2H).

HPLC: Retention Time 14.73 min; Assay: >98% (area %); Column: YMC, C18; 0.46×25 cm; solvent: Water (0.1% TFA)-Acetonitrile (0.1% TFA), Initial condition: 2% acetonitrile; Linear Gradient Elution to 52% acetonitrile in 25 min; Flow rate: 1 mL/min; Detection: 220 nm N-(3-{2-[2-(3-aminopropoxy)ethoxy]ethoxy}propyl)(11,16-difluoro-12,15-dihydroxy-3-oxospiro[hydroisobenzofuran-1,9'-xanthene-5/6-yl)carboxamide (14) (TTDA-Oregon Green)

i) Attachment of 4,7,10-Trioxa-1,13-tridecanediamine (TTDA) to 2-Chlorotrityl chloride PS resin. A 250 mL solid phase peptide synthesis vessel was charged with 2-chlorotritylchloride PS (polystyrene) resin (substitution level=1.12 mmol/g, 10 g, total 11.2 mmol) and the resin was thoroughly swelled (1 h, ~150 mL of CH$_2$Cl$_2$) and then washed with CH$_2$Cl$_2$ (5×75 mL). The resin was treated with 4,7,10-trioxa-1,13-tridecanediamine (24.64 g, 111.8 mmol, 10 equivalents) in a minimal amount of CH$_2$Cl$_2$ (50 mL) for 30 min with agitation of the vessel. Methanol (20 mL) was added to the reaction mixture to quench the unreacted 2-chlorotrityl groups and the agitation was continued for an additional 5 min. After removal of the solvent, the resin was washed thoroughly with CH$_2$Cl$_2$ (5×75 mL), and dried in vacuo. The loading of TTDA on the resin was estimated by first coupling with Fmoc-Gly-OH to the distal amino group of the TTDA on the resin using the DIC/HOBt coupling protocol followed by spectrometric analysis of the piperidine-dibenzofulvene adduct released by treatment of a small portion of the resin with piperidine. Thus the loading was found to be 0.68 mmol/g.

ii) Coupling of Oregon Green with TTDA-2-chlorotrityl resin. A mixture of Oregon Green (2.0 g, 4.85 mmol), EDAC (1-[3-(dimethylamino-propyl]-3-ethylcarbodiimide●HCl) (1.12 g, 5.82 mmol) and N-hydroxysuccinimide (0.67 g, 5.82 mmol) in dry DMF was stirred for 4 h at room temperature. The reaction mixture was then transferred to the N-(13-amino-4,7,10-trioxatridecanyl)-2-chlorotritylchloride PS resin (5.58 g, 3.32 mmol, pre-swelled and washed with DMF) and agitated for 24 h in a peptide synthesis vessel. The resin was filtered and washed with DMF (3×5 mL) and CH$_2$Cl$_2$ (3×5 mL), and then treated with TFA/dichloromethane (1:1, v/v) for 4 h to cleave the coupled product from the resin. The filtrate obtained from the cleavage reaction was evaporated to a paste that was triturated with ether. This provided an orange precipitate which was collected by centrifugation, washed with ether and dried. The solid was dissolved in water and loaded onto a reversed phase C18 preparative column (YMC ODS, 30×250 mm, 10μ 120 Å) pre-equilibrated with 5% acetonitrile in water (0.1% TFA). The compound was eluted from the column using a linear gradient of acetonitrile into water (both containing 0.1% TFA), starting at 10% acetonitrile and ramping to 50% acetonitrile in 60 min. The fractions (15 mL size) were analyzed on a YMC ODS analytical reversed phase C-18 column (10μ, 120 Å) and fractions containing the product in >99% purity were pooled and freeze-dried to afford the title compound 14 (0.98 g, 48% yield) as a fluffy, orange solid. HPLC: Retention time 17.08 min; Assay:

>99% (area %); Column: YMC ODS C-18; 0.46×25 cm; Eluent: Water (01% TFA)-Acetonitrile (0.1% TFA), Initial condition: 20% acetonitrile; Linear Gradient Elution to 40% acetonitrile in 20 min; Flow rate: 1 mL/min; Detection: UV at $\lambda=220$ nm; $^1$H NMR (D$_2$O; for mixture of isomers) $\delta$8.42 (s, 1H), 8.02 (d for 6-isomer), 7.78 (d, 1H), 7.42 (s for 6 isomer), 7.12 (d, 1H), 6.52 (d, 2H), 6.42 (d, 2H), 3.55 (m, 12H), 3.41 (m, 2H), 2.98 (t, 2H) and 1.75 (m, 4H) ppm; MS (ESI$^+$) m/z 615.2 (M+H)$^+$.

Example 30

Synthesis of TKPPR (SEQ ID NO: 2) Monomer Conjugated to Oregon Green (BRU-239)

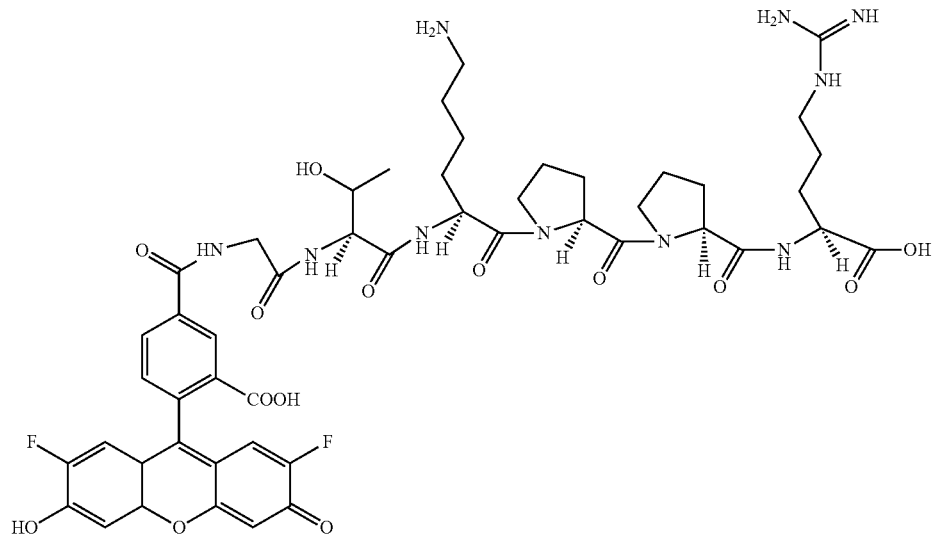

BRU 239 (Oregon Green (5-isomer)-GTKPPR-OH) (SEQ-ID NO:5)

Fmoc-Gly-Thr(tBu)-Lys(Boc)-Pro-Pro-Arg(pmc)-Wang-resin (SEQ ID NO: 5) (250 mg, 0.05 mmol was treated with 20% (v/v) piperidine in DMF (10 ml) and shaken for 10 min. It was filtered and the process was repeated. The resin was then washed with DMF (20 ml×3), Oregon Green-succinimidyl ester (5-isomer, 20 mg, 0.039 mmol) in DMF (5 ml) was added and the reaction vessel was covered with aluminum foil and shaken for 48 h. The resin was washed with DMF (20 ml×3), CH$_2$Cl$_2$ (20 ml×3) and dried by blowing N$_2$ for 15 min. 10 ml of reagent B (TFA/H$_2$O/phenol/triisopropylsilane 8.6 ml/0.5 ml/0.5 g/0.2 ml) was added and the reaction vessel was shaken for 4 h. It was filtered and the resin rinsed. The filtrate was evaporated. Ether was added to precipitate the product. The solid product was washed with ether three times by centrifuging and decanting. Half of the crude material was purified by prep. HPLC using YMC C-18 column, gradient being 0-8% CH$_3$CN/H$_2$O (0.1% TFA) in 8 min., then 8-48% in 120 min. The fractions which contained the desired product were combined and lyophilized. 12 mg of the pure compound was obtained as a pale yellow solid.

Mass Spectrum: (M+H)$^+$ at 1049.5; a doubly charged ion at 525.3.

HPLC:

YMC C-18 (0.46×25), UV at 220 nm, 10-90% CH$_3$CN/H$_2$O (0.1% TFA) in 40 min., $t_R$ at 13.6 min.

Example 31

Evaluation of the Ability of TKPPR (SEQ ID NO: 2) Monomers or Multimers To Inhibit Phospho-tyrosine Activation of the KDR/Flk-1 Receptor by VEGF in HUVEC or HAEC The ability of various compositions comprising TKPPR (SEQ ID NO: 2) monomers or multimers to inhibit phospho-tyrosine activation of the KDR/Flk-1 receptor by VEGF was evaluated using HUVECs. Nine 100 mm confluent dishes of cultured HUVEC cells were serum starved overnight in basal (EBM) medium without any additives. The next morning the plates were divided into three groups as follows:

1. 3 Plates had their medium changed to fresh EBM medium with no additions.
2. 3 plates had their medium changed to fresh EBM medium with 5 ng/mL of VEGF$_{165}$ (Peptrotech Inc.).
3. 3 plates had their medium changed to fresh EBM medium with 5 ng/mL of VEGF$_{165}$ and 250 nM TKPPR (SEQ ID NO: 2) tetramer (BRU-326).

After 5 minutes at 37° C. the dishes were all drained and quickly washed 3 times with cold D-PBS with Ca and Mg (Life Technologies). Lysates were prepared from each treatment group using Triton X-100 lysis buffer (20 mM Tris pH 8.0, 137 mM NaCl, 10% glycerol, 1% Triton X-100, 2 mM EDTA Supplemented with 1 mM PMSF, 10□g/ml Leupeptin and Aprotinin, 1 mM sodium orthovanadate, 50 mM sodium pyrophosphate, 100 mM sodium fluoride.) The pooled lysates from each group were precleared using Protein A beads from Sigma then incubated overnight with anti-KDR antibody (Sc-504 from Santa Cruz Biotech). The immune complexes were brought down by adding fresh Protein A beads. After centrifuging, the beads from each group were washed 3× with TBST, drained, and boiled 5 min in 40 µL Laemmli sample buffer with mercaptoethanol (from Bio-Rad). Half of each of the samples was resolved by SDS-PAGE on a 7.5% gel and transferred to a PVDF membrane using standard methods. The blot was probed for phospho-tyrosine using the PY20 antibody from Transduction Labs at 1:200 dilution using an ECL Western blotting kit from Amersham following their protocol with the anti-mouse HRP secondary antibody. After probing the blot with PY20, it was stripped as recommended by Amersham and reprobed for total KDR with Sc-315 antibody (1:200 dilution) from Santa Cruz Biotech, using the ECL Western blotting kit from Amersham following their protocol with the anti-rabbit HRP secondary antibody. The intensity of phosphorylated (active) KDR for each treatment group was determined from the PY-20 blot then normalized to the total amount of KDR present as determined by re-probing with anti-KDR (sc-315). The results are shown in FIG. 1.

Results:

Without VEGF, no phosphorylated KDR was detectable. Addition of VEGF resulted in a heavily phosphorylated band of KDR on the blot. If VEGF and BRU-326 (1 µM) were added simultaneously to HUVECs, only a light band of phosphorylated KDR was visible, consistent with about a 60% inhibition of KDR activation by BRU-326 (see FIG. 1). In another experiment, 200 µM TKPPR (SEQ ID NO: 2) (BRU-95) had no effect on the ability of VEGF to activate KDR (not shown).

Example 32

Evaluation of the Ability of TKPPR (SEQ ID NO: 2) Monomers and Multimers to Inhibit $^{125}$I-VEGF Binding to NP-1 Fc The ability of various compositions comprising TKPPR (SEQ ID NO: 2) monomers or multimers to inhibit $^{125}$I-VEGF binding to NP-1 was evaluated using NP-1/Fc. Competitive binding assays with microtiter plates coated with NP-1/Fc (R&D systems) were performed using $^{125}$I-VEGF$_{165}$ as radioligand (Amersham Pharmacia Biotech Cat. No. IM274, Specific Activity: 1000-2500 Ci/mmol). An assay buffer consisting of Hank's Balanced Salt Solution (HBSS), 25 mM HEPES, and 0.1% BSA, pH 7.4 was used, and for all experiments, Assay volume per well was 75 µl. Plates (Nunc MaxiSorp white opaque Microtiter plate [C-bottom, 437796]) were coated by incubating the wells with 75 µl of a solution containing 3 µ 1 g/mL NP-1/Fc in D-PBS/0.1% NaAzide overnight at 4° C. after covering with sealing tape (Dynex, VWR Cat. No. 62402-931). The next day all wells, even control wells lacking NP-1/Fc, were blocked 2 hrs with blocking buffer (1% BSA in D-PBS with 0.05% v/v Tween-20) then washed 4× with PBST (D-PBS/0.05% v/v Tween-20) before starting the assay. All points were derived from triplicate wells, and for each set of replicates in NP-1/Fc-coated wells, a companion set in the absence of the receptor was included. For competitive binding, a series of unlabelled competitor concentrations were prepared in a 250 pM solution of $^{125}$I-VEGF$_{165}$ in assay buffer. Solutions were added to 1.2 ml polypropylene tubes conforming to the microtiter format (Costar Cat. No. 29442-602), and transferred from these tubes to microtiter wells, without further dilution, using a multichannel pipettor. After addition of the appropriate solutions, microtiter plates were incubated at 4° C. for 2 hours. Following the incubation, plates were hand-washed 5 times with D-PBS containing 0.05% Tween-20 and 0.1% BSA. The plates were blotted dry and 25 µl deionized water and 100 µl scintillation fluid (Optiphase SuperMix, Wallac) were added to each well. Plates were agitated using a Plate Shaker (Hyperion, Cat. No. 4030-100F) for 3-5 minutes and were then counted using a Microplate Scintillation Counter (Wallac Microbeta Trilux) A set of serially diluted $^{125}$I-VEGF$_{165}$ standard wells ranging from 200 to 0.04 pM were included with each experiment to aid in quantification of the amount of radiolabel bound. VEGF$_{165}$ (Cat. No. 100-20) was obtained from Peprotech.

Results:

When increasing concentrations of the competing compounds listed below were added to the assay, there were varying amounts of inhibition of $^{125}$I-VEGF$_{165}$ binding to NP-1 Fc, ranging from no inhibition at 1 µM (negative control peptide) to an IC$_{50}$ of 500 pM (unlabeled VEGF$_{165}$). Tuftsin (TKPR) (SEQ ID NO: 1) was 5 to 6-fold less potent a binding inhibitor than TKPPR (SEQ ID NO: 2). Adding Oregon Green (OG), a fluorescein derivative to TKPPR (SEQ ID NO: 2) (BRU-239) had little if any significant effect on the peptide's potency. Multmeric forms of TKPPR (SEQ ID NO: 2) however, were much more potent than monomeric TKPPR (SEQ ID NO: 2), with the potency increasing with the valency of the compound. Thus, the dimer of TKPPR (SEQ ID NO: 2) (OG-(TKPPR)$_2$ (SEQ ID NO: 10), (BRU-317) was 10 to 14-fold more potent than the monomer, and the tetramer of TKPPR (SEQ ID NO: 2) (OG-(TKPPR)$_4$ (SEQ ID NO: 9), BRU-326) was 230 to 330-fold more potent than the monomer. However, a tetramer of TKPPR (SEQ ID NO: 2) created by attaching the peptide to a scaffold through its arginine residue rather than the threonine residue (BRU-346) was much less potent than the original tetrameric TKPPR (SEQ ID NO: 2) (BRU-326), although it was still more potent than the TKPPR (SEQ ID NO: 2) monomer. Thus, the activity of TKPPR (SEQ ID NO: 2) multimers appears to depend on how the peptide is assembled into its multimeric form.

| Agent | IC$_{50}$ | BRU # |
| --- | --- | --- |
| VEGF | 0.5 nM | — |
| OG-(TKPPR)$_4$ (SEQ ID NO: 9) | 0.13 µM | BRU-326 |
| OG-(TKPPR)$_2$ (SEQ ID NO: 10) | 3 µM | BRU-317 |
| Reverse Tetramer | 8.0 µM | BRU-346 |
| OG-TKPPR (SEQ ID NO: 2) | 30 µM | BRU-239 |
| TKPPR (SEQ ID NO: 2) | 43 µM | BRU-95 |
| Tuftsin (TKPR) (SEQ ID NO: 1) | 280 µM | — |
| TPATSVRG (SEQ ID NO: 11) (negative control) | Inactive at 1 mM | BRU-170 |

Equivalent assays conducted by substituting KDR-Fc for NP-1/Fc showed that none of the TKPPR (SEQ ID NO: 2)-derived compounds listed above, including BRU-326 were able to inhibit $^{125}$I-VEGF$_{165}$ binding to KDR even at the highest concentrations tested. This indicates that these compounds are selective for NP-1.

Example 33

Evaluation of the Ability of a TKPPR (SEQ ID NO: 2) Monomer and a TKPPR (SEQ ID NO: 2) Multimer to Inhibit $^{125}$I-VEGF Binding to Human Umbilical Vein Endothelial Cells (HUVECS)

The ability of compositions comprising a TKPPR (SEQ ID NO: 2) monomer and a TKPPR (SEQ ID NO: 2) multimer to inhibit $^{125}$I-VEGF binding to endothelial cells was evaluated using HUVECs. Competitive binding assays with HUVECs were carried out as described by Bikfalvi et al. (J. Cell. Physiol. 149:50-59, 1991), incorporated herein by reference in its entirety, using HUVECs obtained from Clonetics and cultured in EGM-MV medium from BioWhittaker as recommended by Clonetics. A TKPPR (SEQ ID NO: 2) tetramer compound (BRU-326) and a TKPPR (SEQ ID NO: 2) monomeric compound (BRU-95) were evaluated.

Figure 2:
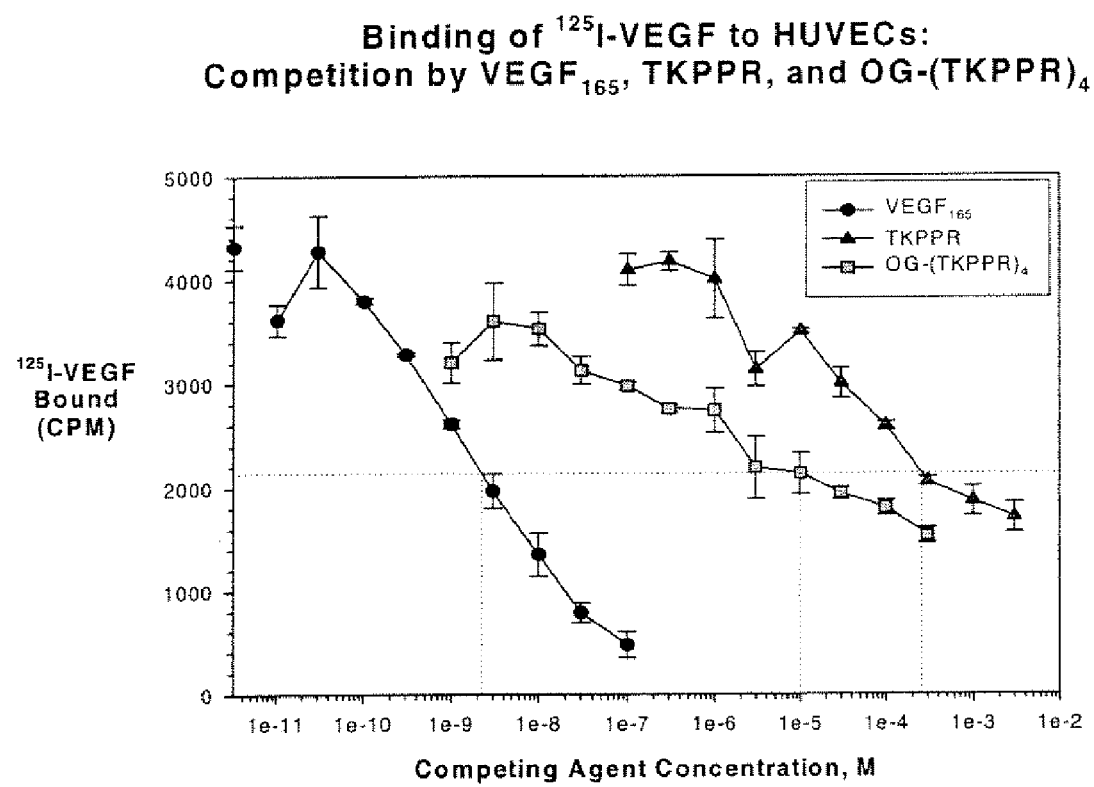
FIG. 2: Binding of $^{125}$I-VEGF to HUVECs is inhibited by a TKPPR (SEQ ID NO: 2) monomer and multimer. Effect of competition with increasing concentrations of unlabeled VEGF (circles), tetrameric TKPPR (SEQ ID NO: 2) (BRU-326, squares), and monomeric TKPPR (SEQ ID NO: 2) (BRU-95, triangles). Both the TKPPR tetramer and monomeric were able to inhibit binding to $^{125}$I-VEGF binding to receptors on HUVECs, although tetrameric TKPPR (SEQ ID NO: 2) (BRU-326) was more potent ($IC_{50}$=10 µM) than monomeric TKPPR (SEQ ID NO: 2) (BRU-95, $IC_{50}$=250 µM).

Results:

When a TKPPR (SEQ ID NO: 2) tetramer and monomeric TKPPR (SEQ ID NO: 2) were tested as competitors of $^{125}$I-VEGF binding to HUVECs, both were able to inhibit binding to VEGF receptors on HUVECs, although tetrameric TKPPR (SEQ ID NO: 2) (BRU-326) was more potent ($IC_{50}$=10 µM) than monomeric TKPPR (SEQ ID NO: 2) (BRU-95, $IC_{50}$=250 µM). See FIG. 2. While essentially all $^{125}$I-VEGF binding could be inhibited by unlabeled VEGF, it appeared that a portion could not be blocked by monomeric or tetrameric TKPPR (SEQ ID NO: 2), consistent with the presence of other VEGF receptors not susceptible to inhibition by either form of TKPPR (SEQ ID NO: 2).

Example 34

Evaluation of the Ability of TKPPR (SEQ ID NO: 2) Monomers and Multimers to Bind to the NP-1 and KDR VEGF Receptors by Fluorescence Polarization (FP)

The ability of various compositions comprising TKPPR (SEQ ID NO: 2) monomers or multimers to bind to NP-1/Fc and KDR-Fc was evaluated using FP. The binding studies of various Oregon Green (OG)-labeled compounds comprising TKPPR (SEQ ID NO: 2) monomers or multimers and related compounds with Neuropilin-1/Fc, and KDR-Fc (both from R&D Systems), were carried out at 37° C. in D-PBS buffer (pH 7.4). FP values (mP) for each substrate was measured by titrating the ligand (5-20 nM) with receptor protein using a Jolley Research and Consulting FPM-1 fluorescence Polarization analyzer. In each of these experiments the observed polarization values were plotted against receptor concentration. The mP values for 100% binding of tracer labeled ligand to receptor protein was calculated using the software provided by the vendor. One half of this value corresponds to the value of mP at 50% binding and the corresponding concentration of Npn-1 represents the dissociation constant ($K_d$) of the ligand.

Figure 3:
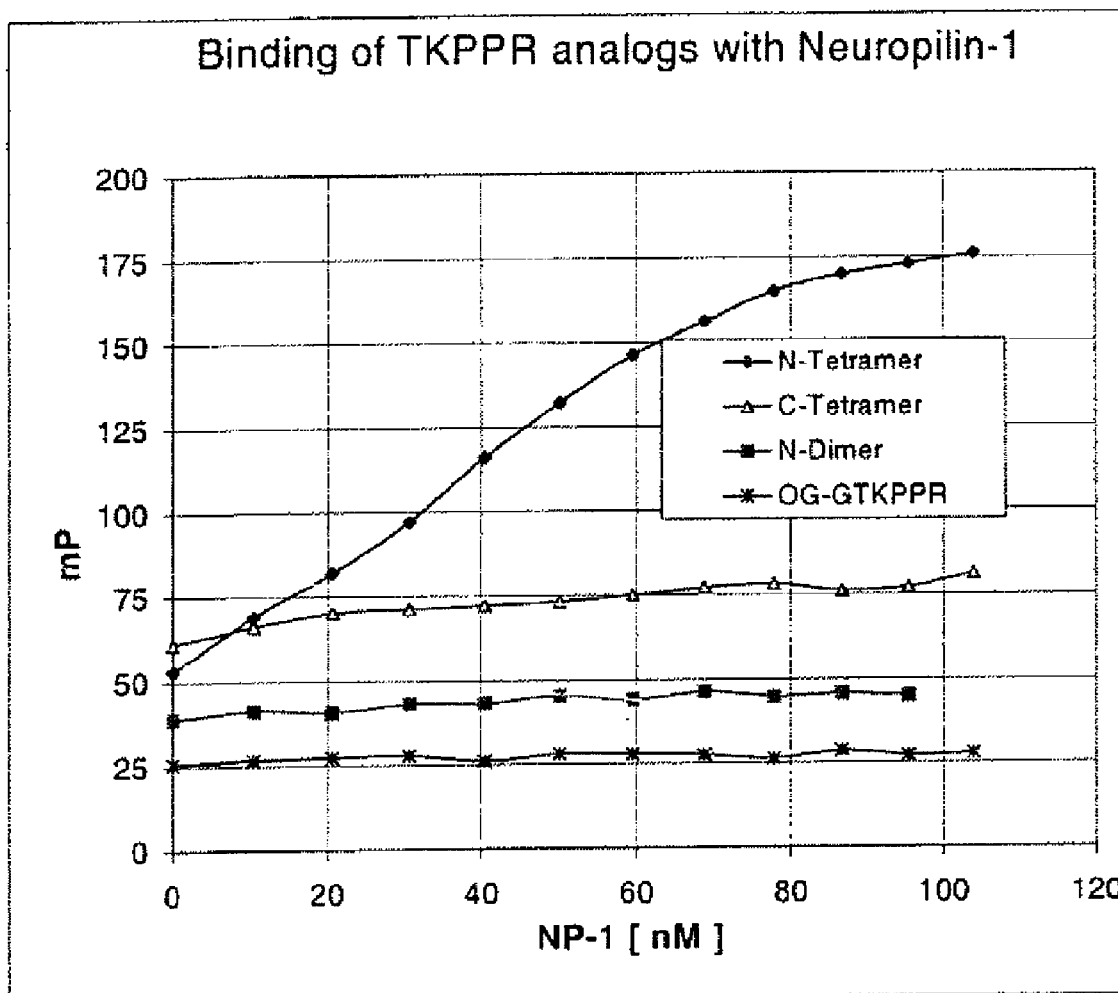
FIG. 3: Binding of TKPPR (SEQ ID NO: 2) derivatives with NP-1/Fc by Fluorescence Polarization. The indicated Oregon Green-labeled derivatives were incubated with increasing concentrations of NP-1 and polarization was measured. Fluorescently-labeled TKPPR (SEQ ID NO: 2) tetramer (BRU-326) bound tightly to NP-1 ($K_d$=25-50 nM in different experiments). Binding of TKPPR (SEQ ID NO: 2) dimer (BRU-317) was barely detectable by fluorescence polarization (FP). The binding to NP-1 could be competed by unlabeled free TKPPR (SEQ ID NO: 2) monomer ($IC_{50}$=80 µM) and VEGF ($IC_{50}$=200 nM). Binding of OG-TKPPR (SEQ ID NO: 2) monomer (BRU-239) to NP-1/Fc was not detectable. Binding of tetrameric TKPPR (SEQ ID NO: 2) linked to a different scaffold through the C-terminal amino acid of TKPPR (SEQ ID NO: 2) (BRU-346) was also negative. These results are consistent with the radioligand binding data with $^{125}$I-VEGF, but also add to them by demonstrating direct binding of the TKPPR (SEQ ID NO: 2) tetramer (BRU-326) to NP-1/Fc.
Figure 4:
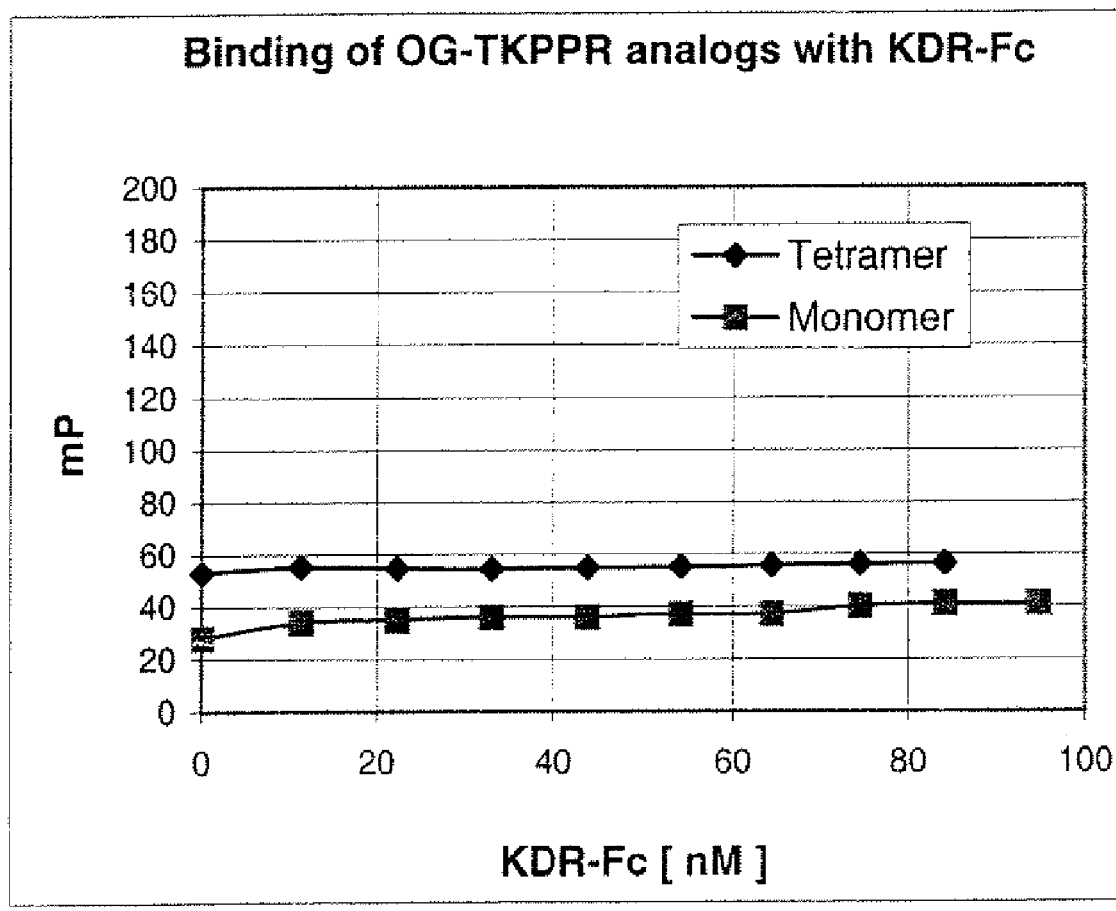
FIG. 4: Binding of TKPPR (SEQ ID NO: 2) derivatives with KDR-Fc by FP. OG-labeled TKPPR (SEQ ID NO: 2) monomer (BRU-239) and tetramer (BRU-326) were incubated with increasing concentrations of KDR-Fc and polarization was measured. Neither the fluorescently-labeled TKPPR (SEQ ID NO: 2) tetramer (BRU-326) nor the fluorescently-labeled monomer (BRU-239) bound to KDR-Fc.

Results:

Fluorescently-labeled TKPPR (SEQ ID NO: 2) tetramer (BRU-326) bound tightly to NP-1 ($K_d$=25-50 nM in different experiments) (FIG. 3), but not to KDR-Fc (FIG. 4). Binding of TKPPR (SEQ ID NO: 2) dimer (BRU-317) to NP-1 was barely detectable by FP (FIG. 3). The binding to NP-1 could be competed by unlabeled free TKPPR (SEQ ID NO: 2) monomer ($IC_{50}$=80 µM) and $VEGF_{165}$ ($IC_{50}$=200 nM), but $VEGF_{121}$ had no effect at up to 250 nM. Binding of OG-TKPPR (SEQ ID NO: 2) monomer (BRU-239) to NP-1/Fc was not detectable. Binding of tetrameric TKPPR (SEQ ID NO: 2) linked to a different scaffold through the C-terminal amino acid of TKPPR (SEQ ID NO: 2) (BRU-346) to NP-1 was also negative. These results are consistent with the radioligand binding data with $^{125}$I-VEGF, but also add to them by demonstrating direct binding of the TKPPR (SEQ ID NO: 2) tetramer (BRU-326) to NP-1/Fc.

Example 35

Comparison of the Ability of $VEGF_{165}$ and $VEGF_{121}$ to Inhibit the Binding of Composition I of Example 5 (BRU 114) to HAEC in Static Culture Assays were performed as described for Example 7 using microbubble compositions containing 2% BRU-114 (as a % of total phospholipid in the composition).

Results

As indicated in the table below, $VEGF_{121}$ has little if any ability to inhibit the binding of microbubbles containing BRU-114 in their composition to HAEC. $VEGF_{165}$ however, potently blocked bubble binding. $VEGF_{121}$ is known not to interact with NP-1, but instead specifically binds Flt-1 and KDR. On the other hand, $VEGF_{165}$ containing a heparin-binding domain absent in $VEGF_{121}$, is known to bind to most VEGF receptors, including NP-1. Thus, these results, in combination with the FP and radioligand binding data presented with KDR-Fc and NP-1/Fc, strongly suggest that the binding target for TKPPR (SEQ ID NO: 2) on endothelial cells is NP-1 and not KDR.

TABLE

Bubble Binding to HAEC- Effect of competition with $VEGF_{165}$ and $VEGF_{121}$ on binding frequency. Binding is represented as average total bubbles bound (of duplicate measurements).

| Treatment | Bubbles Bound |
|---|---|
| None | 953 |
| 25 ng/ml VEGF165 | 144 |
| 100 ng/ml VEGF165 | 94 |
| 200 ng/ml VEGF165 | 70 |
| 100 ng/ml VEGF121 | 878 |
| 200 ng/ml VEGF121 | 849 |
| 400 ng/ml VEGF121 | 778 |

Example 36

Synthesis of TKPPR (SEQ ID NO: 2) Tetramer Conjugated to Oxa-PnAO Metal Chelating Group (BRU-363)

Synthetic scheme:

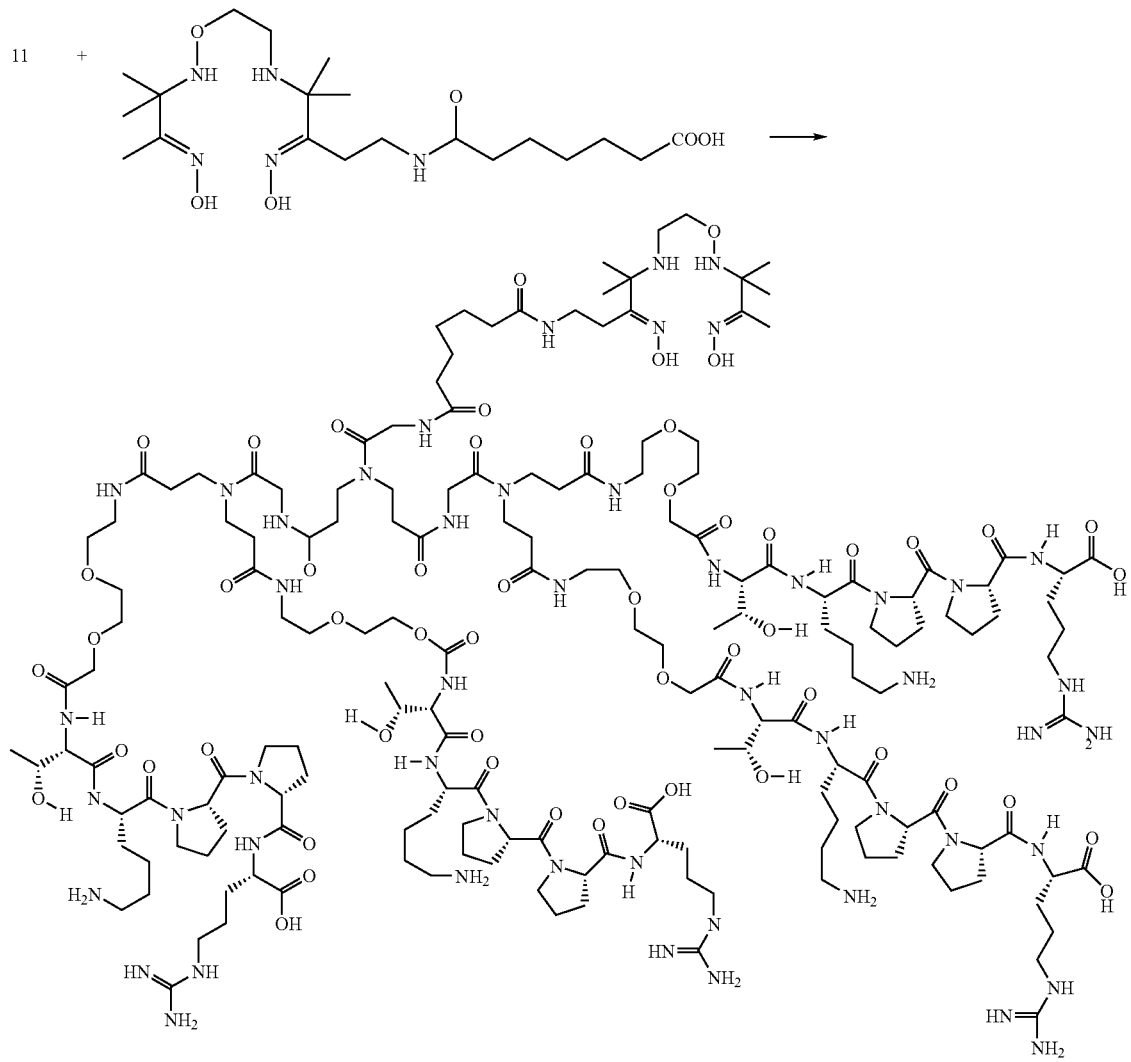

BRU-363

Experimental

BRU-363:

A solution of the oxa-PnAO acid (BRU-351*, 0.44 g, 0,0787 mmol) was dissolved in 200 mL of NMP and cooled in an ice bath. HATU (38 mg, 0.01 mmol) was added followed by DIEA (26.0 mg, 0.02 mmol) and the solution was stirred for 30 min at 0° C. Amine 11 (0.168 g, 0.0309 mmol) was then added as solid followed by DIEA (13.0 mg, 0.1 mmol) and the reaction mixture was stirred at RT for 20 h. The mixture was diluted with water (10 ml) and extracted with dichloromethane (3×20 ml). The organic layers were combined and washed with saturated sodium bicarbonate (3×20 ml), water (3×20 ml) and dried (sodium sulfate). Evaporation of the solvent after filtering the drying agent yielded a colorless gum and the crude product was dried at RT under high vacuum (<0.1 mm) for 20 h. The above dried product was dissolved in 10 ml of Reagent B (88:5:5:2—TFA:Water:Phenol:Triisopropylsilane) and stirred at RT for 5 h. All the volatiles were removed under reduced pressure and the residue was triturated with anhydrous ether (10 ml). The precipitated solid was filtered off and washed with ether (3×10 ml) and dried. The above solid was then purified on a preparative HPLC column [YMC C18 RP column; 250n×30 mm; S-10P m; 120 Å; Elution rate: 25 ml/min; Detection—220 nm; Solvent A: Water with 0.1% TFA; Solvent B—ACN with 0.1% TFA; 2-62% B in 120 min]. The fractions containing the major peak (purity>95%) were pooled and freeze dried to yield the product as a colorless fluffy solid. Yield: 0.043 g (25%); $t_R$: 27.13 min (YMC RP $C_{18}$ column; 250×4.6 mm; Elution rate: 1 ml/min; Detection—220 nm; 5-60% B in 30 min; Purity>98%]. $^1$H NMR in $D_2O$ showed the entire expected characteristic peaks of the molecule and the integral ratio of the one set of gem dimethyls on the PnAO core (see U.S. Pat.

No. 6,093,382, incorporated by reference herein in its entirety) and the four threonine units agreed (1:2). MS m/z 987.2 [M+4H]/4, 789.9 [M+5H]/5, 658.5 [M+6H]/6, 564.6 [M+7H]/7.

Example 37

Preparation of a $^{99m}$Tc Radiopharmaceutical of the Invention ($^{99m}$Tc-Oxa PnAO(TKPPR)$_4$) (SEQ ID NO: 9)

The TKPPR (SEQ ID NO: 2)-metal chelator conjugate of the previous example (BRU-363) may be complexed with a radioactive metal as explained below for $^{99m}$Tc. A stannous DTPA solution may be prepared by dissolving SnCl$_2$.2H$_2$O (11.9 mg, 0.058 mmol) in 1.2 mL of N$_2$-purged 0.1N HCl. To this 25 mL of N$_2$-purged water and Na$_2$DTPA (524 mg, 1.05 mmol) may be added and the solution can be brought to a final volume of 50 mL. Oxa PnAO(TKPPR)$_4$ (SEQ ID NO: 9) ligand (1 mg) may be dissolved in 1 mL of 0.1M phosphate buffer, pH 8.1. A 400-μL aliquot of this solution may be mixed with 100 μL (10-20 mCi) of $^{99m}$TcO$_4^-$, followed by 75 μL of the stannous DTPA solution. After 15 minutes at room temperature, an aliquot of the reaction mixture may be injected onto a YMC basic S-5 HPLC column [250×4.6 mm] and the gradient below can be used at a flow rate of 1.0 mL/min. to separate unchelated ligand from the $^{99m}$Tc-OxaPnAO(TKPPR)$_4$ (SEQ ID NO: 9) complex. Both radioactivity and UV (A$_{220}$) traces should be monitored.

t=0 min, 100% H$_2$O (0.1% TFA)
5 min, 100% H$_2$O (0.1% TFA)
30 min, 70% H$_2$O (0.1% TFA)/30% ACN
50 min., 70% H$_2$O (0.1% TFA)/30% ACN
52 min, 100% H$_2$O (0.1% TFA)

Fractions from the HPLC that contain the desired radioactive complex can be isolated, evaporated to near dryness, and then dissolved in normal saline or a physiologically acceptable buffer such Dulbecco's phosphate-buffered saline (DPBS, Na$_2$HPO$_4$ 8.1 mM, KH$_2$PO$_4$ 1.5 mM, KCl 2.7 mM, NaCl 137 mM, pH 7.5) for subsequent testing.

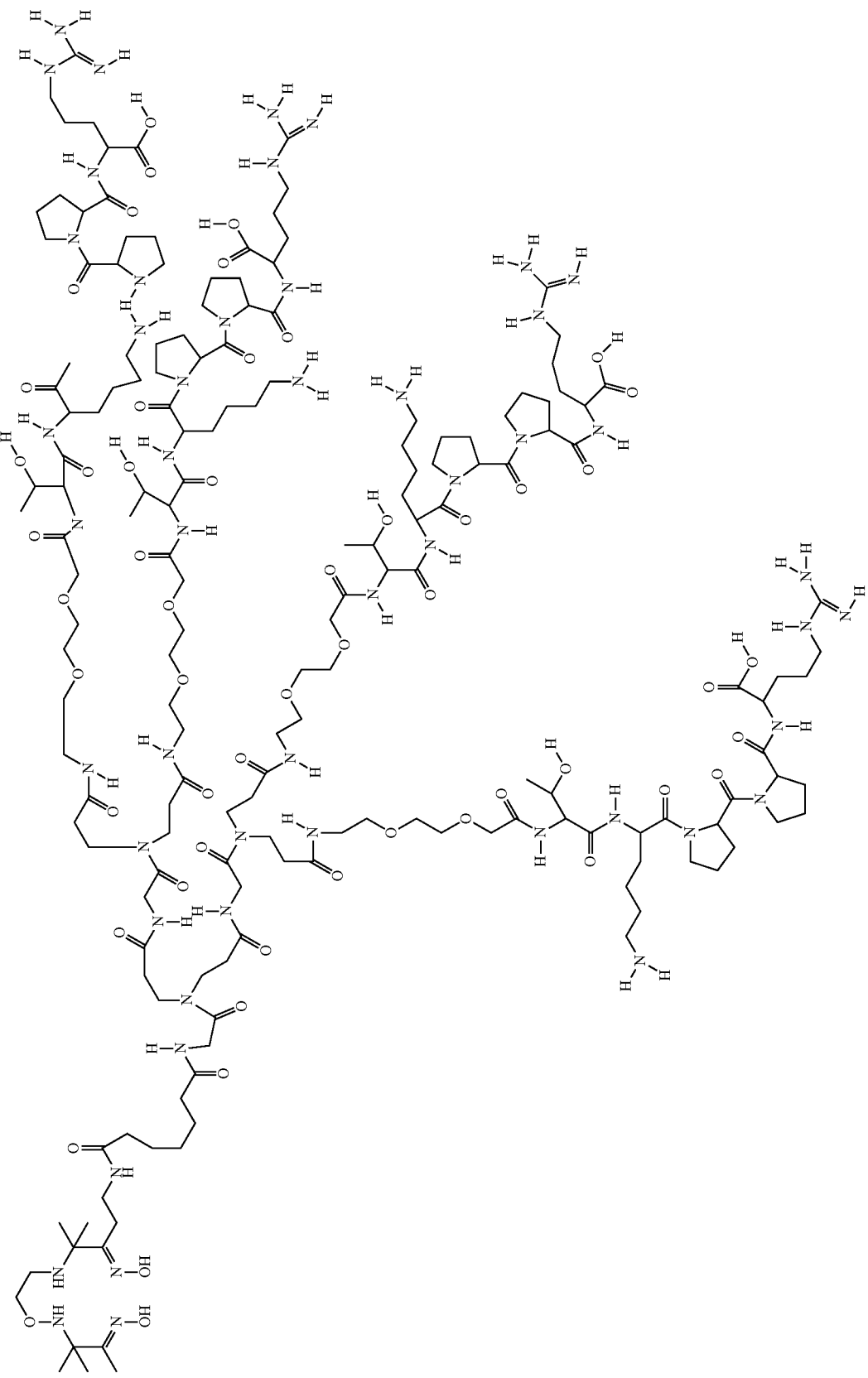
Structure of Oxa PnAO(TKPPR)4 (SEQ ID NO: 9) ligand

It is to be understood that, while the foregoing invention has been described in detail by way of illustration and example, only the preferred or specific embodiments have been revealed, and that numerous modifications, substitutions, and alterations are all permissible without departing from the spirit or scope of the invention as described in the following claims.

We claim:

1. A composition which comprises a compound of the formula (I)

A-L-B (I)

in which:

A is a multimer or polymer of TKPPR (SEQ ID NO: 2), or a multimer or polymer of a TKPPR (SEQ ID NO: 2) analogue which contains TKPPR (SEQ ID NO: 2) and which specifically binds to NP-1 or cells that express NP-1 with avidity that is equal to or greater than TKPPR (SEQ ID NO: 2);

L is a linker; and

B is a phospholipid.

2. A composition according to claim 1, in which L is a bond, an oligopeptide, a difunctional PEG derivative or is derived from: an alkyl chain $C_1$-$C_{6000}$, linear or branched, saturated or unsaturated, optionally interrupted or substituted by one or more groups such as: O, S, NR, OR, SR, COR, COOH, COOR, CONHR, CSNHR, C═O, S═O, S(═O)$_2$, P═O(O)$_2$OR, P(O)$_2$(OR)$_2$, halogens, or phenyl groups, optionally substituted by one or more —NHR, —OR, —SR, —COR, —CONHR, —N—C═S, —N—C═O, halogens, in which R is H or an alkyl group $C_1$-$C_4$, linear or branched, optionally substituted by one or more —OH; such a chain can be interrupted or substituted by one or more cyclic groups $C_3$-$C_9$, saturated or unsaturated, optionally interrupted by one or more O, S or NR; by one or more groups such as: —NHR, —OR, —SR, —COR, —CONHR, or a phenyl group optionally substituted by one or more —NHR, —OR, —SR, —COR, —CONHR, —N—C═S, —N—C═O, halogens.

3. A composition according to claim 2, in which the cyclic groups present in L are saturated or unsaturated, and correspond to the following general formula (III)

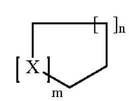

(III)

in which:

n can range from 0 to 4;

m can range from 0 to 2;

X can be NH, NR, O, S or SR.

4. A composition according to claim 2, in which the linker L is an oligopeptide comprising 1 to 100 natural or synthetic amino acids.

5. A composition according to claim 4, in which the amino acids are selected from the group consisting of glycine, glutamic acid, aspartic acid, γ-amino-butyric acid and trans-4-aminomethyl-cyclohexane carboxylic acid.

6. A composition according to claim 2, in which L is derived from difunctional PEG(polyethyleneglycol) derivatives.

7. A composition according to claim 2, in which L is selected from the group consisting of: glutaric acid, succinic acid, malonic acid, oxalic acid and PEG derivatized with two $CH_2CO$ groups.

8. A compound of the formula (IIa)

$$A\text{-}L\text{-}B_{1a} \quad (IIa)$$

in which:
A is a multimer or polymer of TKPPR (SEQ ID NO: 2), or a multimer or polymer of a TKPPR (SEQ ID NO: 2) analogue which contains TKPPR (SEQ ID NO: 2) and which specifically binds to NP-1 or cells that express NP-1 with avidity that is equal to or greater than TKPPR (SEQ ID NO: 2);
L is a linker; and
$B_{1a}$ comprises a phospholipid moiety of the formula (II),

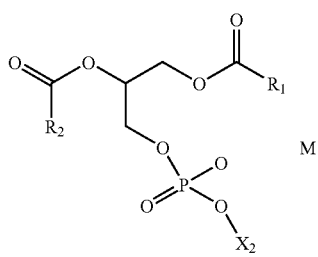

(II)

where
M is an alkaline or alkaline-earth metal cation;
$R_1$ and $R_2$ independently, correspond to a linear long chain $C_{12}$-$C_{20}$, saturated or unsaturated, optionally interrupted by C=O, or O; and
$X_2$ is selected from the group consisting of

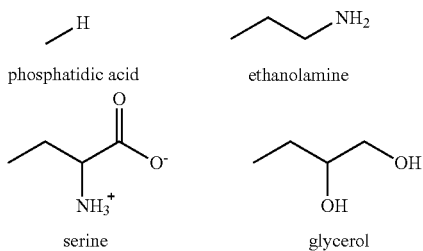

phosphatidic acid, ethanolamine, serine, glycerol

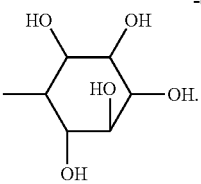

inositol

9. A compound according to claim 8, in which $R_1$ and $R_2$ are independently a saturated linear long chain $C_{12}$-$C_{20}$.

10. A compound according to claim 9, in which the phospholipid of formula (II) comprises a phospholipid selected from the group consisting of: dimyristoylphosphatidylethanolamine, dipalmitoylphosphatidylethanolamine, distearoylphosphatidylethanolamine, diarachidoylphosphatidylethanolamine, dioleylphosphatidylethanolamine, dilinoleylphosphatidylethanolamine, fluorinated analogues of any of the foregoing, and mixtures of any of the foregoing.

11. A compound according to claim 10, in which the phospholipid of formula (II) comprises dipalmitoylphosphatidylethanolamine.

12. An ultrasound contrast agent comprising a suspension of gas-filled microbubbles, in which the microbubbles comprise a compound of any one of claims 8 to 11.

13. An ultrasound contrast agent comprising a suspension of gas-filled microbubbles, in which the microbubbles comprise a compound of claim 8 and the gas comprises a fluorinated gas.

14. An ultrasound contrast agent comprising a suspension of gas-filled microbubbles in which the microbubbles comprise a compound of claim 8 in which A is a TKPPR (SEQ ID NO: 2) multimer or polymer and the gas comprises $SF_6$, or a perfluorocarbon selected from the group consisting of $C_3F_8$, $C_4F_8$, $C_4F_{10}$, $C_5F_{12}$, $C_6F_{12}$, $C_7F_{14}$ and $C_8F_{18}$.

* * * * *